(12) United States Patent
Moore et al.

(10) Patent No.: US 7,794,712 B2
(45) Date of Patent: Sep. 14, 2010

(54) **PRODUCTION OF MUTANT STRAIN OF *ASPERGILLUS FUMIGATUS*, METHOD OF ASSAY FOR INHIBITING SIDEROPHORE BIOSYNTHESIS AND DIAGNOSTIC METHOD FOR DETECTING LIKELY *ASPERGILLUS FUMIGATUS* INFECTION**

(75) Inventors: Margo Marie Moore, North Vancouver (CA); Anna Hodiah Tangen Hissen, Port Moody (CA); Nga Chun Adrian Wan, Burnaby (CA)

(73) Assignee: Simon Fraser University, Burnaby (CA)

( * ) Notice: Subject to any disclaimer, the term of this patent is extended or adjusted under 35 U.S.C. 154(b) by 0 days.

(21) Appl. No.: 11/155,655

(22) Filed: Jun. 20, 2005

(65) Prior Publication Data

US 2006/0079580 A1   Apr. 13, 2006

Related U.S. Application Data

(60) Provisional application No. 60/580,978, filed on Jun. 21, 2004.

(30) Foreign Application Priority Data

Jun. 18, 2004   (CA)   .................................. 2472695

(51) Int. Cl.
C12Q 1/68   (2006.01)
(52) U.S. Cl. ........................... 424/130.1; 435/6; 435/7.1
(58) Field of Classification Search ........................ None
See application file for complete search history.

(56) References Cited

U.S. PATENT DOCUMENTS

| | | | |
|---|---|---|---|
| 5,554,507 | A | 9/1996 | Grossman et al. |
| 6,090,581 | A | 7/2000 | Gavrias |

FOREIGN PATENT DOCUMENTS

| | | |
|---|---|---|
| CA | 2101493 | 1/1994 |
| CA | 2460873 | 9/2005 |
| WO | 02086090 | 10/2002 |
| WO | 2004067709 | 8/2004 |
| WO | 2005/093036 | 10/2005 |

OTHER PUBLICATIONS

Pinel et al., J. Clin. Microbiol., 41:2184-2186, 2003.*
Hissen et al., J. Biol. Inorg. Chem., 10:211-220, 2005.*
Campbell et al. (Monoclonal Antibody Technology, Elsevier Science Publishers, 1984, pp. 1-32).*
Heymann et al. (BioMetals 12:301-306, 1999).*
Martin Eisendle et al., The siderophore system is essential for viability of *Aspergillus nidulans*: functional analysis of two genes encoding L-ornithine N5-monooxygenase (sidA) and a non-ribosomal peptide synthetase (sidC), Molecular Microbiology (2003) 49(2), p. 359-375.

Martin Eisendle et al., Biosynthesis and Uptake of Siderophores Is Controlled by the PacC-Mediated Ambient-pH Regulatory System in *Aspergillus nidulans*, Eukaryotic Cell, Apr. 2004, p. 561-563, vol. 3, No. 2.
Martin Eisendle, et al., The Intracellular Siderophore Ferricrocin Is Involved in Iron Storage, Oxidative-Stress Resistance, Germination, and Sexual Development in *Aspergillus nidulans*, Eukaryotic Cell, Oct. 2006, p. 1596-1603, vol. 5, No. 10.
Maria Fluckinger, et al., Human Tear Lipocalin Exhibits Antimicrobial Activity by Scavenging Microbial Siderophores, Antimicrobial Agents and Chemotherapy, Sep. 2004, p. 3367-3372, vol. 48, No. 9.
H Haas, Molecular genetics of fungal siderophore biosynthesis and uptake: the role of siderophores in iron uptake and storage, Mini Review, Appl Microbiol Biotechnol (2003) 62: p. 316-330, Published online May 21, 2003.
Hubertus Haas, et al., The *Aspergillus nidulans* GATA Factor SREA Is Involved in Regulation of Siderophore Biosynthesis and Control of Iron Uptake, The Journal of Biological Chemistry, vol. 274, No. 8, Issue of Feb. 19, p. 4613-4619, 1999, Printed in U.S.A., 1999.
Hubertus Haas, et al., Characterization of the *Aspergillus nidulans* transporters for the siderophores enterobactin and triacetylfusarinine C, Biochem. J. (2003) 371, p. 505-513.
Harald Oberegger, et al., SREA is involved in regulation of siderophore biosynthesis, utilization and uptake in *Aspergillus nidulans*, Molecular Microbiology (2001) 41(5), p. 1077-1089.
Harald Oberegger, et al., Regulation of freA, acoA, IysF, and cycA Expression by Iron Availability in *Aspergillus nidulans*, Applied and Environmental Mcirobiology, Nov. 2002, p. 5769-5772, vol. 68, No. 11.
H. Oberegger, et al., Identification of members of the *Aspergillus nidulans* SREA regulon: genes involved in siderophore biosynthesis and utilization, Biometals 2002, Third International Biometals Symposium, p. 781-783.

(Continued)

*Primary Examiner*—Robert B Mondesi
*Assistant Examiner*—Brian J Gangle
(74) *Attorney, Agent, or Firm*—Oyen Wiggs Green & Mutala LLP

(57) ABSTRACT

This application relates to the production and characterization of a mutant strain of *Aspergillus fumigatus*. The application also relates to a method for inhibiting siderophore biosynthesis in *Aspergillus fumigatus* and an assay for identifying drug candidates or other agents having potential inhibitory activity. The method may comprise, for example, the step of inhibiting an enzyme catalyzing siderophore biosynthesis, such as L-ornithine $N^5$-oxygenase. In one embodiment the siderophore is a hydroxamate siderophore, such as N'N"N'"-triacetylfusarinine C (TAF) or ferricrocin. A method of preventing or treating fungal infections in a patient is also described comprising administering to the patient an agent suitable for inhibiting fungal secretion of siderophores. The method is particularly useful for immunocompromised patients susceptible to fungal infections caused by *Aspergillus fumigatus*, such as pulmonary aspergillosis. The invention also relates to diagnostic methods for detecting a biomarker indicative of likely *A fumigatus* infection in vivo, such as serum presence of TAF.

6 Claims, 20 Drawing Sheets

OTHER PUBLICATIONS

Harald Oberegger, et al., 4'-Phosphopantetheinyl transferase-encoding npgA is essential for siderophore biosynthesis in *Aspergillus nidulans*, Research Article, Current Genetics, Eukaryotes with Emphasis on Yeasts, Fungi, Protists, Cell Organelles, published online Sep. 24, 2003.

Shinichi Oide, et al., NPS6, Encoding a Nonribosomal Peptide Synthetase Involved in Siderophore-Mediated Iron Metabolism, Is a Conserved Virulence Determinant of Plant Pathogenic Ascomycetes, The Plant Cell, Vo. 18, p. 2836-2853, Oct. 2006.

Markus Schrettl, et al., Siderophore Biosynthesis But Not Reductive Iron Assimilation Is Essential for *Aspergillus fumigatus* Virulence, Brief Definitive Report, The Journal of Experimental Medicine, p. 1213-1219, vol. 200, No. 9, Nov. 1, 2004.

Anna H. T. Gifford, et al., Serum Stimulates Growth of a Proteinase Secretion by *Aspergillus fumigatus*, Infection and Immunity, Jan. 2002, p. 19-26.

A.H.T. Hissen, et al., Site-specific rate constants for iron acquisition from transferrin by the *Aspergillus fumigatus* siderophores N', N'', N''-triacetylfusarinine C and ferricrocin, Original Article, J Biol Inorg Chem (2005) 10: p. 211-220, Published online Mar. 16, 2005.

A.H.T. Hissen, et al., Survival of *Aspergillus fumigatus* in Serum Involves Removal of Iron from Transferrin: the Role of Siderophores, Infection and Immunity, Mar. 2004, p. 1402-1408, Mar. 2004, p. 1402-1408, vol. 72, No. 3.

Anna H. T. Hissen, et al., The *Aspergillus fumigatus* Siderophore Biosynthetic Gene sidA, Encoding L-Ornithine N5-Oxygenase, Is Required for Virulence, Infection and Immunity, Sep. 2005, p. 5493-5503, vol. 73, No. 9.

Julie A. Wasylnka, et al., Uptake of *Aspergillus fumigatus* Conidia by Phagocytic and Nonphagocytic Cells in Vitro: Quantitation Using Strains Expressing Green Fluorescent Protein, Infection and Immunity, Jun. 2002, p. 3156-3163 vol. 70, No. 6.

Julie A. Wasylnka, et al., *Aspergillus fumigatus* conidia survive and germinate in acidic organelles of A549 epithelial cells, Research Article, Journal of Cell Science 116, p. 1579-1587.

J. A. Wasylinka, et al., Intracellular and extracellular growth of *Aspergillus fumigatus*, Medical Mycology Supplement I 2005, 43, p. S27-S30.

Anna Gifford, et al., The role of siderophores in virulence of *Aspergillus fumigatus*, Presented as a poster at the Jun. 20-23, 2004 meeting of the Canadian Society for Microbiologists, Edmonton AB.

Gifford, Aht, et al., Iron Acquisition from serum proteins by *Aspergillus fumigatus*, Presented as a poster at the American Society for Microbiology Annual Meeting, Salt Lake City, May 19-23, 2002.

Anna H.T. Gifford et al., Distruption of siderophore biosynthesis in *Aspergillus fumigatus*, Presented as a poster at the American Society for Microbiology North West Chapter meeting, Aug. 2003.

* cited by examiner

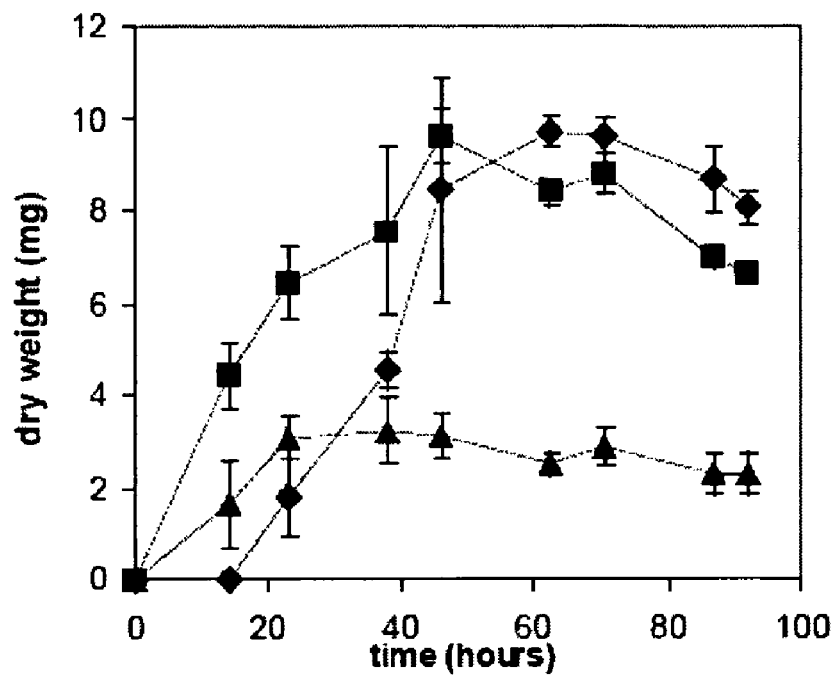
A
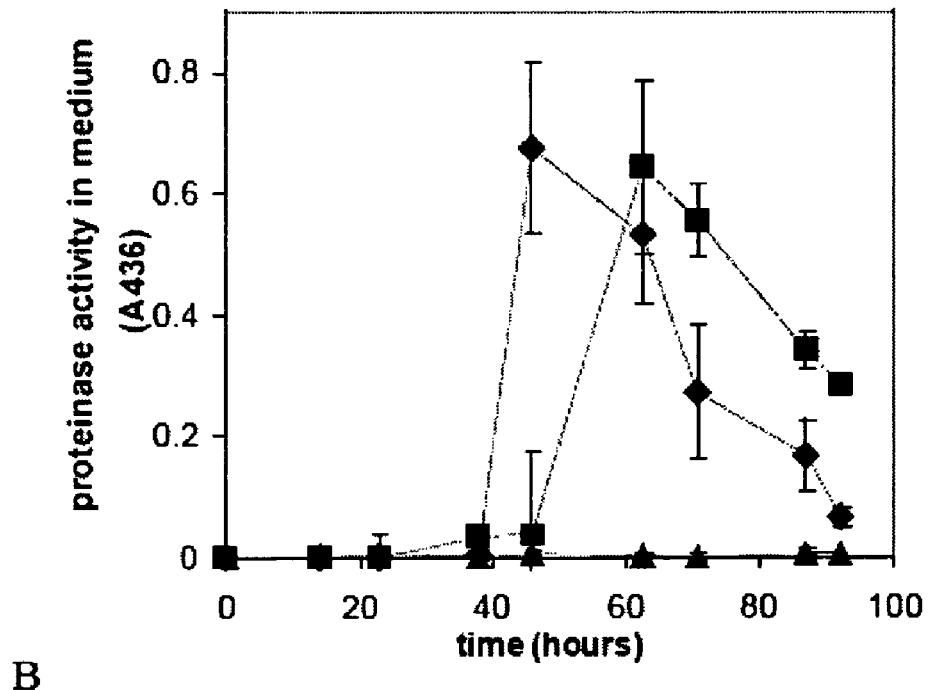
B
FIGURE 1

1  2  3  4  5
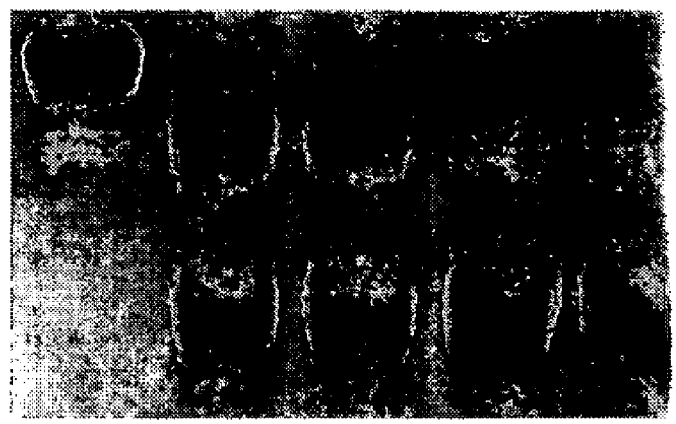
ferrichrome
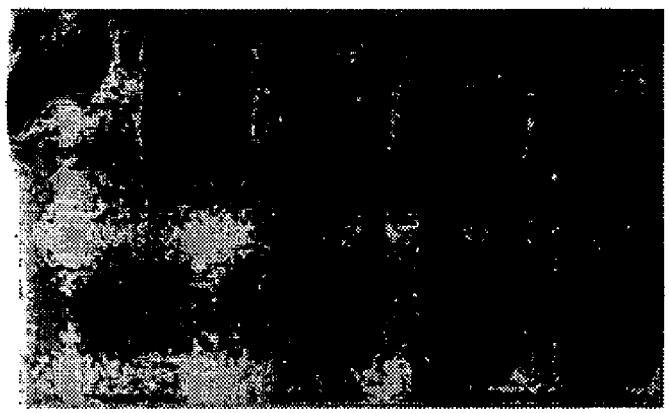
fraction 4
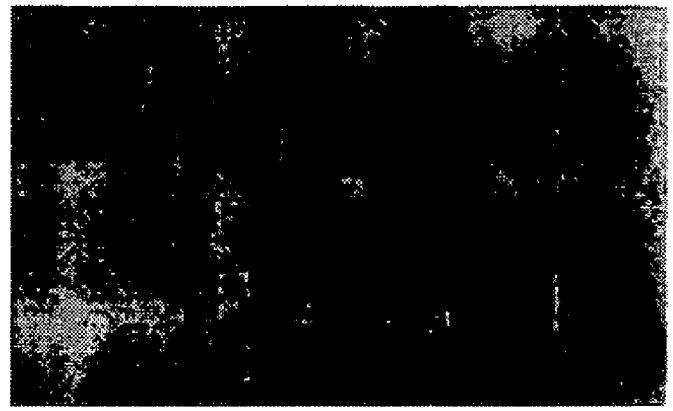
fraction 3
FIGURE 11

```
A.fumigatus    1   MESVERKSESSYLGMPNMQPECRLSLD-PPRLRSTPQDELHDLLCVGFGPASLAIAIALH
A.nidulans     1   MEPLQRKSEIDRCSYRKMPLAQQR----TQRLKETSPEELHDLICVGFGPASLAIAIALH
A.oryzae       1   MEPVERKLEIGSRSYSKMPLTQQRSSGEPPRLKATPRDELHDLLCVGFGPASLAIAIALH A.fumigatus   60   DALDPRLNKSASNIHAQPKICFLERQKQFAWHSGMLVPG3KMQISFIKDLATLRDPRSSF
A.nidulans    57   DALDPCLNKQAPTSGWQPKVRFLERQKQFAWHSGMLVFGSRMQISFIKDLATLRDPRSSF
A.oryzae      61   DALDPCLNKTP-NSNWQPKVCFLERQKQFAWHSGMLVPGSKMQISFIKDLAT MRDPRSSF A.fumigatus  120   TFLNYLHQKGRLIHFTNLSTFLPAR EFEDYMRWCAQQFSDVV AYGEEVVEVIPGKSDPS
A.nidulans   117   TFLNYLHQKDRLIHFTNLSTFLPARMEFEDYMRWCA NQFSDVVTYGEEVIEVIPGKSSPD
A.oryzae     120   TFLNYLHQKDRLIHFTNLSTFLPARMEFEDYMRWCAQ RFAHVVSYGEEVIEVIPGKTNPS A.fumigatus  180   SSVVDFFTVRSRNVETGEISAR RTRKVVIAEGGTAKMESGLPQDPRIHHSSKYCTTLPAL
A.nidulans   177   SEVVDYFTVLSRNVETGEIS SRSARKVVLALGGTAKLPAELPQDPRIMHSSKYCT LFNL
A.oryzae     180   STLVDFFTVKSRNVETGEISAR MARKVVVALGGTAKLPKELPQDPRIMHSSKYCTTLPA M A.fumigatus  240   LKDKSKPYNIAVLGSGQSAAEIFHDLQKRYPNSRTTLIMRD SAMRPSDDSPFVNE IFNPE
A.nidulans   237   LKDNNEPYNIAVLGSGQSAAEIFHDLQKRYPNSRT SLIMRDTAMRPSDDSPFVNEVFNPE
A.oryzae     240   LKDSREAYNIAVLGSGQSAAEIFHDLQKRYPNS RTTLIMRDTAMRPSDDSPFVNEVFNPE A.fumigatus  300   RVDKFYSQSAAERQRSLLADKATNYSVVRLELIEEIYNDMYLQRVKNPDETQWQHRILP  E
A.nidulans   297   RTDKFYNLSAAERERSLKADKATNYSVVRLELIEEIY HDMYLQRVKNPDETQWQHRILP S
A.oryzae     300   RVDKFESLSSAERQRSLLADKATNYSVVRLELIE QIFNDMYLQRVCNPDETQWQHRILP G A.fumigatus  360   RKITRVEH HGPQSRMRIHLKS SKPFSEGAANIVKETLEVDALMVATGYNRNAHE RLLSKV
A.nidulans   357   RKITRVEHYGP NKRMPVHVRAVKDGRDSLIGDGKEVLEVDALMVATGYNRNAHEQLLSKV
A.oryzae     360   RKITRVEHYGP ERRMRLHVRAVKDEKDSLVGNGKETLEVDALMVATGYNRNAHEQLL KNV A.fumigatus  420   QHLRPEGQDQWKHRDYRVEMDPSKVSSEAGIWLQGCNE FTHGLSDSLLSVLA VRGGEMV
A.nidulans   417   CYLRPATQDRWTPSRDYRVDLLRSKVSACAGIWLQGSNEQTHGLSDSLLSVL ATRGGEMV
A.oryzae     420   QHLRPAGQENWTPNREYRVELDPSKV NACAGIWLQGCNEQTHGLSDSLLS TLASRSGEMV A.fumigatus  480   CSIFGEQLE KAAVQGEQL-RAML
A.nidulans   477   E SIFGEQLE SAAVPDT RF-RAML
A.oryzae     480   NSIFGGEFAGTTVPDTTHIRAML
```

FIGURE 14

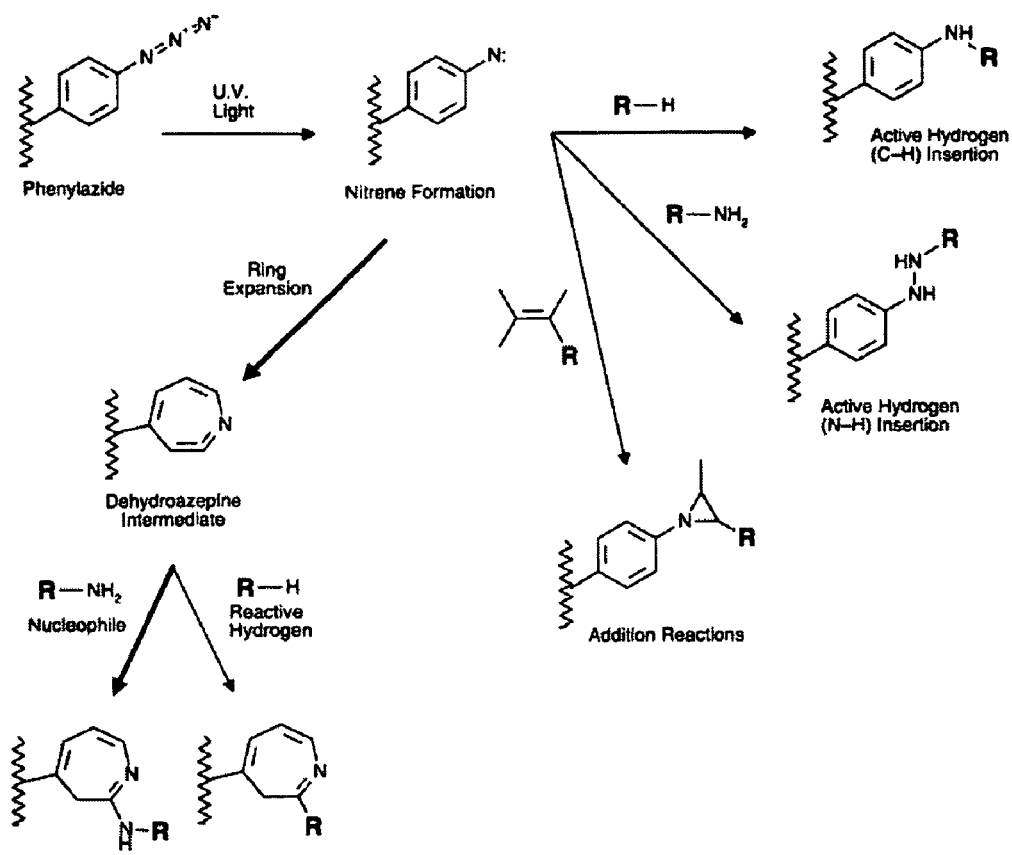

Figure 170 Photolyzing a phenyl azide group with UV light results in the formation of a short-lived nitrene. Nitrenes may undergo a number of reactions, including insertion into active carbon—hydrogen or nitrogen—hydrogen bonds and addition to points of unsaturation in carbon chains. The most likely route of reaction, however, is to ring-expand to a dehydroazepine intermediate. This group is highly reactive toward nucleophiles, especially amines.

FIGURE 29

PRODUCTION OF MUTANT STRAIN OF *ASPERGILLUS FUMIGATUS*, METHOD OF ASSAY FOR INHIBITING SIDEROPHORE BIOSYNTHESIS AND DIAGNOSTIC METHOD FOR DETECTING LIKELY *ASPERGILLUS FUMIGATUS* INFECTION

RELATED APPLICATIONS

This application claims the benefit of U.S. provisional patent application Ser. No. 60/580,978 filed 21 Jun. 2004, which is incorporated herein by reference.

TECHNICAL FIELD

This application relates to methods for inhibiting siderophore biosynthesis and secretion in *Aspergillus fumigatus* and assays for identifying drug candidates or other agents having potential inhibitory activity. Further, the application relates to diagnostic methods and assays for detecting patients in the early stages of *A. fumigatus* infection.

BACKGROUND

*Aspergillus fumigatus* is a potentially virulent species of filamentous fungus, particularly in immunocompromised individuals. *A. fumigatus* reproduces by producing large numbers of airborne conidia which, once inhaled by susceptible patients, can lead to life-threatening invasive aspergillosis (1). Bone marrow and solid organ transplant recipients (2), cancer patients (3), AIDS patients (4), and those with chronic granulomatous disease (5) are particularly at risk for developing invasive aspergillosis. Invasive aspergillosis can be treated with the anti-fungal drugs amphotericin B and itraconazole; however, these drugs have low rates of success. Even with prophylaxis and treatment with amphotericin B, mortality rates average 65% for pulmonary aspergillosis and approach 100% if the disease spreads to the central nervous system (6). The basic virulence factors that allow some *Aspergillus* species to establish invasive infections remain unclear (1, 7). Approximately 90% of invasive aspergillosis cases are caused by one species, *Aspergillus fumigatus*. The remainder are caused primarily by *Aspergillus nidulans*, *Aspergillus flavus*, *Aspergillus niger* and *Aspergillus terreus* (8).

The number of patients undergoing solid-organ transplantation or hematopoietic stem cell transplant (HSCT) has increased rapidly in the last two decades. Worldwide, 15,000 allogeneic and 25,000 autologous stem cell transplants were performed (9). In the US, an average of 23,000 were performed annually between 1998-2002, a 20% increase over the preceding 5 year period (United Network of Organ Sharing). Invasive aspergillosis is now a leading cause of death in leukemia and bone marrow transplant units; *Aspergillus* infections have been reported in 2-26% of hemopoietic stem cell transplant patients, and 1-15% of organ transplant recipients. An estimated 9.3-16.9% of all deaths in transplant recipients in the first year are attributable to invasive aspergillosis (10). Because of the difficulty in diagnosing invasive aspergillosis, and the high mortality rate of the infection, new diagnostic and treatment methods are urgently needed.

As described below, the inventors have determined that the virulence of *A. fumigatus* appears to be related to the secretion of siderophores, such as N',N'',N'''-triacetylfusarinine C (TAF) and ferricrocin. Siderophores are microbial iron chelates synthesized by some fungi and bacteria in response to low iron availability in the environment, such as serum. The inventors have discovered that TAF and ferricrocin appear to be able to remove iron from human serum iron-binding proteins, such as transferrin.

In light of this discovery, the need has arisen for methods for preventing or treating fungal infections caused by by *A. fumigatus* or other *Aspergillus* species by inhibiting secretion of siderophores. Since siderophore biosynthesis pathways are absent in human cells, the pathways present attractive new targets for antimicrobial chemotherapy. The first committed step in siderophore biosynthesis is catalyzed by the enzyme L-ornithine $N^5$-oxygenase. A subsequent step in siderophore biosynthesis is catalyzed by non-ribosomal peptide synthetases. The invention therefore includes methods for identifying candidate drugs capable of inhibiting ornithine oxygenase, inhibiting other enzymes involved in siderophore biosynthesis such as non-ribosomal peptide synthetases, inhibiting the secretion of siderophores, or interfering with the formation of the siderophore-iron complex.

The need has also arisen for a diagnostic test using a biomarker indicative of likely *A. fumigatus* infection. Invasive aspergillosis is difficult to diagnose by radiological means. Radiological findings are often varied and non-specific, including segmental and multilobar consolidation, perihilar infiltrates, multiple small nodules, peripheral nodular masses and pleural effusions (11). Additionally, definitive diagnosis requires histopathologic evidence of deep tissue invasion or a positive culture from a sterile site. However, obtaining tissue from these thrombocytopenic patients is dangerous, and blood/CSF cultures are seldom positive. *fumigatus* can be cultured from bronchoalveolar lavage from infected patients. However, this is not a consistent finding, and often does not occur until late in infection. Genomic DNA can be detected in blood using PCR methods. Such methods are specific but are only semi-quantitative and are expensive. The simplest and cheapest method currently available is the PLATELIA™ *Aspergillus* ELISA test from Bio-Rad. This measures circulating galactomannan, a carbohydrate shed from the fungal cell wall. The specificity of the assay is very good (85%); however, the sensitivity of the assay is quite variable (29-100%). In addition, false positive reactions have been shown to occur, especially in children (83%) (12). Therefore new diagnostic methods are urgently needed.

SUMMARY OF INVENTION

In accordance with the invention, a method of inhibiting growth of *Aspergillus fumigatus* is described. The method comprises inhibiting siderophore biosynthesis or siderophore iron-binding capacity. The method may comprise, for example, the step of inhibiting an enzyme catalyzing siderophore biosynthesis, such as L-ornithine $N^5$-oxygenase. In one embodiment the siderophore is a hydroxamate siderophore, such as N'N''N'''-triacetylfusarinine C (TAF) or ferricrocin.

A method of preventing or treating fungal infections in a patient is also described comprising administering to the patient an agent suitable for inhibiting fungal secretion of siderophores. The method may involve inhibiting siderophore biosynthesis, such as by inhibiting the activity of an enzyme catalyzing the biosynthesis, such as L-ornithine $N^5$-oxygenase. The fungal infection may be invasive aspergillosis, which is of increased prevalence in immunocompromised patients.

An assay for screening for agents having the ability to inhibit siderophore production or siderophore iron-binding capacity in *Aspergillus fumigatus* is also described as are mutant strains of *Aspergillus fumigatus* which are siderophore-secretion deficient. In one mutant strain the sidA gene has been deleted or disrupted. Modified fungal cells having the sidA gene deleted or disrupted are also within the scope of the invention. The invention also relates to an isolated gene having the nucleotide sequence of the sidA gene and sequences homologous thereto.

The invention also relates to a diagnostic method and assay for detecting likely *A. fumigatus* infection in a subject.

BRIEF DESCRIPTION OF DRAWINGS

In drawings which illustrate embodiments of the invention, but which should not be construed as restricting the spirit or scope of the invention in any way, FIG. 1 shows a growth curve and proteinase secretion for *A. fumigatus* in 10 ml MEM with or without 10% FBS or 10% human serum. *A. fumigatus* was cultured in MEM alone (triangles), MEM containing 10% FBS (squares) or MEM containing 10% human serum (diamonds) as described below. Flasks were removed from incubation at several time points and the contents of the whole culture flasks were filtered through MIRACLOTH™ and mycelia transferred to pre-weighed microcentrifuge tubes. (A) Tubes were lyophilized, overnight and weighed to determine dry weights. (B) Proteinase secretion was measured by the azocasein assay as described below. The data shown are the mean±standard deviations for three replicates and are representative of three independent experiments.

FIG. 11 shows the removal of iron from holotransferrin by *A. fumigatus* siderophores. Purified desferri-siderophores and commercially available ferrichrome were serially diluted to final concentrations of 2.5 mM, 250 μM, 25 μM, 2.5 μM and 250 nM (lanes 1-5, respectively). Siderophores were incubated with 12.5 μM human holo-Tf at 37 degrees for 16 hours. Iron saturation of transferrin was assessed by urea-PAGE (13). Fraction 3 has been identified as N',N'',N'''-triacetylfusarinine C (also called triacetylfusigen).

FIG. 14 shows an alignment of the *A. fumigatus* SidA, *A. nidulans* SidA and *A. oryzae* Dff1 amino acid sequences (SEQ ID NO:17, SEQ ID NO:18 and SEQ ID NO:19, respectively). The amino acid sequence of *A. fumigatus* SidA (SEQ ID NO:17) was predicted using GlimmerM from the 25 Institute for Genomic Research (TIGR) trained for *A. fumigatus*. Multiple pairwise alignment was performed by ClustalW (15) and the output generated by Boxshade 3.21. Black and grey boxes represent identical and similar residues, respectively.

FIG. 29 shows reactions of aryl azide photoreactive crosslinking agents with target molecules (R). The target molecule is TAF. Figure from G T Hermanson (1996) (16).

DESCRIPTION

Figure 2:
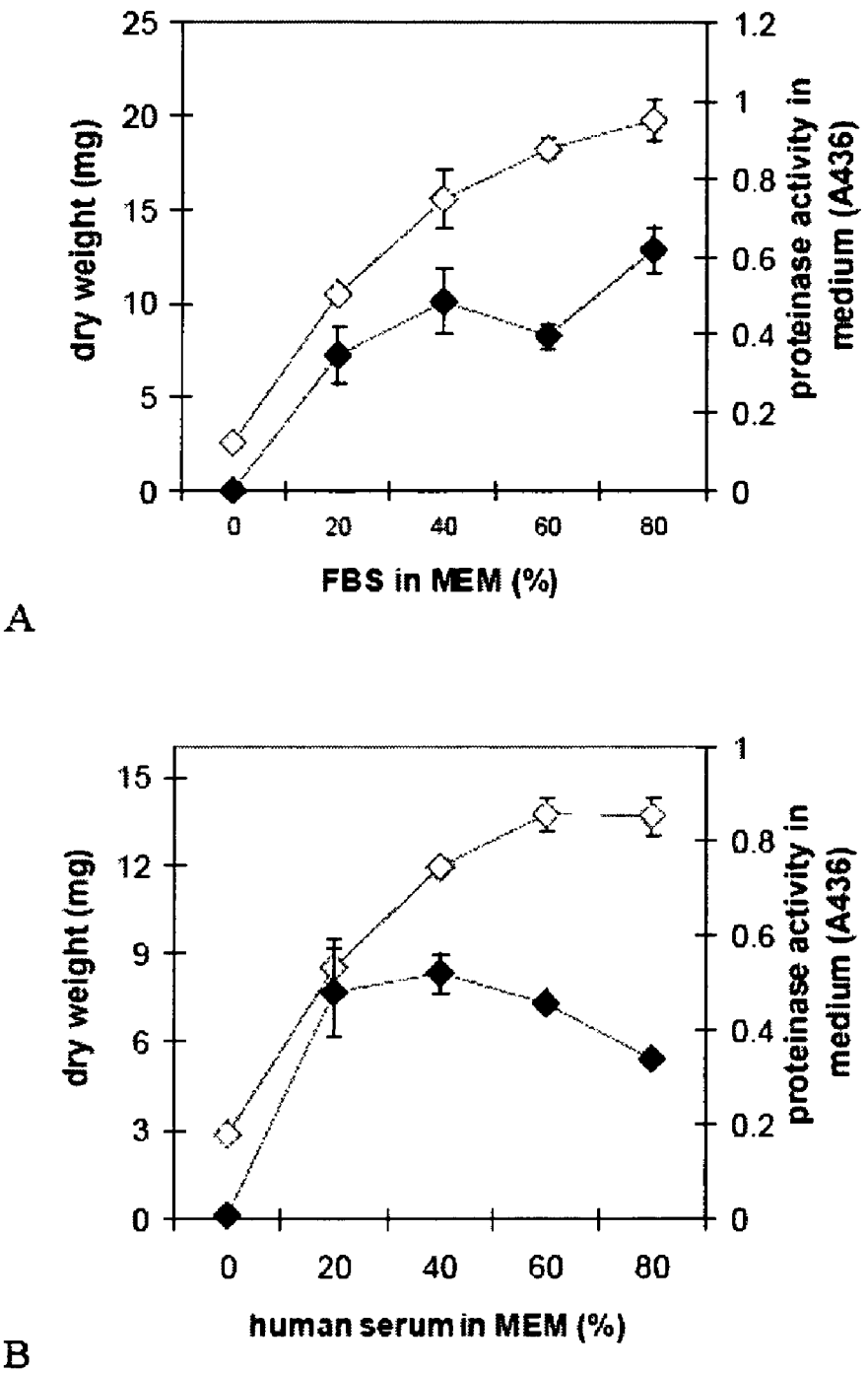
FIG. 2 shows the growth of *A. fumigatus* in MEM containing high concentrations of fetal bovine serum or human serum. *A. fumigatus* ($10^6$ conidia/ml) was cultured in 5 ml MEM containing fetal bovine serum (A) or human serum (B) concentrations ranging from 0 to 80%. The MEM concentration was held constant. Flasks (25 ml) were incubated for 50 hours at 37° C. and 150 rpm. Dry weights were measured and azocasein assays performed as described below. The data shown are the mean[1] standard deviations for three replicates. (A) is representative of three independent experiments and (B) is representative of two independent experiments. Open symbols show dry weights, while black symbols show proteinase activity.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense. Without limiting the scope of the invention, examples have been included which are embodiments of the invention.

*Aspergillus fumigatus* is an opportunistic fungal pathogen and is a leading cause of mould infections worldwide. As explained above, *A. fumigatus* can cause life-threatening invasive aspergillosis and is particularly a serious problem in immunocompromised populations. While some diagnostic tests for detecting the presence of *A. fumigatus* are known, improved diagnostic and therapeutic methods are urgently needed.

As described in Example 1.0 below, the inventors have determined that the survival of *A. fumigatus* in serum depends upon the secretion of siderophores. Siderophores are microbial iron chelates which are synthesized by some fungi and bacteria in response to low iron availability in the environment, such as in serum. Siderophores appear to be able to remove iron from serum iron-binding proteins, such as transferrin. Although *A. fumigatus* secretes at least five different types of hydroxamate siderophores, the most common appear to be N'N"N'''triacetylfusarinine C (TAF) and ferricrocin. The inventors have determined that more than 90% of the siderophores secreted by *A. fumigatus* comprises TAF.

As described in Example 2.0 below, both TAF and ferricrocin are synthesized via the same biochemical pathway. The first committed step in siderophore biosynthesis in *A. fumigatus* involves N-hydroxylation at the terminal amino group of ornithine which results in the formation of a N—O bond. This biosynthetic step is catalysed by an L-ornithine $N^5$-oxygenase. The inventors have identified the specific gene in *A. fumigatus*, termed sidA, which encodes this enzyme. Siderophore biosynthetic pathways are absent in human cells and therefore these pathways represent potential new targets for antimicrobial chemotherapy.

As described in Example 3.0 below, the inventors have created a stable mutant strain of *A. fumigatus* by deleting the sidA gene. The mutant strain is referred herein as the ΔsidA strain. The ΔsidA strain is unable to synthesize siderophores such as TAF and ferricrocin. Growth of the ΔsidA mutant strain is the same as the wild type strain in rich media. However, ΔsidA was unable to grow in low iron defined media or media containing 10% human serum unless supplemented by TAF or ferricrocin. No significant differences in ferric reduction activities were observed in the wild type and mutant strains, indicating that the blocked siderophore secretion did not result in upregulation of this pathway. Unlike the wild type strain, ΔsidA was unable to remove iron from human transferrin. As described in Example 3.0, a rescued strain (i.e. ΔsidA+sidA) was also constructed which produced siderophores and had the same growth as the wild type strain on iron-limited media.

The inventors have created a mouse model of invasive aspergillosis as described in Example 4.0 below. Unlike the wild type and rescued strains, the ΔsidA mutant strain was avirulent in the animal model, indicating that sidA is necessary for *A. fumigatus* virulence.

Example 5.0 below describes various embodiments of an assay designed for identifying potential siderophore secretion inhibitors, such as by screening for candidate agents capable of inhibiting L-ornithine $N^5$-oxygenase or other enzymes catalyzing steps in the siderophore biosynthetic pathway.

In Example 6.0 below a diagnostic test for detecting a biomarker indicative of likely *A. fumigatus* infection is described. In one embodiment, the assay detects the presence of TAF in serum.

EXAMPLES

The following examples will further illustrate the invention in greater detail, although it will be appreciated that the invention is not limited to the specific examples.

Example 1.0

Survival of *A. fumigatus* in Serum Depends Upon the Secretion of Siderophores

As described in Applicant's U.S. provisional patent application 60/580,978 filed 21 Jun. 2004 (the '978 application), which is incorporated herein by reference in its entirety, mammalian serum is inhibitory to the growth of many microbes, including some of the most common fungal pathogens. In extracellular fluids, iron-chelating proteins maintain the free iron concentration at about $10^{-18}$ M (17). This concentration is too low to support the growth of many microbes, including most pathogenic fungi. During infections, nonspecific host defenses decrease the level of free iron even further by increasing ferritin synthesis and releasing lactoferrin from neutrophils.

The inhibitory action of serum is thought to be due to its ability to chelate iron, depriving invading pathogens of this essential nutrient (18). In particular, transferrin in human serum binds iron and makes it unavailable to microorganisms. Transferrin in human serum is inhibitory to the growth of most pathogenic fungi. Iron is required by almost all organisms for the catalysis of DNA synthesis and for enzymes involved in electron transport and energy metabolism (19). There is some indirect evidence that iron plays a role in the virulence of fungi.

The inventors have discovered that serum stimulates the growth of *A. fumigatus*, and that iron is a factor in serum that stimulates the growth of *A. fumigatus*. In particular, the inventors have demonstrated that, unlike most other common fungal pathogens, neither fetal bovine serum nor human serum inhibits the growth of *A. fumigatus*, but both in fact stimulate growth when present in concentrations up to 80%.

Example 1.1

Strains and Growth Conditions

To investigate the effects of serum on *A. fumigatus*, strain ATCC 13073, originally isolated from a human pulmonary lesion, was obtained from the American Type Culture Collection. *A. fumigatus* was maintained on YM slants (0.3% malt extract, 0.3% yeast extract, 0.5% peptone and 0.5% glucose) at 4° C. *A. fumigatus* was cultured on YM plates at 28° C. for 5-10 days, until fully conidiated. Conidia were harvested by flooding the culture plate with phosphate buffered saline (PBS) containing 0.05% Tween-20, and swabbing with a sterile cotton swab. The conidia were then vortexed, filtered through a plug of sterile glass wool to remove hyphae, and resuspended in PBS. Concentrations of conidia were determined by counting in a hemacytometer.

For most experiments, *A. fumigatus* was cultured in minimal essential medium (MEM) (Life Technologies, Burlington, Ontario) containing the stated concentration of serum or other medium components in a total volume of 5 ml in 25 ml culture flasks. MEM contains 1 mg/ml glucose, amino acids, vitamins, and salts (20). Though it does not contain added iron, trace levels present in the MEM were sufficient to permit some growth of *A. fumigatus*. For iron-depletion experiments, glassware was treated overnight in 1 mM EDTA, followed by 2 hours in 0.5 M HCl, then rinsed six times with deionized water. Trace levels of iron were removed from MEM by stirring overnight with 6% w/v Chelex 100 (Sigma, Oakville, Ontario). After Chelex treatment, 2 g/L $CaCl_2$ and 0.98 g/L $MgSO_4$ were added to MEM. Media containing high serum concentrations were prepared using a 10× stock of MEM to ensure that the MEM concentration remained constant.

Conidia were added to media at a final concentration of $1\times10^6$/ml, and flasks were incubated at 36° C. and 150 rpm. Dry weights were measured by filtering the entire contents of each flask through MIRACLOTH™ (Calbiochem, La Jolla, Calif.) and rinsing thoroughly with $dH_2O$ to remove all traces of culture medium. Mycelia were then transferred to pre-weighed microcentrifuge tubes, lyophilized overnight and weighed.

Fetal bovine serum was obtained from Life Technologies (Burlington, Ontario). Human serum (male) was obtained from Sigma (Oakville, Ontario). All sera were stored in 10 ml or 100 ml aliquots at −20° C. until use. Serum was thawed in a 37° C. waterbath and processed as follows. Serum was heat-treated in a Braun Thermomix 1441 11 L waterbath, for 30 minutes at the specified temperature (56 or 66° C.), or treated at 100° C. in a boiling water bath for 30 minutes. Serum was separated into high and low molecular weight fractions by centrifugation at 3000×g for 1 hour at 0° C. through an Ultrafree 10,000 molecular weight cutoff filter (Millipore, Bedford, Mass.). The retained material was dialyzed against three changes of water at 4° C. through a membrane with 10,000-12,000 molecular weight cut-off to thoroughly remove low molecular weight components. Data analysis for these experiments was performed using the Student.s t-test or analysis of variance followed by a Tukey multiple comparison procedure.

Example 1.2

Serum Stimulates Growth of *A. fumigatus*

The incubation of *A. fumigatus* in MEM containing 10% fetal bovine serum (FBS) resulted in a faster rate of growth and a higher total biomass as compared to the same medium lacking serum (FIG. 1A). Growth was slightly delayed in media containing human serum, but the same maximum growth levels were reached. In serum-containing media, cultures reached stationary phase after roughly 60 hours of incubation, and the fungal dry weight in the presence of 10% serum was approximately four-fold greater than that of fungi cultured in serum-free MEM.

The slight delay of growth of *A. fumigatus* in medium containing human serum as compared with FBS may be caused by a more limited iron availability in human serum. Though fetal and adult sera contain roughly equal transferrin concentrations, fetal transferrin is more highly iron saturated. Transferrin in FBS is present at 1.2 to 1.8 mg/ml and is 55-92% iron saturated (21), while transferrin in human serum is usually 25-35% saturated (22). FBS therefore has less potential to chelate free iron in the medium, which could explain its inability to inhibit growth of pathogens such as *C. neoformans*.

Previous work with *Rhizopus rhizopodiformis* showed a stimulation of fungal growth by human serum at concentrations up to 20%, but inhibition of growth at all higher human serum concentrations (23). Therefore, the ability of *A. fumigatus* to grow in higher concentrations of fetal bovine and human sera was also evaluated. The growth of *A. fumigatus* was found to increase with increasing serum concentrations, and no evidence of growth inhibition by FBS was observed at concentrations up to 80% (FIG. 2A). Human serum also supported increased growth of *A. fumigatus* at concentrations up to 80% (FIG. 2B). To the knowledge of the inventors, *A. fumigatus* is the only fungal pathogen able to tolerate and thrive in such high serum concentrations.

Proteinase secretion by *A. fumigatus* was monitored by using azocasein hydrolysis. Proteinase secretion was monitored because this represents a potential mechanism for the virulence of *A. fumigatus*. However, as discussed below, the inventors have demonstrated that proteinase secretion is likely not the primary mechanism by which *A. fumigatus* obtains iron from serum. Proteinase secretion was quantified using the azocasein assay as outlined by Reichard et al. (58). Azocasein (Sigma, Oakville, Ontario) was dissolved at 5 mg/ml in assay buffer containing 50 mM Tris, pH 7.5, 0.2M NaCl, 5 mM CaCl2, 0.05% Brij 35, and 0.01% sodium azide. Media from *Aspergillus* cultures were removed at various time points and centrifuged to pellet cells. Azocasein solution (400µ) was mixed with 100µ supernatant from *Aspergillus* cultures and incubated in a 37° C. waterbath for 90 minutes. Reactions were stopped by addition of 150 µl 20% TCA, and allowed to stand at ambient temperature for 30 minutes. Tubes were then centrifuged for 3 minutes at 8,000 g and 500 µl supernatant was added to 500 µl 1M NaOH. The absorbance of released azo dye was read on a spectrophotometer at 436 nm. As shown in FIGS. 1B, 2A and 2B, proteinase secretion by *A. fumigatus* also increased steadily with increasing FBS concentrations. Human serum also stimulated proteinase secretion, but the effect reached a maximum at 40% serum and declined slightly at higher concentrations.

Figure 3:
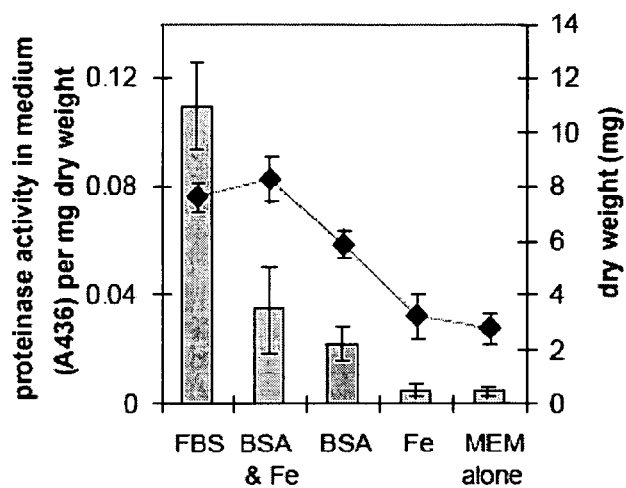
FIG. 3 shows proteinase secretion and relative growth of *A. fumigatus* in MEM containing BSA and iron. MEM (5 ml) containing 10% FBS, 8 mg/ml BSA, 100 μM $FeCl_3$, 8 mg/ml BSA and 100 μM $FeCl_3$, or MEM alone were inoculated with $10^6$ *A. fumigatus* conidia per ml and incubated at 37° C. and 150 rpm. Proteinase secretion per mg dry weight (bars) and dry weight (diamonds) were measured as described in the specification. Data shown are means of five independent experiments[1] standard deviations. Statistical analysis of the growth data revealed that FBS and BSA plus iron were both significantly greater from BSA alone (p<0.01) which in turn, was significantly greater than iron plus MEM and MEM alone (p<0.01). For the proteinase secretion data, FBS was significantly greater than BSA and BSA plus iron, and these two groups were different from MEM plus iron and MEM alone (p<0.01).

Proteinase secretion in *A. fumigatus* can be induced by the presence of protein or protein hydrolysate in the medium (24), thus the inventors tested the ability of one serum protein, bovine serum albumin (BSA) to stimulate growth and proteinase secretion. A BSA stock solution of 80 mg/ml, roughly equivalent to the protein concentration in serum, was prepared and added to the culture medium to give a final concentration of 8 mg/ml. Addition of BSA to MEM significantly stimulated the growth of *A. fumigatus*, though growth was still only 80% of that found in the presence of FBS (FIG. 3). Proteinase secretion per mg dry weight was significantly increased when BSA was added to MEM. Nevertheless, the levels of proteinase secretion in BSA were only 20% of those observed when cultures were grown in 10% FBS (FIG. 3).

Although serum does appear to induce an increase in proteinase secretion by *A. fumigatus*, proteolysis is not the primary mechanism of iron acquisition by *A. fumigatus* under conditions of low free iron concentrations, as described further below.

Example 1.3

Protein-Bound Iron is a Factor in Serum that Stimulates Growth of *A. fumigatus*

A key mechanism by which *A. fumigatus* is able to grow in serum is the ability to obtain iron from proteins in human serum. In particular, the stimulation of growth of *A. fumigatus* by serum can be mimicked by the addition of BSA and iron to minimal medium. Although the addition of BSA to minimal medium increases the growth of *A. fumigatus*, only the addition of BSA plus iron achieves the same levels of growth stimulation as serum. Addition of only iron to minimal media does not stimulate the growth of *A. fumigatus*; therefore, iron is not growth-limiting for *A. fumigatus* grown in MEM. Moreover, iron is not limiting for the growth of *A. fumigatus* in minimal media containing 10% FBS, nor does removal of up to 50% of the iron from human serum inhibit the growth of *A. fumigatus*. The factor in serum which stimulates the growth of *A. fumigatus* is a molecule or molecules with a molecular weight larger than 10 kDa, which is consistent with protein-bound iron. Thus, the unique ability of *A. fumigatus* to grown in the presence of serum appears to be related to its ability to obtain iron from proteins in serum.

As discussed further below, the mechanism by which *A. fumigatus* is able to grow in serum is by accessing iron in serum via siderophores, and the combination of available iron and protein in serum permits abundant growth of *A. fumigatus*. It should be noted that in the course of these experiments, iron was not released by changes in pH in the batch cultures because the pH of the culture medium remained neutral to alkaline.

Serum can be a source of iron, if a microorganism possesses a mechanism to remove iron bound to transferrin or other iron-binding proteins (25). To further investigate whether *A. fumigatus* could obtain iron from serum, iron was removed from serum as described by Wilson et al. (26). Serum was filtered through an Ultrafree 10,000 molecular weight cutoff filter (Millipore, Bedford, Mass.), and the filtrate stored at 4° C. The protein-containing fraction was lowered to pH 4.0 with 1M HCl, and EDTA was added to a final concentration of 10 mM. The fraction was dialyzed overnight against PBS containing 6% w/v Chelex 100 (Sigma, Oakville, Ontario) before being recombined with the low-molecular weight components. The iron content of the treated serum was determined by digesting the samples in boiling nitric acid, making appropriate dilutions in iron-free water and measuring free iron by atomic absorption spectrometry using a Perkin Elmer AAnalyst 100. Matrigel was obtained from Becton Dickinson Labware, Bedford, Mass.

Using atomic absorption spectrometry, the inventors found that the iron levels of the sera used were as follows: FBS was 4.7 ppm (84 μM) and human serum was 1.1 ppm (20 μM), while the level in MEM was below detection limits (0.1 ppm). The inventors therefore postulated that the presence of iron in serum might be responsible for its growth-enhancing effect on *A. fumigatus*. Addition of 100 μM $FeCl_3$ alone to MEM had no effect on either growth or proteinase secretion by *A. fumigatus*, while addition of 100 μM $FeCl_3$ and 8 mg/ml BSA together resulted in the same amount of growth as seen with 10% FBS (FIG. 3). The combination of $FeCl_3$ and BSA, while significantly improving growth, had only a small effect on proteinase secretion compared to BSA alone: levels of proteinase secretion with BSA plus iron remained at 30% of the levels found with FBS (FIG. 3).

Supplementing MEM with 100 μM $FeCl_3$ alone did not increase growth, indicating that iron levels in MEM were not growth-limiting for *A. fumigatus*. Furthermore, iron was not limiting for *A. fumigatus* in MEM plus 10% FBS because addition of 100 μM $FeCl_3$ did not result in increased growth and proteinase secretion. However, addition of BSA and 100 μM $FeCl_3$ to MEM allowed growth levels equivalent to those observed in serum-containing MEM. These results show that growth of *A. fumigatus* in media containing 8 mg/ml BSA was limited by iron availability. Since iron was not growth-limiting in media containing serum, *A. fumigatus* must be able to access the iron in serum. Dialysis of serum against water did not result in the loss of growth-promoting activity, therefore the source of iron accessed by *A. fumigatus* was likely molecules larger than 10 kDa. This molecular weight is consistent with protein-bound iron.

The inventors also attempted to remove iron from serum by treating serum with Chelex beads as described above. However, treatment of either FBS or human serum resulted in removal of only 50% of the total iron (data not shown). This level of iron was sufficient to maintain the same level of growth of *A. fumigatus* as found in untreated sera: after 66 h of incubation, the biomass of cultures with Chelex-treated human serum was $6.84^1$ 0.46 mg whereas in untreated sera, the biomass was $5.81^1$ 0.91 mg (n=3). A small effect on proteinase secretion was observed: proteinase secretion per mg dry weight from Chelex-treated human sera was $0.05^1$ 0.01, and untreated human sera was $0.07^1$ 0.01. Supplementing samples containing Chelex-treated serum with 10 μM iron restored the level of proteinase secretion to $0.07^1$ 0.01. These data indicate that removal of up to 50% of the iron present in human sera (final iron content of 10 μM) was not growth inhibitory for *A. fumigatus* but did have a small inhibitory effect on proteinase secretion by this fungus.

In summary, in this example and other examples below, the inventors have investigated the mechanism by which *A. fumigatus* obtains iron in serum-containing media. The inventors have determined that the survival of *A. fumigatus* in serum involves removal of iron from the iron-binding protein transferrin by siderophores secreted by the fungi. Siderophores are microbial iron chelates synthesized by some fungi and bacteria in response to low iron availability in the environment. In particular, the addition of holotransferrin to iron-depleted media supports the growth of *A. fumigatus*, while the addition of apotransferrin does not. This indicates that *A. fumigatus* is able to utilize holotransferrin as a source of iron.

Furthermore, proteolysis of transferrin is not the primary mechanism of iron acquisition by *A. fumigatus* in serum. The degradation of transferrin by *A. fumigatus* occurs after stationary phase has been reached, and not during active growth. In contrast, as discussed below with reference to Example 1.7, secretion of siderophores by *A. fumigatus* occurs at an early stage that coincides with active growth. The inventors have also found that *A. fumigatus* can remove iron from transferrin across a dialysis membrane. Such a finding supports the role of siderophores as the mechanism for the removal of iron from human transferrin by *A. fumigatus*.

Example 1.4

Holotransferrin but not Apotransferrin Supports the Growth of *A. fumigatus* in Iron-Depleted Medium The inventors have shown that holotransferrin but not apotransferrin supports the growth of *A. fumigatus* in iron-depleted medium. MEM was made iron limiting by the addition of the iron-chelator 2,2'-dipyridyl. A concentration of 250½M 2,2'-dipyridyl was empirically determined to be the MIC for *A. fumigatus* ATCC 13073. The addition of apotransferrin to MEM containing 2,2'-dipyridyl did not support the growth of *A. fumigatus*, whereas the addition of either 25½M holotransferrin or 50½M $FeCl_3$ to iron-limited MEM promoted statistically significant growth of *A. fumigatus* (Table 1). These data indicate that transferrin-bound iron is available to *A. fumigatus* as an iron source.

TABLE 1

Growth of *A. fumigatus* in MEM (5 ml) containing a 250 µM concentration of the iron chelator 2,2'-dipyridyl and supplemented with holotransferrin, apotransferrin, or FeCl₃.

| Iron source | Mean[1] SD mycelial dry wt after 96 h (mg) | |
| --- | --- | --- |
| None (MEM and 2,2'-dipyridyl alone) | 0.13[1] | 0.07 |
| Holotransferrin (25 µM) | 1.30[1] | 0.90[a] |
| Apotransferrin (25 µM) | 0.02[1] | 0.05 |
| FeCl₃ (50 µM) | 0.80[1] | 0.40[a] |

[a]Growth was significantly greater than that in the absence of any iron source (none) ($P < 0.05$).

Example 1.5

Transferrin Proteolysis is not the Primary Mechanism of Iron Acquisition by *A. fumigatus* in Serum The inventors have also shown that serum transferrin is not degraded during the growth of *A. fumigatus*. Like many fungi, *A. fumigatus* is a prolific producer of proteinases. Previous results obtained by Gifford et al. showed that growth in human serum, an iron-deficient medium, was accompanied by increased secretion of proteinases (27). In theory, these proteinases could degrade human transferrin and release iron, which then would be available for uptake by fungal cells. Degradation of human transferrin was therefore monitored by culturing *A. fumigatus* in MEM containing either 2.5½M purified human transferrin or 10% human serum.

Proteolytic cleavage of transferrin during the growth of *A. fumigatus* was monitored by sodium dodecyl sulfate-10% polyacrylamide gel electrophoresis (PAGE). Media were withdrawn from *A. fumigatus* cultures and electrophoresed according to the procedure of Laemmli (28). Gels were silver stained or transferred to polyvinylidene difluoride membranes (Bio-Rad), blocked with 5% bovine serum albumin, probed with a rabbit immunoglobulin G fraction of anti-human transferrin (1:1,000 dilution; Rockland Inc., Gilbertsville, Pa.), and treated with goat anti-rabbit-horseradish peroxidase. Bands were visualized by adding the substrate diaminobenzidine. Urea-PAGE was carried out as described by Wolz et al. (29). with a Protean II xi cell (Bio-Rad). Gels were stained with SYPRO orange (Molecular Probes, Eugene, Oreg.) and scanned with a Typhoon 9410 imager (Amersham).

Figure 4:
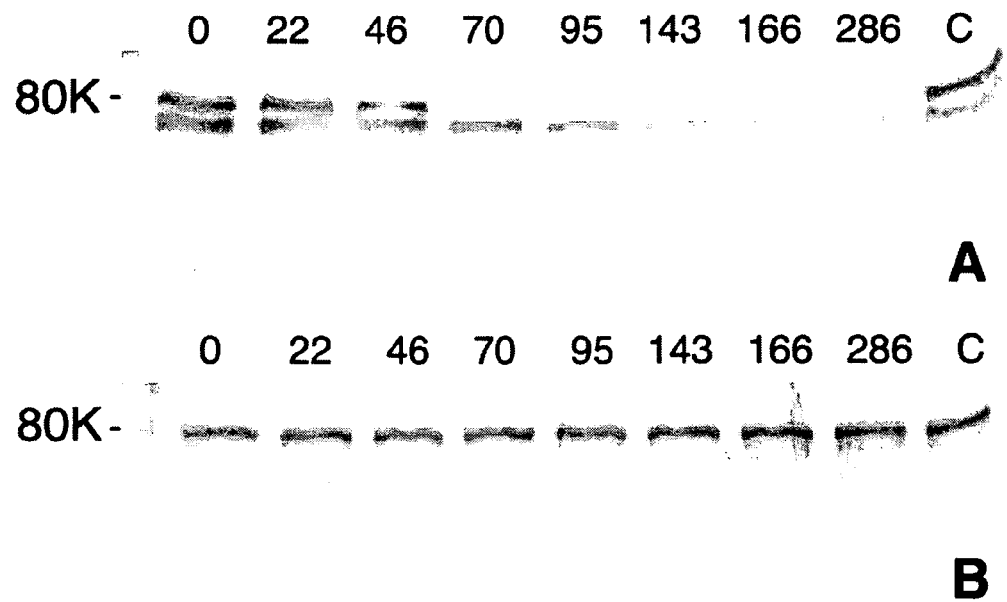
FIG. 4 shows degradation of transferrin by *A. fumigatus* in liquid cultures. *A. fumigatus* was incubated in MEM containing 10% human serum (A) or 2.5 μM holotransferrin (B). Supernatants were withdrawn from the cultures after the number of hours indicated above the lanes, and the presence of transferrin was determined by Western blotting following sodium dodecyl sulfate-PAGE. Controls (lanes C) were uninoculated samples incubated for 286 h. The band underneath transferrin in panel A is another protein that cross-reacted with the polyclonal antitransferrin antibody.

The addition of serum to MEM stimulated proteinase secretion, as evidenced by the degradation of serum transferrin beginning at 46 h of culturing. However, transferrin was stable for at least the first 22 h of incubation. There was a small decrease in the amount of transferrin at 46 h, and considerable degradation was observed at all later time points (FIG. 4). Stationary phase was reached at between 22 and 46 h of growth; therefore, serum transferrin degradation by *A. fumigatus* did not occur until after the beginning of stationary phase. The fact that transferrin is not hydrolyzed until late logarithmic phase also may be related to the relative resistance of holotransferrin to proteolytic cleavage compared to that of apotransferrin (30).

In contrast, transferrin was stable in serum for at least 286 h in control flasks that contained no *A. fumigatus* (FIG. 4, lane C). When holotransferrin alone was added to MEM, it was not degraded by *A. fumigatus* after 286 h of incubation (FIG. 4B). Because transferrin degradation was not observed in either medium during the early growth of *A. fumigatus*, when active growth is occurring and the organism has the greatest requirement for iron, the inventors have demonstrated that transferrin proteolysis is not the primary mechanism of iron acquisition by *A. fumigatus* under conditions of low free iron concentrations. The results showing that *A. fumigatus* was able to grow in MEM containing transferrin alone without any degradation of transferrin (FIG. 4B) further support this finding.

The relative importance of hydrolysis of iron-binding proteins and siderophore secretion has been evaluated with two bacterial pathogens. Using chemical mutagenesis, Okujo et al. (31) created a mutant of *V. vulnificus* that was deficient in the secretion of an extracellular protease (VVP) but was still able to secrete the siderophore vulnibactin. They compared the growth in holotransferrin of this mutant and a VVP-secreting strain that produced only small amounts of the siderophore. Their results indicated that siderophore production rather than VVP secretion was necessary for growth when ferrated transferrin was the sole iron source. In another study, Wolz et al. (29) created a strain of *Pseudomonas aeruginosa* that was unable to produce LasB, the only secreted protease capable of transferrin hydrolysis. LasB mutants were still able to remove iron from transferrin by use of the *P. aeruginosa* siderophore pyoverdin, suggesting that siderophore production alone was sufficient to obtain iron. However, when pyoverdin and transferrin were present in equimolar concentrations, iron exchange was enhanced by the proteolytic degradation of transferrin by LasB (29). A similar scenario could be envisioned for *A. fumigatus* growing in serum during late logarithmic phase, when protease secretion is maximal.

Example 1.6

*A. fumigatus* can Remove Iron from Holotransferrin, Even Across a Dialysis Membrane The ability of *A. fumigatus* cultures to remove iron from holotransferrin was investigated with urea-PAGE. Urea-PAGE can be used to distinguish among holotransferrin ($Fe_2$-transferrin), $Fe_C$-transferrin, transferrin-$Fe_N$, and apotransferrin based upon their different degrees of resistance to denaturation in 6 M urea.

*A. fumigatus* was cultured in MEM containing either 10% human serum or 2.5½M human holotransferrin. In medium containing 2.5½M holotransferrin, the relative amount of holotransferrin decreased and apotransferrin was detected within 8 h (FIG. 5A). The human serum contained a mixture of apotransferrin and monoferric transferrin, but within 8 h of incubation with *A. fumigatus*, monoferric transferrin was no longer detected in the human serum; only apotransferrin was present (FIG. 5B). Since transferrin was not degraded until more than 22 h of culturing (FIG. 4), the iron was removed from intact holotransferrin.

The inventors have also shown that *A. fumigatus* can remove iron from transferrin across a dialysis membrane. Holotransferrin was placed within a dialysis bag to determine whether small molecules produced by *A. fumigatus*, such as siderophores, were responsible for the removal of iron from transferrin. Holotransferrin (25½M) was dissolved in MEM and sealed within a dialysis bag with a molecular mass cutoff of 12 to 14 kDa (Fisher). Most known fungal siderophores are smaller than 1 kDa and so should readily pass through the dialysis membrane. The dialysis bag was suspended in 25 ml of MEM in a 75 ml flask. The medium in the flask was inoculated with *A. fumigatus* ($2.5 \times 10^7$ conidia) and incubated at 37° C. with slow shaking for 48 h. As a control, an uninoculated flask was maintained under the same conditions.

The iron-binding state of the transferrin was monitored by urea-PAGE. Despite physical separation from *A. fumigatus*, holotransferrin contained within the dialysis bag was almost completely deferrated during incubation with *A. fumigatus*

Figure 6:
FIG. 6 shows the transport of iron from transferrin across a dialysis membrane by *A. fumigatus*. *A. fumigatus* was inoculated into MEM in which a dialysis bag containing holotransferrin (25 μM) was suspended. *A. fumigatus* was incubated for 48 h, and then transferrin was withdrawn from the dialysis bag and analyzed by urea-PAGE (lane +). An uninoculated control flask containing MEM plus transferrin in a dialysis bag also was examined (lane −). Pure holotransferrin ($Fe_2$-Tf) and apotransferrin (Apo-Tf) standards also were run.

(FIG. 6). In the uninoculated control, no deferration of transferrin was observed. Acid production did not cause the release of iron from transferrin because the pH of MEM did not drop below 7.0 during the incubation period.

Example 1.7

*A. fumigatus* Secretes Siderophores in the Early Phase of Growth in Transferrin-Containing Medium The inventors have also demonstrated that *A. fumigatus* secretes siderophores in the early phase of growth in transferrin-containing medium, and that these siderophores are capable of removing iron from transferrin in vitro. As described below, *A. fumigatus* secretes up to five different iron-binding compounds. The two major siderophores secreted by *A. fumigatus* are identified as triacetylfusarinine C (TAF) and ferricrocin, and the secretion of siderophores by *A. fumigatus* is shown not to be strain specific. Furthermore, *A. fumigatus* siderophores can compete for transferrin-bound iron, and at least two *A. fumigatus* siderophores, namely TAF and ferricrocin, are able to remove iron from holotransferrin in vitro.

In this example total siderophore secretion by *A. fumigatus* was quantified by using CAS shuttle solution and desferriferrichrome to generate a standard curve. Total siderophore concentrations were measured by using chrome Azurol S (CAS) assay shuttle solution (32). Culture supernatants of *A. fumigatus* were diluted and mixed with an equal volume of CAS shuttle solution. The absorbance at 630 nm was measured. Dilutions of desferriferrichrome (Sigma) were used to generate a standard curve.

Figure 5:
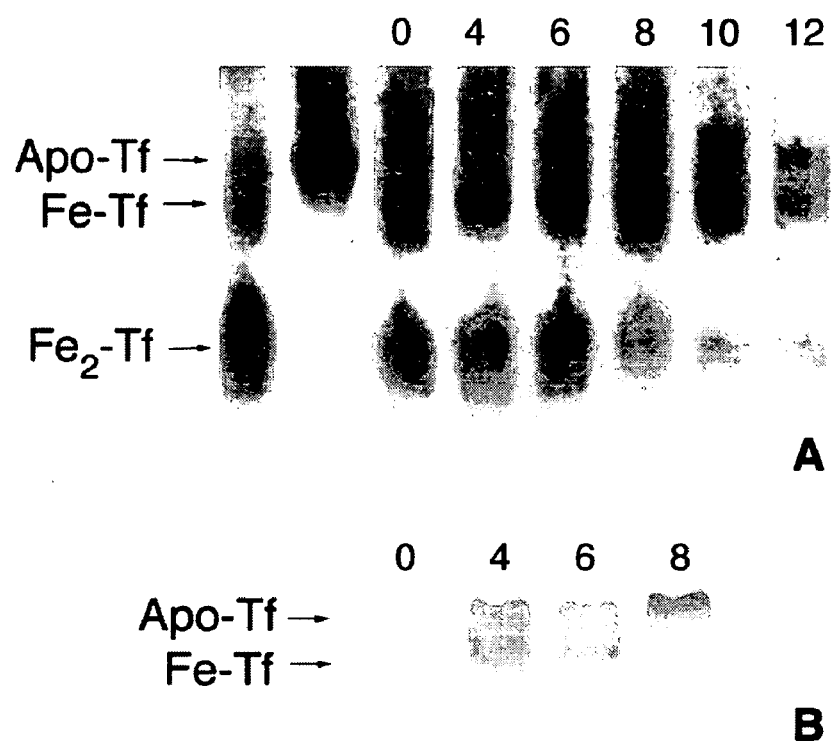
FIG. 5 shows iron removal from transferrin by *A. fumigatus*. *A. fumigatus* was cultured in MEM containing 2.5 μM purified human holotransferrin (A) or 10% human serum (B). Culture media were withdrawn, and the iron saturation of transferrin was analyzed by urea-PAGE. Transferrin was visualized by Western blotting. The numbers above the lanes represent the hours of incubation with *A. fumigatus*. $Fe_2$-Tf, holotransferrin; Apo-Tf, apotransferrin.
Figure 7:
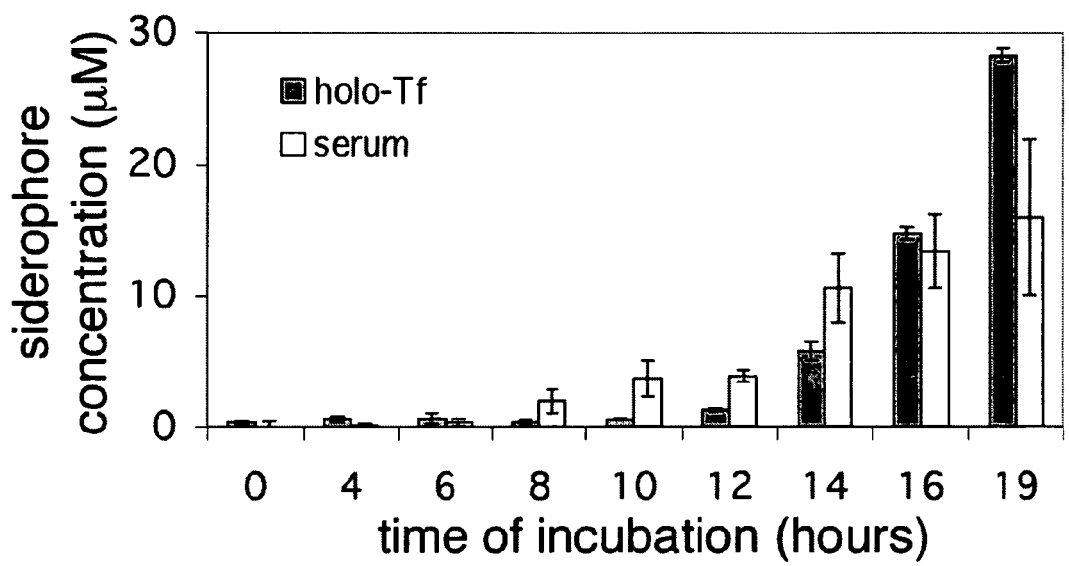
FIG. 7 shows siderophore secretion by *A. fumigatus* in MEM containing holotransferrin or human serum. *A. fumigatus* spores ($10^6$/ml) were added to MEM containing 2.5 μM holotransferrin (holo-Tf) or 10% human serum at time zero. The cultures were incubated at 37° C. and 150 rpm. The siderophore concentrations in the culture supernatants were determined by the CAS assay. Error bars indicate standard deviations.

Cultures were monitored during the early phase of growth to determine whether siderophore secretion could be responsible for the removal of iron from transferrin observed in the first 8 h of culturing. In MEM containing 10% human serum, significant levels of siderophores were first detected by the CAS assay at 8 h. In MEM supplemented with 2.5½M holotransferrin, significant levels of siderophore secretion were observed at 12 h (FIG. 7). Thus, siderophore secretion occurs early in the growth of *A. fumigatus*, coinciding with the first observed removal of transferrin-bound iron after 8 to 12 h of incubation (FIG. 5).

As stated above, holotransferrin incubated with *A. fumigatus* conidia was converted to apotransferrin within 8 h, approximately the same time at which siderophores were detected by the CAS assay and very soon after the germination of conidia. Unlike proteinase secretion (27), siderophore production occurs early in the growth of *A. fumigatus*. These data suggest that siderophore-mediated removal of iron from human transferrin is important in the growth of *A. fumigatus*. The removal of iron from transferrin across a dialysis membrane described above further supports the finding that *A. fumigatus* uses siderophores to obtain iron, as opposed to expressing transferrin receptors or ferric reductase proteins.

Example 1.8

Purification and Identification of Siderophores from *A. fumigatus* Culture Medium The inventors were able to purify and identify siderophores from *A. fumigatus* culture medium in this example. Hydroxamate siderophores were purified from culture supernatants of *A. fumigatus* by using a modification of the method described by Payne (33). *A. fumigatus* was cultured in acid-washed flasks containing 4 liters of modified Grimm-Allen medium [containing, per liter, 1 g of $KHSO_4$, 3 g of $K_2HPO_4$, 3 g of $(NH_4)SO_4$, 20 g of sucrose, 1 g of citric acid, 2 mg of thiamine, 20 µg of $CuSO_4$, 1 mg of $MnSO_4$, 5.5 mg of $ZnSO_4$, and 810 mg of $MgSO_4$ (pH 6.9)]. This medium was inoculated with $4 \times 10^9$ conidia, and the flasks were incubated at 150 rpm and 37° C. for 72 h. The cultures were filtered through MIRACLOTH™ to remove mycelia, and the filtrate was concentrated under vacuum to 350 ml. Ammonium sulfate (50% saturation) and 5 g of $FeCl_3$/liter were added, and the solution was stirred at 4° C. for 16 h.

The concentrated filtrate was filtered through Whatman paper and extracted five times with 50 ml of benzyl alcohol. Anhydrous ethyl ether (750 ml) was added to the combined benzyl alcohol fractions, and the siderophores were extracted eight times into 15 ml of double-distilled $H_2O$. The aqueous layer was washed with diethyl ether and lyophilized to dryness. Siderophores were separated by flash column chromatography with dichloromethane and methanol. The separation of siderophores was confirmed by thin-layer chromatography.

Desferritriacetylfusarinine C was extracted from the medium by the same procedure but without the addition of $FeCl_3$. Purification was achieved by preparative thin-layer chromatography with precleaned Silica Gel 60 $F_{254}$ plates and 1-butanol-ethanol-water (5:3:2). Bands were visualized under UV light, and iron-reactive layers were scraped, extracted with water, and lyophilized. Iron was removed from ferricrocin by treatment with 8-hydroxyquinoline. Ferricrocin was dissolved in slightly alkaline water (10 mg/ml), and a 10-fold (wt/wt) excess of 8-hydroxyquinoline was added. This mixture was heated for 30 min at 60° C. and allowed to stand overnight at room temperature. Most of the 8-hydroxyquinoline was removed by centrifugation, and the remainder was removed from the supernatant by five extractions with chloroform.

Figure 8:
FIG. 8 shows the thin layer chromatographic separation of *A. fumigatus* siderophores. Siderophores were extracted from *A. fumigatus* culture medium and separated by flash column chromatography.

Extraction of the culture medium with benzyl alcohol revealed five different iron-binding compounds, which could be distinguished by their Rf values after thin-layer chromatography (Table 2). These compounds were purified by flash column chromatography. An example of a thin layer chromatographic separation of *A. fumigatus* siderophores, showing at least four siderophores produced by *A. fumigatus*, is shown in FIG. 8. The red, orange, and yellow compounds lost their color when treated with the iron chelator 8-hydroxyquinoline. Fraction 3 contained by far the most abundant siderophore produced under these culture conditions, with fractions 1, 2, and 5 producing much smaller amounts (Table 2).

MALDI-TOF, $^1H$ NMR, and $^{13}C$ NMR mass spectra were used to identify the two most abundant *A. fumigatus* siderophores as triacetylfusarinine C and ferricrocin. Matrix-assisted laser desorption ionization-timeof-flight (MALDI-TOF) mass spectra were obtained for samples dispersed in a α-cyano-4-hydroxycinnamic acid matrix (triacetylfusarinine C and desferritriacetylfusarinine C) or a 2,5-dihydroxybenzoic acid matrix (ferricrocin and desferriferricrocin) by using a PerSeptive Biosystems Voyager-DE instrument.

$^1$H and $^{13}$C nuclear magnetic resonance (NMR) spectra were recorded at 293 K by using a Bruker AMX-400 NMR spectrometer or a Varian Inova 500-MHz NMR spectrometer. All chemical shifts are reported relative to TMS. Correlation spectroscopic (COSY, TOCSY, NOESY, and ROESY) studies of desferriferricrocin allowed assignment of all signals to specific amino acid residues.

MALDI-TOF mass spectra were obtained for both the ferrated and the desferri forms of both triacetylfusarinine C and ferricrocin. The mass ions observed (Table 3) are in agreement with the identification of the siderophores as triacetylfusarinine C ($C_{39}O_{15}N_6H_{57}Fe$, 905.78) and ferricrocin ($C_{28}O_{13}N_9H_{44}Fe$, 770.58). $^1$H NMR and $^{13}$C NMR spectra of the deferrated siderophores (Tables 4, 5, and 6) were in agreement with published spectra of desferritriacetylfusarinine C (34) and desferriferricrocin (35, 36, 37). The $^1$H NMR spectrum of desferriferricrocin has not been fully reported; therefore, detailed proton assignments were determined by using a combination of COSY, TOCSY, NOESY, and ROESY NMR spectra with dimethyl sulfoxide (DMSO-$d_6$) solvent at 293 K (Table 5).

TABLE 2

Siderophores produced by *A. fumigatus* ATCC 13073.

| Fraction | $R_f{}^a$ | Yield[b] (mg) |
|---|---|---|
| 1 | 0.57 | 15 |
| 2 | 0.51 | 15 |
| 3 | 0.43 | 450 |
| 4 | 0.31 | 23 |
| 5 | 0.09 | 13 |

[a]The solvent was chloroform-benzyl alcohol-methanol (2:1:1 [vol/vol/vol]), except for fraction 5, for which the solvent was present at 2:1:2.
[b]Dry weight of pure compound isolated per liter of culture medium. *A. fumigatus* was inoculated into Grimm-Allen medium and grown for 72 h at 37° C. and 150 rpm.

TABLE 3

Calculated and measured mass ions for ferrated and desferri forms of fractions 3 and 4.

| | Mass ion | | | |
|---|---|---|---|---|
| Form | Calculated for triacetylfusarinine C | Observed for fraction 3 | Calculated for ferricrocin | Observed for fraction 4 |
| Ferrated MH$^+$ | 906.79 | 906.77 | 771.59 | 771.37 |
| Ferrated MNa$^+$ | 928.79 | 928.76 | 793.57 | 793.38 |
| Desferri MH$^+$ | 853.97 | 853.74 | 718.76 | 718.33 |
| Desferri MNa$^+$ | 875.97 | 875.67 | 740.75 | 740.37 |

TABLE 4

NMR chemical shifts observed for purified desferri form of fraction 3 at 293 K confirm its identity as triacetylfusarinine C.

| | Signal for: | | | |
|---|---|---|---|---|
| | $^1$H NMR with DMSO-$d_6$ | | $^{13}$C NMR with CDCl$_3$ | |
| Structural group | Published[a] | Fraction 3 | Published[a] | Fraction 3 |
| αCH | 4.18(m) | 4.06 > 4.23(m) | 52.5 | 52.6 |
| βCH$_2$ | 1.62(m) | 1.44 > 1.73(m) | 29.3 | 28.9 |
| γCH$_2$ | 1.62(m) | 1.44 > 1.73(m) | 23.3 | 23.1 |
| δCH$_2$ | 3.48(m) | 3.50(m) | 48.1 | 47.1 |
| >COO> | | | 170.9 | 171.2 |
| N$^δ$-Acyl-CH= | 6.22(s) | 6.31(s) | 118.4 | 119 |
| N$^δ$-Acyl-CH$_2$— | 2.64(t) | 2.66(m) | 32.4 | 31.7 |
| N$^δ$-Acyl-CH$_2$O— | 4.18(m) | 4.06 > 4.23(m) | 62.9 | 62.7 |
| N$^δ$-Acyl-CH$_3$ | 1.87(s) | 1.86(s) | 24.4 | 24.4 |
| N$^δ$-Acyl=C< | | | 149.1 | 149 |
| N$^α$-Acetyl-CH$_3$ | 1.84(s) | 1.83(s) | 22.9 | 22.8 |
| N$^α$-Acetyl>C=O | | | 172 | 171.2[b] |
| Hydroxamic>C=O | | | 172 | 172.1[b] |
| N$^δ$-OH | | 9.74 | | |
| N$^α$H | | 8.21 | | |

[a]Values are from reference (34).
[b]Assignments may be reversed.

TABLE 5

$^1$H NMR chemical shifts for desferri form of fraction 4 at 293 K in DMSO-$d_6$ confirm its identity as desferriferricrocin.

| | Signal(s) at the following residue and fraction: | | | | | |
|---|---|---|---|---|---|---|
| | | | | N$^5$-Acetyl-N$^5$-hydroxyl-$_L$-ornithine | | |
| Structural group | Glycine (1) | Serine (2) | Glycine (3) | 4 | 5 | 6 |
| NH | 8.54 | 8.08 | 8.35 | 8.08 | 7.91 | 7.84 |
| αCH | 3.90, 3.41 | 4.19 | 3.77, 3.69 | 3.97 | 4.17 | 4 |
| βCH | | 3.66, 3.55 | | 1.69, 1.56 | 1.67, 1.57 | 1.62, 1.49 |
| δCH | | | | 1.50, 1.50 | 1.52, 1.52 | 1.53, 1.43 |
| γCH | | | | 3.45, 3.45 | 3.41, 3.49 | 3.44, 3.44 |
| CH3 | | | | 1.96 | 1.96 | 1.93 |
| OH | | 3.5 | | | 9.72[a] | |

[a]Broad NMR signal centered at 9.83 ppm and compatible with ornithine OH.

TABLE 6

$^{13}$C NMR assignments for desferri form of fraction 4
(desferriferricrocin) at 293 K in D$_2$O.
Signal(s) at the following residue:

| Structural group | Glycine | Serine | N$^5$-Acetyl-N$^5$-hydroxyl-$_L$-ornithine |
|---|---|---|---|
| αCH | 43.6, 43.8 | 56.2 | 54.8, 54.8, 55.0 |
| βCH | | 61.3 | 28.4, 29.2, 29.5 |
| δCH | | | 23.2, 23.3, 23.4 |
| γCH | | | 48.2, 48.3, 48.3 |
| Acetyl-CH$_3$ | | | 20.2 |
| C=O | 172.3, 172.6 | 172.9 | 174.5, 174.7, 174.9 |
| Hydroxamic C=O | | | 174.1 |

To date, all *A. fumigatus* siderophores that have been characterized are hydroxamate siderophores; these include triacetylfusarinine C and siderophores of the ferrichrome class, such as ferricrocin. Nilius and Farmer reported the production of six siderophores by *A. fumigatus*, with triacetylfusarinine C being the most prominent, followed by ferricrocin (38). Diekmann and Krezdorn reported that *A. fumigatus* produced several hydroxamate siderophores, including ferricrocin, ferrichrome, ferrichrome C and N'N"N'"-triacetylfusarinine C (TAF) (38). Both TAF and ferricrocin have high thermodynamic iron binding constants, with pM values of 31.8 (39) and 26.5 (40), respectively, compared to transferrin with a pM of 23.6. The kinetic rates of iron uptake from transferrin by both *A. fumigatus* siderophores are similar to those of siderophores such as aerobactin, which are proven virulence factors (41).

Other studies have detected ferricrocin and ferrirubin in *A. fumigatus* cultures (42), although the type and ratio of siderophores produced appeared to vary from strain to strain (38). Siderophores observed in other *Aspergillus* species include ferrichrome, fusigen, ferrichrysin, ferrirhodin, and ferrirubin (37) and the asperchromes (43). *Aspergillus nidulans* produces triacetylfusarinine C and ferricrocin as the two major siderophores.

Example 1.9

Siderophore Production by *A. fumigatus* is not Strain-Specific

Figure 9:
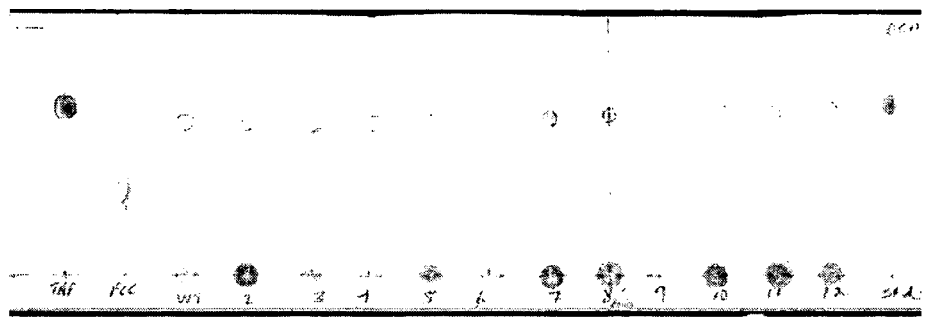
FIG. 9 shows the production of siderophores by different strains of *A. fumigatus*. Thin layer chromatography of media extracts from 11 different strains of '*A. fumigatus*' (labeled 2-12). 'WT' is *A. fumigatus* strain ATCC13073. TAF and ferricrocin standards are spotted in lanes 1 and 2, and lane 15. All strains except #9 produced approximately equal quantities of siderophores indicating that siderophore production is not strain-specific. (*) Note that strain 9 did not produce siderophores; however, this strain does not have the morphological characteristics of *Aspergillus*, therefore it is not an *Aspergillus* sp.

To demonstrate that siderophore production was not unique to the ATCC 13073 strain of *A. fumigatus*, flasks of 10 ml of Neilands' medium with citrate were inoculated with 10$^6$ conidia/ml of various strains of *A. fumigatus*. Incubation was at 37° C. for 5 days at 150 rpm. The media were filtered and a small aliquot of media was treated with iron (FeIII) and lyophilized. The resulting powder was extracted into 50 μl of methanol, centrifuged and spotted onto a TLC plate. All strains except one produced approximately equal quantities of siderophores, indicating that siderophore production is not strain-specific (FIG. 9). The strain that did not produce siderophores lacked the morphological characteristics of *Aspergillus*, therefore it was not an *Aspergillus* sp.

Example 1.10

*A. fumigatus* Siderophores can Compete for Transferrin-Bound Iron

To demonstrate that individual *A. fumigatus* siderophores were able to compete for transferrin-bound iron, holotransferrin was incubated with dilutions of purified desferritriacetylfusarinine C and desferriferricrocin. Holotransferrin also was incubated with commercially available desferriferrichrome for comparison. The iron saturation of transferrin was monitored by urea-PAGE. Desferritriacetylfusarinine C, desferriferricrocin, and desferriferrichrome were diluted to concentrations ranging from 5 mM to 5 μM and incubated with holotransferrin (25 μM) in 50 mM Tris-150 mM NaCl-20 mM NaHCO$_3$ (pH 7.4) buffer for 16 h at 37° C. The extent of iron saturation of transferrin at the end of the incubation period was determined by urea-PAGE.

Figure 10:
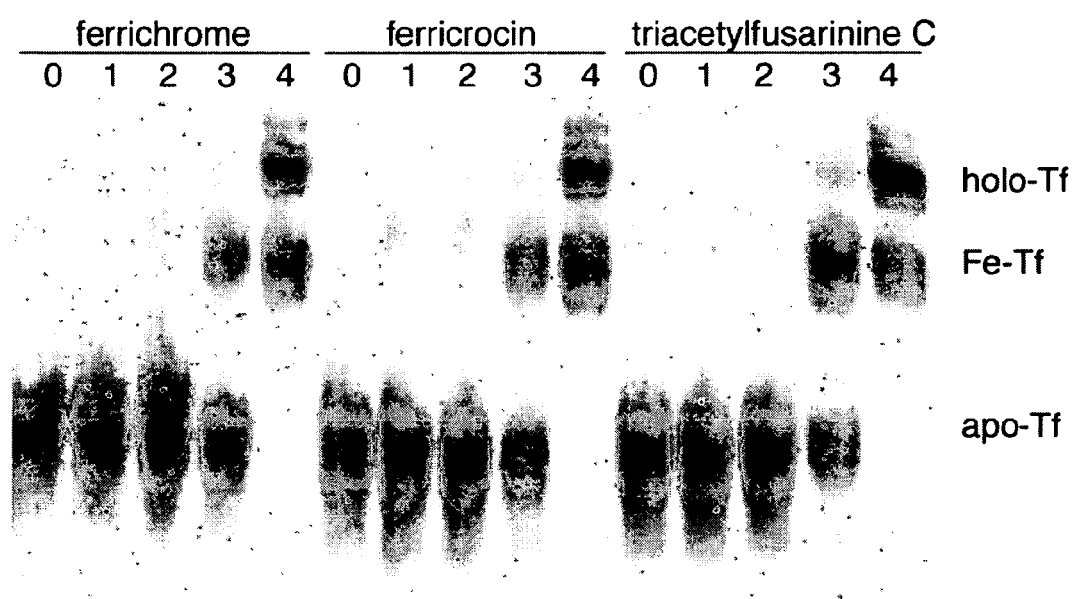
FIG. 10 shows iron saturation of transferrin following incubation with *A. fumigatus* siderophores. Purified desferri-siderophores were incubated with holotransferrin (25 μM) at 37° C. for 16 h. Desferriferrichrome, desferriferricrocin, and desferritriacetylfusarinine C were serially diluted to final concentrations of 5 μM (lanes 1), 50 μM (lanes 2), 500 μM (lanes 3), and 5 mM (lanes 4). Controls containing holotransferrin alone also were run (lanes 0). holo-Tf, holotransferrin; Fe-Tf, monoferric transferrin; apo-Tf, apotransferrin.

The results of this experiment were similar for all three desferrisiderophores. Desferritriacetylfusarinine C, desferriferricrocin, and desferriferrichrome all were able to remove some iron from holotransferrin (25½M) when present at 500½M, although the complete absence of holotransferrin was not observed until the desferrisiderophore concentration reached 5 mM (FIG. 10). A second example of the removal of transferrin-bound iron by *A. fumigatus* siderophores is shown in FIG. 11. These results confirm that at least two of the *A. fumigatus* siderophores can remove iron from human transferrin. Both triacetylfusarinine C and ferricrocin removed iron from holotransferrin with an affinity comparable to that of ferrichrome. The siderophore concentrations necessary to remove iron from transferrin in vivo will depend on the relative local concentrations of the siderophore and transferrin and also may be affected by the presence of cells which actively take up the ferrated siderophore and alter the iron uptake equilibrium.

Example 2.0

Biosynthesis of Hydroxamate Siderophores and Identification of sidA Gene

Figure 12:
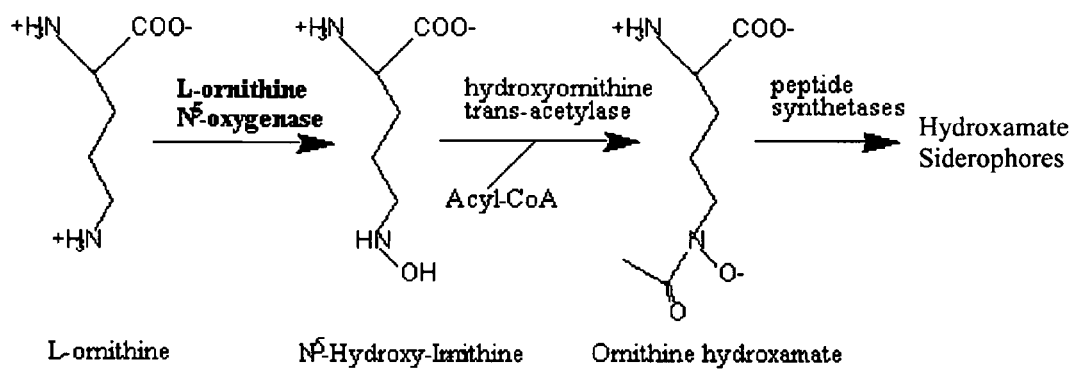
FIG. 12 shows the biosynthetic pathway for hydroxamate siderophores. The first step is the biosynthetic pathway is catalysed by L-ornithine $N^5$-oxygenase. Non-ribosomal peptide synthetases catalyze a subsequent step in the biosynthetic pathway.

FIG. 12 illustrates the biosynthetic pathway for hydroxamate siderophores in *A. fumigatus*. The first step in the pathway is catalyzed by L-ornithine N$^5$-oxygenase. Non-ribosomal peptide synthetases catalyze a subsequent step in the pathway.

Figure 13:
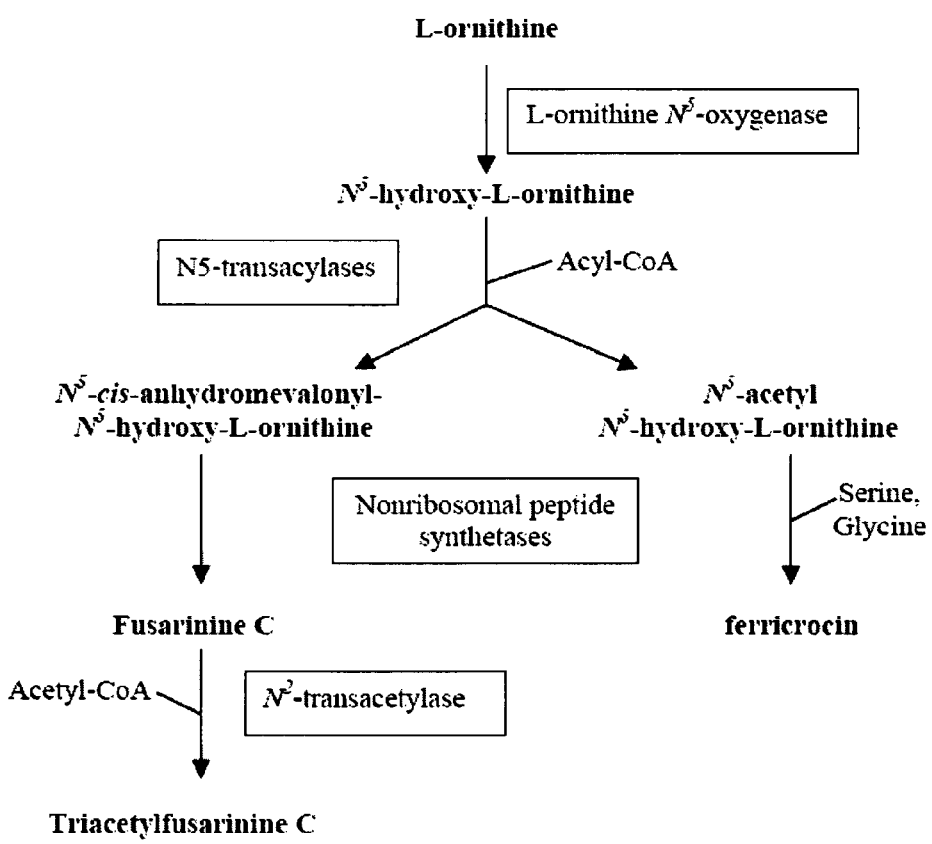
FIG. 13 shows the biosynthetic pathway of hydroxamate siderophores, specifically the biosynthesis of TAF and ferricrocin, according to Plattner and Diekmann (14).

As discussed above, two of the primary hydroxamate siderophores secreted by *A. fumigatus* are TAF and ferricrocin. The biosynthetic pathways for the formation of the hydroxamate siderophores TAF and ferricrocin are shown in FIG. 13 (14). Both TAF and ferricrocin are derived from ornithine, an amino acid that does not occur in proteins but is important in the formation of urea and other polyamines. Ornithine is similar in structure to lysine, containing an amino group at the terminus of a three-carbon side chain. The first step in siderophore biosynthesis involves N-hydroxylation at the terminal amino group of ornithine (FIG. 12). This unusual formation of an N—O bond is catalysed by L-ornithine N$^5$-oxygenases. The N—O functional group later forms an important part of the iron-chelating group of hydroxamate siderophores. The chemical structure of TAF and ferricrocin is shown in FIGS. 28A and B.

A BLAST search of the *A. fumigatus* genome uncovered a sequence with high homology to published sequences for L-ornithine N$^5$-oxygenases. Preliminary sequence data for *A. fumigatus* was obtained from The Wellcome Trust Sanger Institute, and sid1 from *Ustilago maydis* (44) was used as a probe to search the *A. fumigatus* genome for homologous genes. The *A. fumigatus* gene was termed AfusidA, referred to herein as sidA, according to the nomenclature recommended by the *Aspergillus* genome sequencing group (45). The gene was composed of an ORF of 1564 base pairs. Using GlimmerM from the Institute for Genomic Research (TIGR), trained for *A. fumigatus*, an intron of 58 base pairs and an amino acid sequence of 501 amino acids was predicted for the *A. fumigatus* SidA. These sequence data have been submitted to the GenBank database under accession number AY819708. The nucleotide sequence of the sidA gene is set forth in SEQ ID NO:1. The amino acid sequence of the sidA gene product is set forth in SEQ ID NO:2. The nucleotide sequence of the sidA gene includes an intron comprising the nucleotide bases tgt gag cag aga atc aag taa tcc ata ttc tgc ttt ccg ttt tac tga cat aag tct ag, beginning at base 1015 of SEQ ID NO:1 (SEQ ID NO:20).

The coding sequence of the *A. fumigatus* sidA (SEQ ID NO:17) showed very high identity to sidA from *A. nidulans* (SEQ ID NO:18) (75%) and dff1 from *A. oryzae* (SEQ ID NO:19) (74%) (FIG. 14). The *A. fumigatus* sequence (SEQ ID NO:17) contained the three signature sequences typical of amino acid hydroxylase enzymes. The first of these is the conserved putative binding sites for the substrate DXXX(L/F)ATGYXXXXP (46), located at residue 400 of SEQ ID NO:17 (SEQ ID NO:21). Typical of ornithine-binding enzymes, such as pvdA and sid1, the last P of this sequence was not conserved in sidA and was replaced by H. An FAD binding domain, GXGXXG, was found at residue 45 of SEQ ID NO:17, and the last glycine in this domain of sidA was exchanged for proline, which is typical of siderophore biosynthetic enzymes (46). An NADP binding site, GXGXXG, was found at residue 254 of SEQ ID NO:17, though again typical for siderophore biosynthetic genes, the last G in sidA was not conserved (46).

While BLAST searches using the *A. fumigatus* ornithine oxygenase amino acid sequence also showed that it was homologous to many bacterial and fungal L-amino acid oxygenases, these searches also showed that no homologues exist in humans. Indeed, no significant protein sequence similarity was found to any human protein. For these reasons, this protein represents an excellent fungal-specific target for the development of novel antifungal agents.

Example 3.0

Creation and in Vitro Testing of ΔsidA Mutant Strain of *A. fumigatus*

In this example a mutant strain of *A. fumigatus* incapable of producing hydroxamate siderophores was created. The siderophore production mutant strain is incapable of growth on iron-limited media, while supplementation of the media with iron or TAF, or the use of complex media, permits growth equivalent to wild type *A. fumigatus*. Although growth is delayed in minimal medium supplemented with iron, the lag phase, rate of growth, and timing of conidiation of the siderophore production mutant are the same as wild type *A. fumigatus* when minimal medium is supplemented with TAF. Thus, siderophores are critical for the normal growth of *A. fumigatus* in iron-limiting environments.

Additionally, the mutant strain is unable to remove iron from holotransferrin, and is also unable to grow in serum-containing media. A rescued strain of the siderophore production mutant strain exhibits similar behaviour to wild type, indicating that the growth defects of the mutant strain are due to the specific gene deletion. Ferric reductase activity is not upregulated in ΔsidA to compensate for the defect in siderophore secretion. In summary, the inventors have shown that the survival of *A. fumigatus* in iron-limited media depends upon siderophore secretion.

Example 3.1

Construction of an *A. fumigatus* Siderophore Secretion Mutant by Disruption of the sidA Gene In an exemplary embodiment, the inventors have created a siderophore-secretion mutant by deleting the *A. fumigatus* L-ornithine $N^5$-oxygenase (ornithine oxygenase) gene (sidA), which encodes the enzyme catalyzing the first committed step in siderophore biosynthesis (FIG. 12).

The role of siderophores in iron uptake of *A. fumigatus* was established by deleting the sidA gene by gene replacement. Southern analysis revealed only one copy of sidA in *A. fumigatus* genomic DNA. To construct a sidA deletion vector, standard molecular techniques were carried out as described by Sambrook et al. (47). Plasmids were propagated in *Escherichia coli* DH5α (Life Technologies). Genomic DNA was extracted from *A. fumigatus* by standard phenol chloroform extraction (47) as decribed by May et al. (48) pID620, composed of pBluescript SK+ (Stratagene) containing the hph hygromycin resistance cassette in the EcoRI site (49), was kindly provided by D. W. Holden, Department of Infectious Diseases and Bacteriology, Royal Postgraduate Medical School, Imperial College of London, UK. Custom primers were ordered through Invitrogen.

Figure 15:
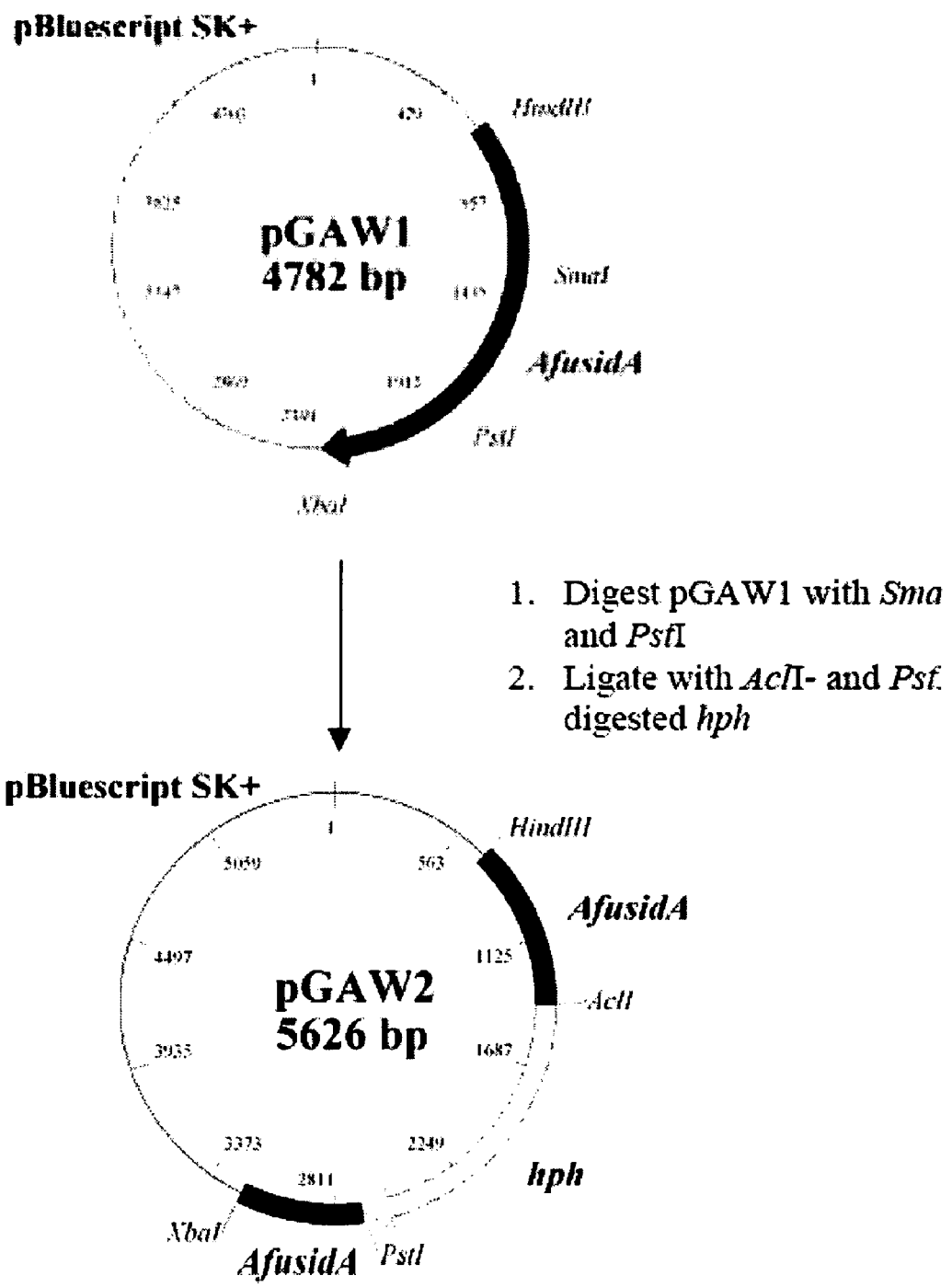
FIG. 15 shows the construction of the sidA gene deletion vector. The 1.6 kb sidA gene was PCR amplified and ligated into HindIII- and XbaI digested pID620, generating pGAW1. pGAW1 was then digested with SmaI and PstI, excising ~500 bases of the sidA coding region including the NADPH binding domain. The hph hygromycin resistance cassette was PCR amplified from pID620 and digested with AclI and PstI. hph was ligated to the digested pGAW1, creating the sidA gene replacement vector, pGAW2.

A 1.6 kb DNA fragment containing sidA was PCR amplified from *A. fumigatus* genomic DNA using primers 5'-AAGCTT<u>AAGCTT</u>TTGAACGGAAGTCAGAATCG (SEQ ID NO:3) and 5'-TCTAGA<u>TCTAGA</u>ACAGGTTCCCTCATGTCTGC (SEQ ID NO:4) which flank the sidA gene and contain restriction sites for HindIII and XbaI, respectively (underlined). This PCR product was digested with HindIII and XbaI, then ligated into HindIII- and XbaI-digested pID620, generating pGAW1. pGAW1 was then digested with SmaI and PstI, excising bases 576-1078 of the sidA coding region. The hygromycin resistance cassette (hph) was PCR-amplified from pID620 using primers 5'-AACGTT<u>AACGTT</u>GTAAAACGACGGCCAGTG (SEQ ID NO:5) and 5'-GGAAACAGCTATGACCATG (SEQ ID NO:6) (the added restriction site for AcII is underlined). This PCR product was digested with AcII and PstI and ligated to the digested pGAW1, creating the sidA gene replacement vector, pGAW2. pGAW2 is a transformation vector containing a nonfunctional sidA gene and a selectable marker. In the pGAW2 sidA gene, bases 576-1078 of the sidA coding region were replaced by hph, removing required domains such as the NADPH binding site at residue 254. The plasmids pGAW1 and pGAW2 are shown in FIG. 15. The correct disruption of sidA in the transformation vector pGAW2 was confirmed by sequencing the gene deletion construct (University Core DNA and Protein Services, University of Calgary, Alberta, Canada).

To create a mutant strain of *A. fumigatus* with the sidA gene deleted, strain ATCC 13073 was transformed by electroporation with pGAW2. *A. fumigatus* was transformed by electroporation, according to the method of Weidner et al. (50) Transformation reactions were plated on *Aspergillus* minimal medium (MM) containing 10 g/L glucose, 0.85 g/L NaNO3 0.52 g/L KCl, 0.52 g/L $MgSO_4.7H_2O$, 1.52 g/L $KH_2PO_4$, 40 μg/L $Na_2B_4O_7.10H_2O$, 0.4 mg/L $CuSO_4.5H_2O$, 1 mg/L $FePO_4.4H_2O$, 0.6 mg/L $MnSO_4.H_2O$, 0.8 mg/L $Na_2MoO_4.2H_2O$, 8 mg/L $ZnSO_4.7H_2O$, 1 mg/L nicotinic acid, 2.5 mg/L riboflavin, 2 mg/L pantothenic acid, 0.5 mg/L pyridoxine, 10 μg/L biotin, 0.2 mg/L PABA, and 10 μM TAF, pH 6.5. The plates were incubated at room temperature overnight, then overlayed with 10 ml of MM containing 267 μg/ml hygromycin B (Roche) and 1.5% agar. Plates were then incubated at 37° C. for 48 hours until colonies had conidiated.

Figure 16:
FIG. 16 shows the screening of transformants for defects in the production of siderophores. *A. fumigatus* was transformed with pGAW2, and the resulting transformants were plated on CAS agar for screening. Siderophore secretion produces yellow halos surrounding colonies. The yellow halos are visible in FIG. 16 as lighter grey halos surrounding the colonies.

The resulting hygromycin resistant strains were screened for absence of siderophore production in low iron modified Grimm-Allen (GA) medium. Conidia from putative transformants were screened in 2 ml modified GA medium supplemented with 10 μM TAF to support the growth of siderophore secretion mutants. This concentration was low enough to avoid interference in the colourimetric detection of siderophores. Cultures were incubated at 37° C. for 3 days. Cultures were selected which did not produce any orange colour upon addition of 200 µl of 10 mg/ml $Fe_2SO_4$. Ten of 140 hygromycin-resistant colonies showed lack of siderophore secretion by this test. These transformants were further screened by PCR to ensure deletion of sidA gene. An alternative means of screening for defects in the production of siderophores is to plate transformants on CAS agar, as shown in FIG. 16. Siderophore secretion produces yellow halos surrounding colonies (visible in FIG. 16 as lighter grey halos surrounding the colonies).

Figure 18:
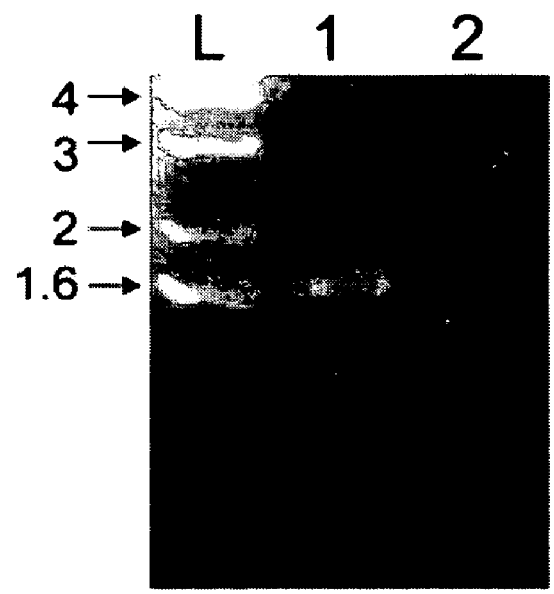
FIG. 18 shows genomic DNA from wild type and ΔsidA that was amplified using primers flanking sidA oof and oor, as shown in FIG. 17. Wild type sidA gene should give a PCR product of 1.6 kb. In the gene deletion strain, ΔsidA, sidA is interrupted by hph and should give a PCR product of 2.8 kb. No 1.6 kb product should be present in ΔsidA. L=1.6 kb DNA ladder, 1=PCR reaction with wild type DNA, 2=PCR reaction with ΔsidA DNA. Numbers to the left of the gel denote size of DNA ladder bands in kb.
Figure 19:
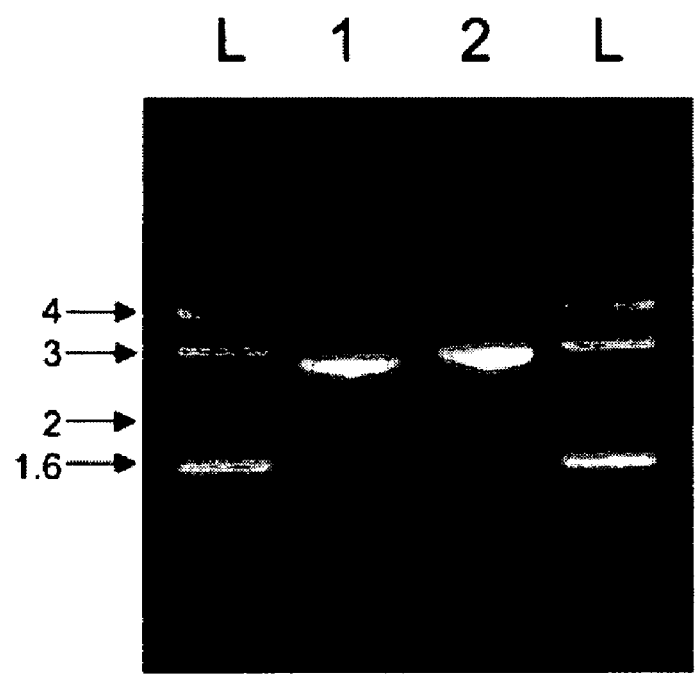
FIG. 19 shows PCR evidence that pGAW2 integrated at the correct site, deleting sidA. Genomic DNA from ΔsidA was amplified using primers complementary to hph (hph1 and hph2) and to regions upstream and downstream of sidA (be-oof and afoor) as shown in FIG. 17. No product would be observed if the pGAW2 DNA had integrated at a location other than the sidA gene. A 2.7 kb product is expected for primers be-oor and hph2, and a 2.9 kb product is expected for primers af-oor and hph1 if double cross-over has occurred. L=1.6 kb DNA ladder, 1=PCR reaction with hph2 and be-oof, 2=PCR reaction with hph1 and af-oor. Numbers to the left of the gel denote size of DNA ladder bands in kb

The correct disruption and integration of the gene deletion construct was confirmed in one strain, 19B4, by PCR using the sidA primers and primers to hph and from regions upstream and downstream of the sidA gene. Gene deletion was confirmed by PCR at the sidA site (FIGS. 17 and 18) using the primers 5'-TTGAACGGAAGTCAGAATCG (oof) (SEQ ID NO:7) and 5'-ACAGGTTCCCTCATGTCTGC (oor) (SEQ ID NO:8) which flank the sidA gene. Gene deletion was also confirmed by PCR using primers complementary to hph (FIGS. 17 and 19): 5'-GACATATCCACGC-CCTCCTA (hph1) (SEQ ID NO:9) and 5'-ACTGTCG-GGCGTACACAAAT (hph2) (SEQ ID NO:10) and to a region just external to the sidA gene: 5'-ACGCCCTCAACT-GTATGGAC (be-oor, 1.8 kb upstream of sidA start codon) (SEQ ID NO:11) and 5'-TTTCGTGCAAAACAGTGGAG (af-oof, 1.6 kb downstream of sidA stop codon) (SEQ ID NO:12). PCR was carried out using 1 µg genomic DNA from either wild type or the putative ΔsidA strain, incubated under the following conditions: predwell at 95° C. for 2 minutes, then 30 cycles of 94° C. for 30 seconds, 55° C. for 90 seconds, and 72° C. for 30 seconds. Postdwell was for 10 minutes at 72° C.

Figure 17:
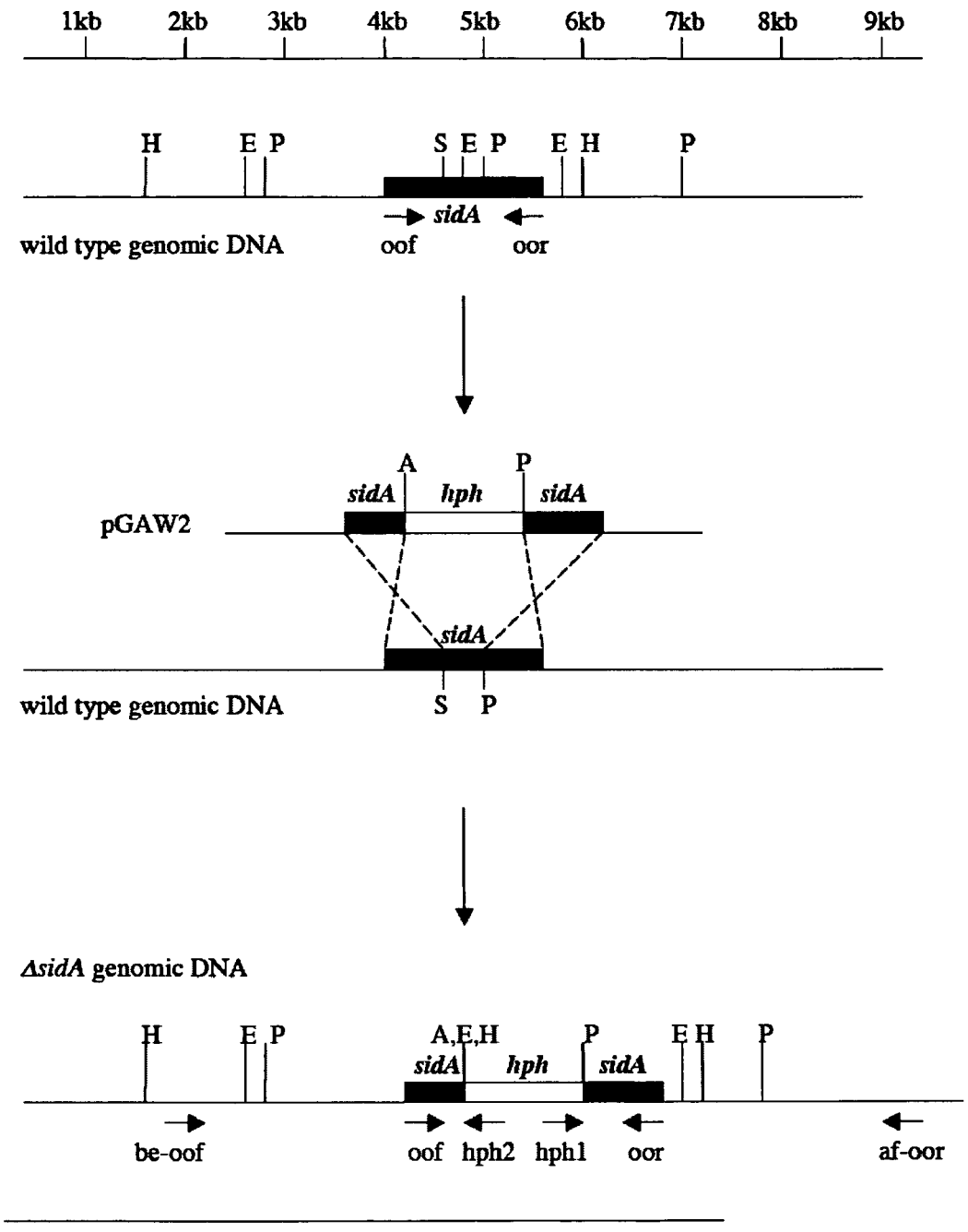
FIG. 17 shows a double crossover gene deletion showing the binding sites for primers used to create the sidA deletion mutant, and restriction sites for PstI, HindIII and EcoRV for *A. fumigatus* parental and ΔsidA strains.
Figure 20:
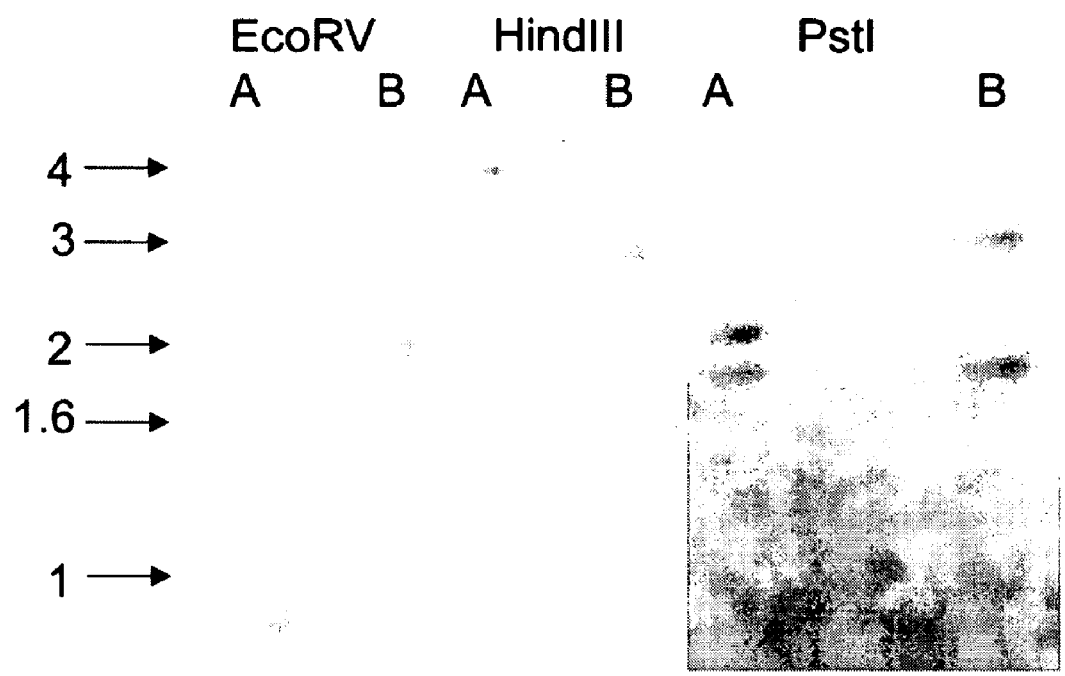
FIG. 20 shows a Southern blot of wild type and ΔsidA genomic DNA, demonstrating deletion of the *A. fumigatus* sidA gene. The Southern blot confirms the deletion of sidA. *A. fumigatus* genomic DNA from wild type and ΔsidA was completely digested with EcoRV, PstI and HindIII, separated by gel electrophoresis and transferred to Hybond N+. Blots were probed using a sidA probe constructed using AlkPhos direct labelling kit. Detection was by the CDP-star reagent. A=wild type genomic DNA, B=ΔsidA genomic DNA. Numbers to the left of the blot represent DNA bands from the ladder (in kb).

Gene deletion was also confirmed by Southern blot analysis. The restriction sites for PstI, HindIII and EcoRV for the *A. fumigatus* parental and ΔsidA strains are shown in FIG. 17, yielding the predicted sizes of bands listed in Table 7. The results of the Southern blot confirming the deletion of sidA are given in Table 7 and FIG. 20. Southern analysis was carried out on genomic DNA extracted from wild type and the putative ΔsidA strain. Genomic DNA was completely digested with EcoRV, PstI and HindIII, fragments were separated by electrophoresis on 0.7% agarose and transferred to Hybond N+ (Amersham) using standard techniques (47). Probes to the sidA gene were constructed using the AlkPhos direct labelling kit with the CDP-star detection reagent (Amersham).

TABLE 7

Predicted and actual sizes of bands appearing on Southern blot.

| | EcoRV | | HindIII | | PstI | |
|---|---|---|---|---|---|---|
| wild type predicted | 2219 | 909 | 4189 | | 2353 | 2038 |
| wild type observed | 2200 | 900 | 4000 | | 2200 | 2000 |
| ΔsidA predicted | 2078 | 2037 | 2966 | 2217 | 3347 | 2038 |
| ΔsidA observed | 2000* | | 3000 | 2100 | 3200 | 2000 |

*bands overlap, therefore only one band was visible on Southern blot

Figure 21:
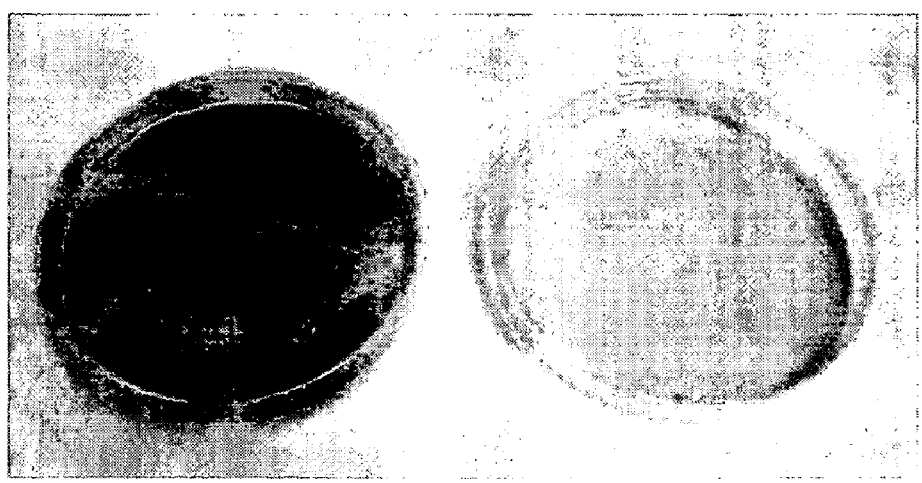
FIG. 21 shows the measurement of the reversion rate of ΔsidA. (A) Wildtype or (B) ΔsidA conidia ($10^6$/ml) were plated onto solid GA medium containing 100 μM of the iron-chelating agent 2,2-dipyridyl. Only wildtype was able to grow under these conditions, indicating no reversion of ΔsidA.

The inventors would not expect to see any revertants if the correct integration had been achieved by double-crossover; therefore, reversion rates of the ΔsidA strain were measured. On Grimm-Allen plates containing 100 µM 2,2-dipyridyl, 1.4×10⁷ ΔsidA conidia were screened without the appearance of a single revertant, while growth of wild type colonies was not inhibited (FIG. 21). The lack of reversion further confirms the correct deletion of sidA.

Example 3.2

Construction of a Rescued Strain of *A. fumigatus* Capable of Siderophore Secretion Genomic 13073 DNA was amplified by PCR with PFU Ultra (Stratagene) using primers corresponding to the wild type sidA gene: forward -505 by upstream of the start codon (GAA TTC GAA TTC TGT CAA GAG CAC CAC ACC TC) (SEQ ID NO:13) and reverse—560 by downstream of the stop codon (GAATTC GAA TTC CCA TCA GAT AAC GCG TGA AA) (SEQ ID NO:14). Both primers contained EcoRI sites to facilitate ligation (underlined). The PCR fragment was cleaned using the QIAquick PCR Purification Kit (Qiagen). The plasmid Bluescript SK+ was cut with EcoRI (Invitrogen) followed by dephosphorylation with APex heat-labile alkaline phosphatase (Epicentre) and gel purification. The PCR product was ligated to the linear plasmid and the resultant plasmid (pCOMP2) used to transform *E. coli* DH5a. Transformants were selected on LB amp with Xgal (1 mg/plate). Successful transformation was confirmed by restriction mapping and sequencing (data not shown), pCOMP2 was linearized with XbaI and used to transform conidia of *A. fumigatus* ΔsidA. The fungi were grown on minimal media (MM) supplemented with TAF, and conidia were swollen in the presence of 10 µmol of TAF and ferricrocin. The conidia were electroporated with 0 or 2 µg DNA and transformants selected on Grimm-Allen agar containing 150 µM dipyridyl. No colonies were observed with the 0 DNA controls. In the samples incubated with 2 µg DNA, three transformants were obtained, and all three were found to be hygromycin-resistant. Successful ectopic integration of sidA was confirmed by PCR using primers homologous to the entire sidA gene (forward: CTC CAT ATG GAA TCT GTT GAA CGG AAG (SEQ ID NO:15), and reverse: CCG AAT TCT TAT TAC AGC ATG GCT CGT AGC (SEQ ID NO:16)). PCR also revealed a band that corresponded to the sidA gene disrupted with hph, indicating that the original mutation was present in the rescued strain. One of transformants (R3) was chosen for phenotypic characterization and to confirm the rescue in the mouse model of invasive aspergillosis, described further below.

To summarize the strains used in these experiments, *A. fumigatus* (ATCC 13073), originally isolated from a human pulmonary lesion, was obtained from the American Type Culture Collection. *A. fumigatus* 13073 ($hyg^S$, $sidA^+$) is sometimes described herein as wildtype, while 19B4 ($hyg^R$, $sidA^-$) is designated ΔsidA. R3 is the rescued strain designated ΔsidA$^R$ ($hyg^R$, $sidA^+$). 13073, 19B4, and the rescued strain are isogenic except for the disruption/addition of the sidA gene.

Example 3.3 sidA is Required for the Secretion of Hydroxamate Siderophores by *A. fumigatus*

As described above, the inventors have shown that sidA is required for secretion of TAF and ferricrocin (i.e. sidA catalyses the first committed step in hydroxamate siderophore biosynthesis). *A. fumigatus* is known to secrete several siderophores of the hydroxamate group, and all should be absent in the ΔsidA mutant. To determine whether sidA was required for the production of siderophores in *A. fumigatus*, conidia ($10^6$/ml) were inoculated into 5 ml volumes of YG. YG was used for this experiment because it supports identical growth rates of wild type and ΔsidA without inhibiting siderophore secretion (as discussed below). Both strains were cultured at 37° C. for 3 days, at which time mycelia were removed by filtration, and 100 mg/ml $FeCl_3$ was added to the supernatants.

Ferrated siderophores were then extracted from the aqueous supernatants with 3×1 ml 1:1 phenol:chloroform. Combined phenol:chloroform fractions were washed with 2 ml $dH_2O$, then diluted with 10 ml diethyl ether. The siderophores were extracted from the diethyl ether fraction with 2×0.5 ml $dH_2O$. Combined aqueous layers were washed with 0.5 ml diethyl ether, then lyophilized to dryness. Extracts were redissolved in 30 μl $ddH_2O$ and analysed on silica gel thin layer chromatography sheets using a running phase of 4:1 dichloromethane:methanol. Rf values were compared to those measured for TAF and ferricrocin.

Figure 22:
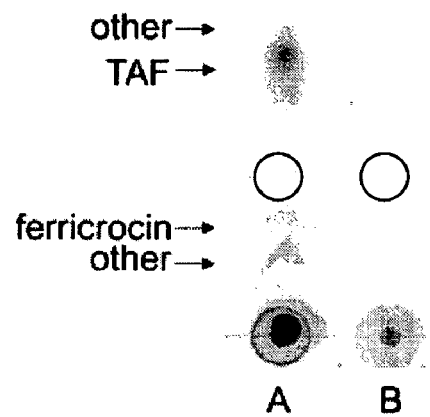
FIG. 22 shows thin layer chromatography of siderophores produced by wild type and ΔsidA strains of *A. fumigatus*. Siderophores were extracted from wild type and ΔsidA cultures grown in 5 ml volumes of modified GA medium at 37° C. for 3 days as described in materials and methods. Extracts were analysed on silica gel thin layer chromatography sheets using a running phase of 4:1 dichloromethane:methanol. Ferricrocin, TAF, plus two unidentified siderophores (labeled-other )-are visible in the wild type extract (A), while no siderophores are visible in extract from ΔsidA (B). Faint yellow spots in the ΔsidA extracts (visible as the faint grey spots circled in FIG. 23) were also present in the uninoculated control (data not shown).

TAF, ferricrocin and two unidentified siderophores were clearly visible in the extract from wild type strain; however, neither TAF, ferricrocin, nor the two additional siderophores could be observed on the TLC of the ΔsidA extracts (FIG. 22). Faint yellow spots on the TLC in the ΔsidA lane (visible as circled grey spots in FIG. 22) correspond to components extracted from the medium that were also present in an uninoculated medium blank. Thus the inventors have demonstrated that sidA is required for production of TAF, ferricrocin and two other unidentified siderophores.

Example 3.4

Siderophore Secretion by *A. fumigatus* is Required for Growth in Low Iron Media and Serum-Containing Media In this example the growth of various strains of *A. fumigatus* was monitored as follows. In a first experiment, *A. fumigatus* was inoculated into 5 ml volumes of YG medium or 5 ml of modified Grimm-Allen (GA) medium (1 g/L $KHSO_4$, 3 g/L $K_2HPO_4$, 3 g/L $(NH_4)SO_4$, 20 g/L sucrose, 1 g/L citric acid, 2 mg/L thiamine, 20 μg/L $CuSO_4$, 1 mg/L $MnSO_4$, 5.5 mg/L $ZnSO_4$, 810 mg/L $MgSO_4$, pH 6.9) in 25 ml acid-washed flasks at a concentration of 106 conidia/ml. GA medium was supplemented with 5½M $FeCl_3$ where described. Human serum (male) was obtained from Sigma, stored frozen until use and added to media at a concentration of 10%. DesferriTAF and desferriferricrocin were purified from *A. fumigatus* cultures as described above and treated with 8-hydroxyquinoline to remove all bound iron. Siderophore solutions were filter-sterilized prior to addition to media.

In a second experiment, *A. fumigatus* was innoculated into 1 ml volumes of YM medium or 1 ml of the modified GA medium described above.

Dry weights of *A. fumigatus* cultures were measured by filtering the entire contents of each flask through MIRA-CLOTH™ (Calbiochem) and rinsing thoroughly with distilled water. Mycelia were then transferred to pre-weighed microcentrifuge tubes, lyophilized and weighed. Alternatively, dry weights were measured by filtering the contents of each tube through pre-weighed, pre-dried Whatman #1 filters and rinsing thoroughly with distilled water. Filters were oven-dried and re-weighed.

These experiments demonstrate that sidA is required for growth in low iron media and serum-containing media. In the first experiment, the ΔsidA mutant and the parental strain grew at equal rates in rich media such as YG (Table 8) which contains yeast extract, malt and peptone. The timing and extent of conidiation of the ΔsidA strain in complex iron-rich media were also indistinguishable from those of the parental strain. However, growth of ΔsidA was severely restricted in iron limited defined media such as GA medium. Supplementing GA with 5 μM $FeCl_3$ or 10 μM TAF restored growth of ΔsidA to wild-type levels (Table 8). In GA containing 5 μM $FeCl_3$, an increased lag period was observed for ΔsidA, in that germination and growth were delayed compared to the wild type for the first 24 hours of incubation. However, after 48 hours the biomass of ΔsidA was identical to that of the parental strain. No delay in conidiation of ΔsidA in GA containing 5 μM $FeCl_3$ was apparent. When GA was supplemented with 10 μM TAF, length of lag phase, rate of growth, and timing of conidiation of ΔsidA were identical to those of the parental strain.

Results of the second example providing additional data demonstrating the importance of sidA for growth in low iron media and serum-containing media is presented in Table 9. After 96 hours, the ΔsidA mutant and the parental strain achieved similar biomass in rich media such as YM; however, growth of ΔsidA was severely restricted in iron-limited medium. Supplementing GA containing 5 μM $FeCl_3$ partially restored the growth of ΔsidA, whereas 10 μM TAF restored growth of ΔsidA to wild type levels. The importance of siderophore biosynthesis to growth in iron-limited media was confirmed by the observation that the rescued strain ΔsidA$^R$ grew equally as well as the wild type strain in GA medium or in medium containing serum. Thus, although the growth inhibition of ΔsidA in low iron medium can be overcome by addition of 5 μM $FeCl_3$, growth of ΔsidA was still less than either the parental or ΔsidA$^R$ strains. These results suggest that ferric iron can promote growth. However, ferric iron could not fully compensate for the absence of siderophores under these conditions.

These results suggest that uptake of $FeCl_3$ by the siderophore secretion mutant was much slower than that of wild type, but that ferric iron could nonetheless promote growth. The mechanism by which *A. fumigatus* ΔsidA strain can access ferric iron is not known, but could involve the reduction of ferric to ferrous iron, followed by uptake by ferrous iron transporters. Despite the lack of siderophore secretion, growth of ΔsidA was not inhibited in rich media such as YG, which contains various organic iron sources such as citrate. These organic iron sources are therefore accessible to *A. fumigatus* ΔsidA through alternative iron uptake pathways, possibly involving ferric reductases. The ΔsidA growth defect in GA medium was completely rescued by addition of 10 μM TAF, indicating that a lack of siderophore secretion is the only cause of the growth inhibition by the GA medium.

TABLE 8

ΔsidA can grow in rich medium, but not iron-limited GA medium.

| Medium | dry weight (mg) | | | |
|---|---|---|---|---|
| | parental | | ΔsidA | |
| YPD | 25.7[1] | 0.5 | 25.9[1] | 0.4 |
| GA | 25[1] | 2 | 0.1[1] | 0.1* |
| GA + $FeCl_3$ | 44.3[1] | 0.1 | 47.4[1] | 3 |
| GA + TAF | 41[1] | 2 | 46[1] | 1 |

*A. fumigatus* was cultured for 4 days at 37° C. in 5 ml volumes of YPD, GA medium, GA medium supplemented with 5 μM $FeCl_3$, or GA medium supplemented with 10 μM TAF. At the end of the incubation period, mycelia were filtered, washed, lyophilized and weighed. Data presented are averages[1] standard deviations. This experiment was performed three times with similar results.
*Significantly different than parental strain (P < 0.005)

TABLE 9

ΔsidA can grow in rich medium, but not iron-limited GA medium, while ΔsidA$^R$ can grow in iron-limited media

| Medium | Strain | Growth (mg dry weight) mean ± S.D. |
|---|---|---|
| YM | Wild type | 3.9 ± 0.2 |
|  | ΔsidA | 5.0 ± 0.6 |
|  | ΔsidAR | 5.0 ± 0.4 |
| GA | Wild type | 3.9 ± 0.7 |
|  | ΔsidA | 0.3 ± 0.5* |
|  | ΔsidAR | 7.6 ± 1.6 |
| GA + FeCl$_3$ (5 μM) | Wild type | 6.5 ± 0.4 |
|  | ΔsidA | 1.4 ± 1.1* |
|  | ΔsidAR | 7.5 ± 0.3 |
| GA + TAF (ferrated, 10 μM) | Wild type | 6.2 ± 0.5 |
|  | ΔsidA | 4.4 ± 1.5 |
|  | ΔsidAR | 6.0 ± 0.1 |
| GA + FeCl$_3$ + serum[a] | Wild type | 9.4 ± 0.7 |
|  | ΔsidA | 0.0 ± 0.0* |
|  | ΔsidAR | 9.5 ± 0.8 |
| GA + FeCl$_3$ + serum + desferri-TAF (50 μM) | Wild type | 10.1 ± 0.4 |
|  | ΔsidA | 12.3 ± 1.2 |
|  | ΔsidAR | 11.3 ± 0.3 |
| GA + FeCl$_3$ + serum + desferriferricrocin (50 μM) | Wild type | 9.7 ± 2.00 |
|  | ΔsidA | 11.1 ± 1.1 |
|  | ΔsidAR | 11.0 ± 1.2 |

Data presented are averages ± standard deviations of triplicate values. This experiment was performed three times with similar results.
[a]10% (v/v) human serum
*Significant growth inhibition relative to wild type (p < 0.03 by ANOVA with Dunnett's Multiple Comparison Test)

Data for a third experiment involving the rescue of growth of the ΔsidA mutant by siderophores are shown in Table 10. Growth of the siderophore secretion mutant ΔsidA could be restored to wild-type levels by the addition of 50 μM desferriTAF or 50 μM desferriferricrocin. These siderophore concentrations were chosen because they are similar to the concentration of siderophore produced by wild type *A. fumigatus* in this medium. These data indicate that siderophores are required for *A. fumigatus* growth in the presence of human serum. These results demonstrate that none of the alternate iron assimilation pathways of *A. fumigatus* were able to remove transferrin-bound iron in the absence of hydroxamate siderophores.

TABLE 10

Growth of ΔsidA was inhibited by human serum and restored by addition of siderophores.

| Medium | dry weight (mg) parental | | ΔsidA | |
|---|---|---|---|---|
| GA | 4.3[1] | 1.1 | 1.2[1] | 0.4* |
| GA + FeCl$_3$ | 7.8[1] | 0.8 | 7.1[1] | 2.5 |
| GA + FeCl$_3$ + serum | 11.4[1] | 1.2 | 0.3[1] | 0.3** |
| GA + FeCl$_3$ + serum + TAF | 9.7[1] | 1.0 | 7.2[1] | 0.5 |
| GA + FeCl$_3$ + serum + ferricrocin | 11.1[1] | 1.8 | 11.0[1] | 1.2 |

*A. fumigatus* wild type and ΔsidA strains were cultured in 1 ml volumes of modified GA medium, or in various combinations of GA medium supplemented with 5 μM FeCl$_3$, 10% serum, 50 μM desferri-TAF of 50 μM desferri-ferricrocin, and incubated for 4 days at 37° C. and 150 rpm. At the end of the incubation period, mycelia were filtered, washed, lyophilized and weighed. Data presented areaverages[1] standard deviations combined from three independent experiments.
*Significantly different than the parental strain (P < 0.01)
**Significantly different than the parental strain (P < 0.001)

Example 3.4

Ferric Reductase Activity is not Sufficient to Compensate for Defects in Siderophore Secretion The inventors have further shown that *A. fumigatus* produces both cell-associated and soluble ferric reductase activity, but that this ferric reductase activity is not upregulated in the ΔsidA mutant. Ferric reductase assays were performed as described by Morrissey et al. (51). *A. fumigatus* wild type and ΔsidA strains were inoculated in GA medium (10$^6$ conidia/ml) containing 5 μM FeCl$_3$ and incubated at 37° C. and 150 rpm for 24 hours. Mycelia were filtered through MIRA-CLOTH™ (Calbiochem), washed with distilled water, and transferred to microcentrifuge tubes. Mycelia were incubated with 0.5 ml of 0.2 mM FeCl$_3$ in PBS plus 0.5 ml 2 mM bathophenanthrolinedisulfonic acid (BPDS, Sigma-Aldrich) in PBS at 37° C. and 150 rpm for 1 hour, at which time the absorbance of the supernatants were measured at 540 nm. To normalize the absorbance data to biomass, mycelia were then washed, lyophilized and dry weights obtained. *Saccharomyces cerevisiae* is known to express ferric reductase activity (52), and was used as a positive control in the ferric reductase assay.

Both wild type and ΔsidA produced measurable ferric reductase activity when grown in GA supplemented with 5 μM FeCl$_3$ or YG medium. Ferric reductase activity was found in both the cells and in the culture supernatant, though the levels of cell-associated activity were much higher (Table 11). There was little difference observed in the levels of ferric reductase activity in GA supplemented with 5 μM FeCl$_3$ compared to YG medium (Table 11), nor was any difference observed in the levels of ferric reductase expressed by the parental or ΔsidA strains (Table 11). These results indicate that ferric reductase activity was not upregulated in ΔsidA to compensate for the defect in siderophore secretion.

TABLE 11

Ferric reductase assay.

Absorbance at 540 nm/mg dry weight (×100)

|  | Medium 1 (GA + 5 μM FeCl$_3$) | | Medium 2 (YG) | |
|---|---|---|---|---|
| wild type | 7.6[1] | 2.2 | 4.9[1] | 0.6 |
| ΔsidA | 4.7[1] | 1.7 | 4.0[1] | 0.1 |

*A. fumigatus* wild type and ΔsidA strains were cultured for 24 hours in 1 ml volumes of modified GA medium containing 5 μM FeCl$_3$. Mycelia were transferred to an assay buffer containing 0.5 ml 0.2 mM FeCl$_3$ in PBS and 0.5 ml 2 mM BPDS in PBS and incubated at 37° C. and 150 rpm for 1 hour. Absorbances of supernatants were read at 540 nm. Data are reported as absorbances per mg dry weight of mycelia present in the reductase assay. Data shown are averages[1] standard deviations combined from three independent experiments.

Example 3.5

Siderophores are Requried for *A. fumigatus* to Remove Transferrin-Bound Iron

The inventors have also demonstrated that *A. fumigatus* requires siderophores to remove transferrin-bound iron. The ability of the siderophore secretion mutant, ΔsidA, to remove iron from human diferric transferrin was assessed in vitro. *A. fumigatus* (10$^6$ conidia/ml) was cultured in 1 ml modified GA medium supplemented with 50 μM FeCl$_3$ at 37° C. for 24 hours. Mycelia were washed 3 times with PBS, and resuspended in 1 ml minimal essential medium (MEM) containing no phenol red (pH 7.4, Life Technologies) supplemented with 0.2 mg/ml human diferrictransferrin (Sigma). Cultures were incubated at 37° C. and 150 rpm, and 100 μl samples were removed at various intervals. The samples were lyophilized to dryness and redissolved in 10 µl water+10 µl urea-polyacrylamide gel electrophoresis (urea-PAGE) loading buffer (1×TBE, 10% glycerol and 0.2% bromphenol blue). Urea-PAGE was used to determine the proportions of apo-, diferric-, and monoferric-transferrin in each sample. Urea-PAGE was carried out as described by Wolz et al. (28) using a Protean II xi cell (Bio-rad). Approximately 10 µg transferrin in a 10 µl volume was loaded onto each lane and gels were run at 200V for 18-20 hours at 4° C. Gels were incubated 30 minutes in 0.05% SDS, stained with SYPRO orange (Molecular Probes, Eugene, Oreg.) and scanned with a Typhoon 9410 imager (Amersham). Bands were quantified using ImageQuant 5.2 (Molecular Dynamics).

Both ΔsidA and the parental strain produced roughly equal mycelial biomass after 24 hours, but they had not yet begun to conidiate. Mycelia were washed three times in PBS and transferred to fresh tubes containing MEM+0.2 mg/ml human diferric transferrin. This extra incubation step was required because ΔsidA conidia cannot germinate and grow in MEM. The cultures were incubated at 37° C. in MEM/diferric transferrin and samples of supernatant were removed at various intervals.

Figure 23:
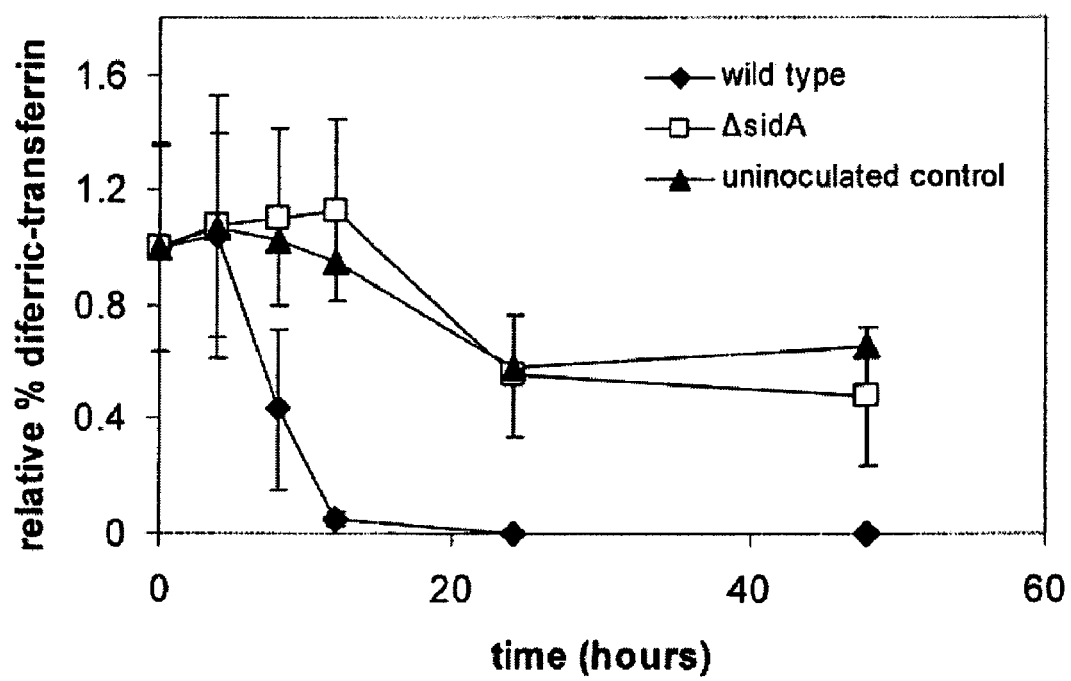
FIG. 23 shows iron saturation of human diferric-transferrin incubated with wild type or ΔsidA *A. fumigatus* mycelia. *A. fumigatus* wild type and ΔsidA mycelia were incubated in MEM containing 0.2 mg/ml human diferric-transferrin at 37° C. and 150 rpm. Iron saturation of transferrin was assessed by urea-PAGE. Gels were stained with SYPRO orange, scanned on a Typhoon 9410 Imager and the transferrin bands quantified using ImageQuant 5.2. Data are normalized and reported as % total transferrin present in diferric form/% transferrin in diferric form at t=0. Error bars represent standard deviations of triplicate measurements.

The supernatants were analysed by urea-PAGE to measure the iron saturation of transferrin. The gels were scanned and the transferrin bands quantified. Wild type cultures consumed all of the diferric transferrin within 12 hours (FIG. 23), converting it to monoferric transferrin and apotransferrin. In contrast, the levels of diferric transferrin in the ΔsidA culture remained identical to those of an uninoculated control over a period of at least 48 hours (FIG. 23). Therefore, the inventors have shown that siderophores are required by *A. fumigatus* for removal of iron from human diferric transferrin.

Example 4.0

Siderophores are Essential for the in Vivo Virulence of *A. fumigatus*

The inventors have further discovered that siderophores are essential for virulence of *A. fumigatus*. Because the siderophore secretion mutant strain ΔsidA was unable to grow in iron limited media, including serum, and was unable to remove iron from human diferric transferrin, the inventors compared its virulence to that of the parental strain in a mouse model of invasive aspergillosis. The mutant strain was avirulent in the mouse model, indicating that siderophore production is important in iron uptake of *A. fumigatus* in vivo. Furthermore, siderophore biosynthesis is required for the in vivo virulence of *A. fumigatus*. Because siderophore biosynthesis pathways are absent in human cells, these pathways represent potential new targets for antifungal chemotherapy.

The mouse model of invasive aspergillosis was developed using female BALB/c mice weighing from 18-22 g obtained from Charles River Breeders. The mice were given 0.5 mg/ml tetracycline in their drinking water throughout the course of the study. In the first experiment, mice were immunosuppressed by subcutaneous injections of 200 mg/kg cortisone acetate on days −3, 0, 2 and 4. Cortisone acetate was prepared as a 30 mg/ml suspension in sterile saline (Baxter Medical). For these studies, *A. fumigatus* was cultured on YG agar at 37° C. for 4 days to ensure conidia were fully mature and pigmented. Conidia were harvested as described and suspended in sterile saline. Survival data for mouse models were analysed by log rank analysis using Prism 4.0 software (GraphPad).

In a first experiment, mice were randomly assigned to one of three treatment groups: parental strain (n=10), ΔsidA (n=11) and saline (n=5). On day 0, mice were anaesthetised with isoflurane and $5\times10^6$ conidia of either wild type or ΔsidA were instilled intranasally in a 20 µl volume using a micropipette and a gel loading tip. Each inoculum was plated on YG agar to assess viability of conidida harvested from each strain. Mice were monitored twice daily for 14 days to observe any clinical symptoms. Mice were deemed to have reached endpoint if they displayed ruffled fur and one of the following: either (a) laboured breathing, hunching and decreased movement or (b) disorientation and loss of balance. Mice displaying either set of clinical symptoms were euthanized.

In a second experiment, the same procedures were repeated, except that mice were randomly assigned to one of four treatment groups: parental strain (n=10), ΔsidA (n=10), ΔsidA$^R$ (n=10) and saline (n=5). At endpoint or the end of the 14-day study, lungs were fixed by immediately opening the chest of the euthanized animal, isolating the trachea, and perfusing 10% formalin in PBS into the lung cavities. After two minutes, lungs were removed and further fixed at room temperature overnight in PBS containing 10% formalin. Lungs were subsequently paraffin-embedded, sectioned and stained with hematoxylin and eosin. Images were obtained on a Zeiss LSM10 confocal microscope equipped with a QImaging 10-bit camera.

Two distinct set of clinical symptoms were observed in infected mice. Some developed clear signs of pulmonary difficulties and showed laboured breathing, hunching, decreased mobility and ruffled fur. Other mice displayed what appeared to be symptoms of sinusitis or central nervous system impairment. These mice had a characteristic head tilt, became disoriented, agitated and showed signs of loss of balance. They often also displayed laboured breathing and eventually decreased mobility. Either one of these outcomes was classified as endpoint. About 50% of mice succumbing to infection by wild type *A. fumigatus* displayed the second group of symptoms.

Figure 24:
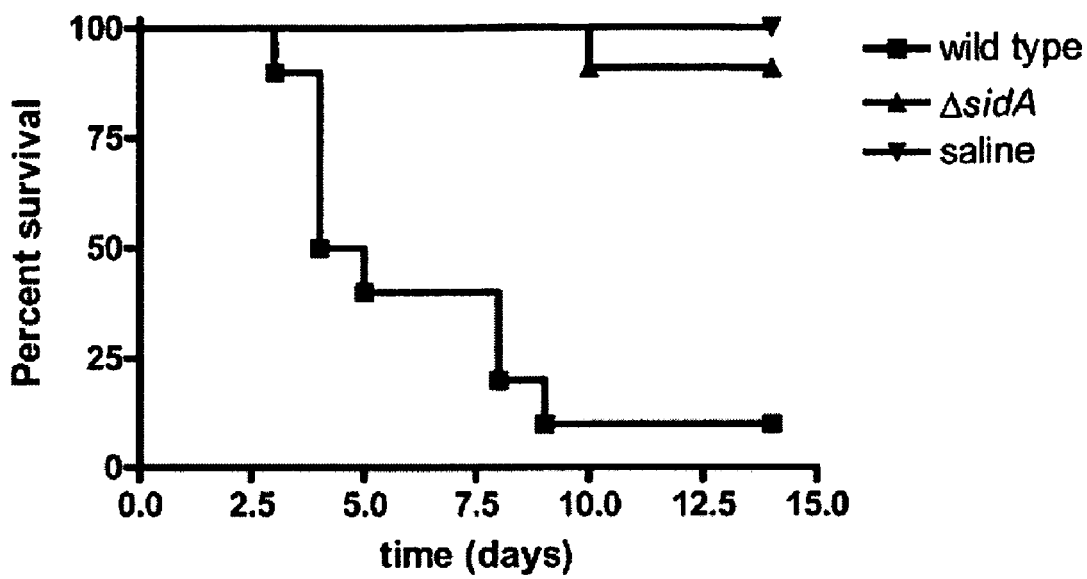
FIG. 24 shows survival curve of female BALB/c mice infected with *A. fumigatus* wild type or ΔsidA. Mice were infected with $5 \times 10^6$ conidia in 20 μl saline of either wild type or ΔsidA on day 0. Control mice were given saline alone. Mice were sacrificed if they displayed symptoms of infection. Survival curves for wild type and ΔsidA are significantly different (P<0.0001 by log rank analysis).

The ΔsidA mutant was completely avirulent in this model of invasive pulmonary aspergillosis. The results of this example are shown in FIG. 24. Endpoint was reached with 60% of mice infected with wild type, while mice infected with ΔsidA conidia showed survival rates equal to those of mice instilled with saline (100%). Wild type and ΔsidA conidia were plated following infection of the mice, and it was demonstrated that conidia from both strains had identical viabilities.

Figure 25:
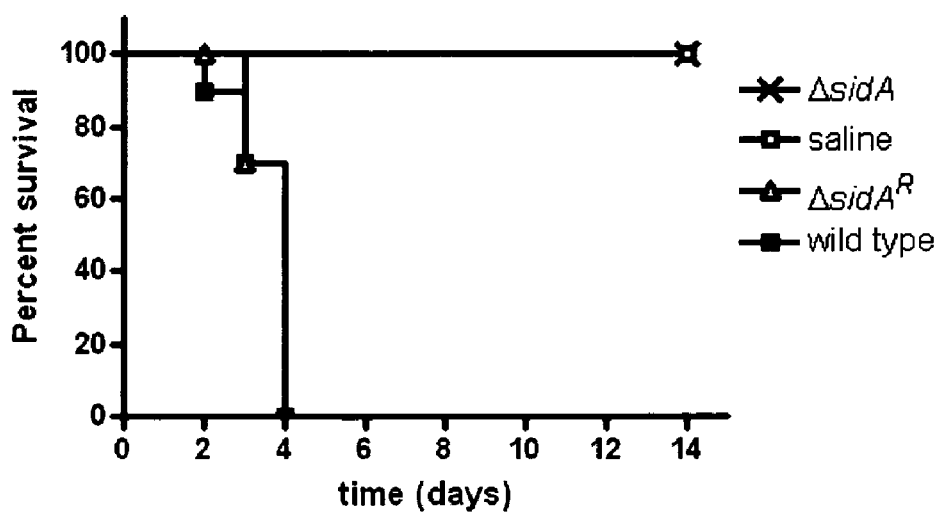
FIG. 25 shows a survival curve of female BALB/c mice infected with *A. fumigatus* wild type, ΔsidA or the rescued strain. Mice were immunosuppressed by subcutaneous injection of 200 mg/kg cortisone acetate on days −3, 0, 2 and 4. Mice were infected with $5 \times 10^6$ conidia in 20 μl saline of either wild type, ΔsidA$^R$ or ΔsidA on day 0. Control mice were given saline alone. Mice were monitored daily and sacrificed if they displayed symptoms of infection. Survival curves for wild type or ΔsidA$^R$ versus ΔsidA are significantly different (P<0.0001) by log rank analysis.

The second experiment in this example considered rescued ΔsidA strain of *A. fumigatus* (ΔsidA$^R$). As shown in FIG. 25, 100% of mice receiving the wild type or ΔsidA$^R$ reached endpoint by day 4 post-infection. In contrast, ΔsidA was avirulent in this model of invasive pulmonary aspergillosis (FIG. 25). None of the mice infected with ΔsidA conidia reached endpoint, which was not significantly different from the mortality rate of saline-inoculated, immunocompromised mice (FIG. 25).

To determine the extent of fungal growth, in the second experiment, the lungs of the mice were examined. Lung fixation was performed when mice reached endpoint, or at 14 days post-infection for the remaining mice. Lungs were fixed by immediately opening the chest of the euthanized animal, isolating the trachea, and perfusing 10% formalin in PBS into the lung cavities. After two minutes, lungs were removed and further fixed at room temperature overnight in PBS containing 10% formalin. Lungs were subsequently paraffin-embedded, sectioned and stained with hematoxylin and eosin. Images were obtained on a Zeiss LSM10 confocal microscope equipped with a QImaging 10-bit camera. Representative sections are shown in FIG. 26.

Figure 26:
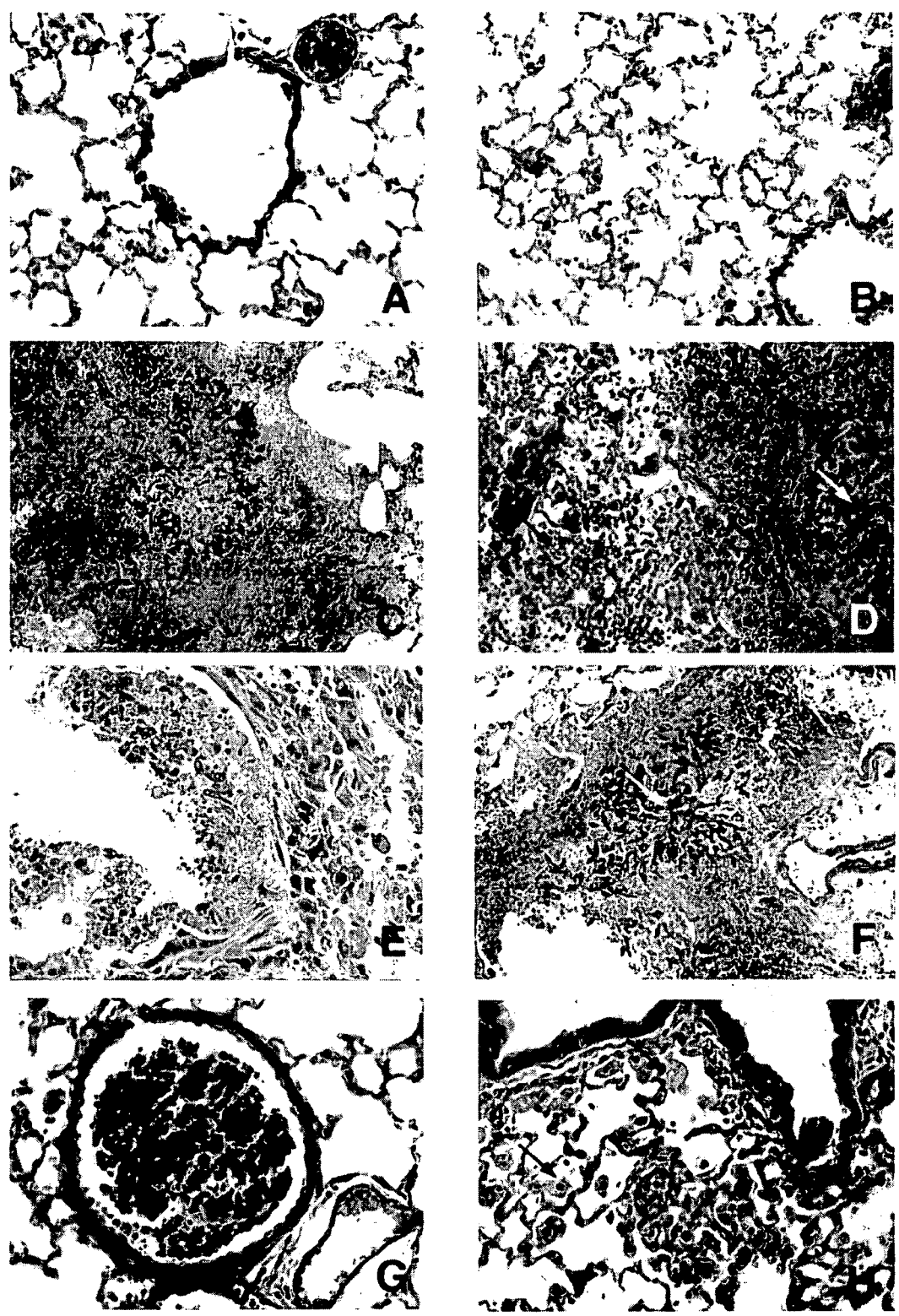
FIG. 26 shows lung tissue sections from cortisone-treated mice exposed to one of the following treatments: saline (A and B), wild type *A. fumigatus* conidia (C, D), conidia from the rescued strain (ΔsidA$^R$) (E, F), and ΔsidA *A. fumigatus* conidia (G and H). Each panel represents a section from a different animal. A and B (saline): Lungs have normal appearance with clear airways and no inflammatory infiltrate. C and D (wild type). Fungal hyphae (white arrow) within an airway accompanied by a neutrophil and monocyte infiltration; erythrocytes are seen within the airways (black arrow). E (rescued strain): Hyphae are seen within the bronchiole (arrows). F (rescue): Fungal growth evident within an airway (arrow) accompanied by necrosis. G (ΔsidA): Normal lung tissue surrounding a focus of inflammation confined to the lumen of a bronchiole. H (ΔsidA): No fungi were observed but foci containing large numbers of macrophages were observed (arrows). Original magnification was 400× except for panels C and F which were 200×.

Of the four saline-treated controls whose lungs were examined, all four showed normal lung structure with open airways and no inflammation (FIGS. 26, A and B). Fungal hyphae were observed in sections from the mice receiving the wild type strain. Fungal growth was accompanied by an extensive inflammatory infiltrate composed of polymorphonuclear leukocytes and monocytes. Extensive tissue destruction was apparent, including frank necrosis of the airway walls and large blood vessels, and complete replacement of alveolar architecture with necrosis and inflammation (FIGS. 26, C, D, and E). The mice that showed primarily CNS symptoms were also found to have fungal colonization of their lungs (see Panel C, FIG. 26). In the group that received the ΔsidA mutant strain, sections were examined from 7 mice. In the mice receiving ΔsidA, the lungs of four mice showed evidence of peribronchiolar or perivascular inflammation whereas the remaining two mice had no evidence of inflammatory response. Only one of the mice exposed to ΔsidA had evidence of fungi within the lungs 14 days post-infection. FIGS. 26 F, G and H show representative sections in which inflammation is evident. In G, inflammatory cells appeared to be confined to the lumen of the bronchioles. In panels F and H, there are leukocytes present in the airway walls, but in contrast to mice infected with the wild type strain, little necrosis is evident. One mouse had an extensive inflammatory response consisting of both PMNs and monocytes. Fungal hyphae are evident in the tissue sections (FIG. 26, panel F, arrow); however, the fungal growth was less extensive compared to wild type and tended to remain confined to the bronchiolar lumen.

Two possible mechanisms to explain the lack of virulence of the sidA strain in vivo may be that *A. fumigatus* is unable to utilize host iron sources sufficiently to allow growth and invasion in the absence of siderophores, and/or siderophore mutants may be more susceptible to ROS produced by phagocytic cells. Corticosteroids inhibit the conidicidal activity of tissue macrophages and also have been reported to stimulate a 30-40% increase in growth rate of *Aspergillus fumigatus* (53). In this model of immunosuppression, conidia are taken up by macrophages which are unable to inhibit their germination and growth. Thus, conidia are exposed to the airway surface fluids as well as an intracellular environment where other potential iron sources, such as ferritin, are found. Since the ΔsidA strain of *A. fumigatus* was unable to establish infection, none of the iron sources to which it is exposed in the host are sufficient to allow growth and invasion in the absence of siderophores in vivo. In addition, siderophore mutants may be more susceptible to ROS produced by phagocytic cells. Excess unbound iron can contribute to the formation of deleterious hydroxyl radicals, which catalyse damage to DNA and other essential molecules via Fenton chemistry. It has been demonstrated that lack of cellular siderophores increases sensitivity of *A. nidulans* to the redox-cycler paraquat (54).

In summary, in this example the inventors have demonstrated that sidA, a gene involved in the biosynthesis of hydroxamate siderophores, is required for the in vivo virulence of *A. fumigatus* in a mouse model of aspergillosis.

Example 5.0

Assay for Identifying Potential Inhibitors of *A. fumigatus* Siderophore Biosynthesis, Siderophore Secretion, or Siderophore Iron-Binding Capacity In accordance with the invention, an assay that may be used for screening for candidate agents capable of inhibiting siderophore biosynthesis, such as by inhibiting the enzymes ornithine oxygenase or non-ribosomal peptide synthetase, which catalyze steps in the biosynthetic pathway for hydroxamate siderophores (shown in FIGS. 12 and 13). The assay may also be used to identify inhibitors capable of interfering with the formation of an iron-siderophore complex. In one embodiment, the assay may be used for detecting inhibitors of L-ornithine $N^5$-oxygenase (ornithine oxygenase) of *Aspergillus fumigatus*.

In this example the assay to screen chemical agents for their ability to inhibit siderophore production by *A. fumigatus* uses the property of siderophores to change colour when they bind ferric iron. Fungal conidiospores (conidia) are inoculated into 96-well plates in low iron medium (which may be, for example, Neiland's Medium (55)) along with the inhibitor. After 24-48 h at 37° C., freshly-prepared ferrous sulphate is added (which rapidly converts to ferric iron in vitro) and the absorbance of the supernatant is measured at 430 nm. Wells which have a low absorbance at 430 nm indicate one of three possibilities:

1) the inhibitor prevented siderophore production by inhibiting ornithine oxygenase or non-ribosomal peptide synthetase (the second step in biosynthesis) (i.e. a siderophore-dependent inhibitor)
2) the inhibitor prevented growth and therefore siderophore production by an ornithine-oxygenase independent inhibition (i.e. a siderophore-independent inhibitor)
3) the inhibitor interfered with the formation of the iron-siderophore complex (i.e. a siderophore-dependent inhibitor).

To distinguish between the first two possibilities, a control plate is incubated at the same time which contains the same components plus ferric iron (added as ferrous sulphate). If the chemical inhibitor acts to depress fungal growth even in the presence of iron, the inhibition will be considered to be non-specific. Potential specific inhibitors should allow *A. fumigatus* to grow when iron is present as they no longer require siderophore production. Fungal growth is determined by measuring the turbidity after 48 hours at 600 nm.

Finally, agents that are considered to be candidate inhibitors are further screened to determine whether the low colour development is due to inhibition of ornithine oxygenase or due to interference of iron binding to the siderophore (possibility 3 above). For this component, the fungi are allowed to grow in Neiland's medium without the inhibitor for 24 hours, and the inhibitor is added just prior to iron addition. If the inhibitor prevents colour development, this indicates that the chemical interferes with the formation of the siderophore iron complex rather than inhibiting the function of the ornithine oxygenase.

Example 5.1

Use of Assay for Detecting Antibiotics Capable of Inhibiting Siderophore Production In this example 96-well sterile polystyrene filter plates as described above with white Duropore membranes at the base of the plate (Millipore) were used. The plates include a thick plastic layer under the wells, which has a one-way valve function that directs fluid into a receiving 96-well plate when the filter plate is subjected to a vacuum manifold or a centrifugal force. This layer can be peeled off if the membranes are to be sampled (punched) later.

Cultures were set up in the filter plates, with controls and inhibitors to be tested. After inclubation, culture fluid was pulled into a 96-well receiver plate, using the Beckman centrifuge and a JS 5.3 rotor designed to take 96-well plates. FeCl$_3$ was added to the receiver plates, and A$_{430}$ (general siderophores) or A$_{440}$ (max for TAF) was read. Growth was scored in the plate by reading A$_{600}$.

To test this method, different antibiotics were used to show inhibition of siderophore production by *A. fumigatus* 13073, as no inhibitors for the SidA gene product are currently known. Suitable ranges of concentrations of amphotericin B (fungizone), hygromycin, and nystatin were calculated based on the literature. Spores were harvested from *A. fumigatus* 13073 into PBS Tween, then washed once with PBS and counted. They were then diluted into Neilands' medium (without citrate) to give solutions of 2×10$^5$ and 2×10$^6$/ml. 100 µl of 2× spores and 100 µl of 2× antibiotics to yield a volume of 200 µl of Neilands' medium in each well, with the desired final concentrations of spores, 10$^5$ or 10$^6$/ml.

Antibiotics were prepared as follows. Amphotericin B came as a liquid solution, 250 g/ml. The MIC for amphotericin B for *A. fumigatus* in vitro is given as 0.12 to 0.15 g/ml. Therefore 0, 0.125, 0.25, 0.5, 1 and 2 g/ml final concentration was used. Nystatin was stored it in ~1 mg dry aliquots at −20 C, and was prepared at a concentration of 2 mg/ml in DMSO for dilution into Neilands' media. According to reported information, nystatin should be effective at 1.5 to 6.5 g/ml; therefore, 0, 0.5, 1, 5, 10 and 50 g/ml were used as the final concentrations. Hygromycin gold stock was in solution at 100 mg/ml, and 0, 25, 50, 100, 150 and 200 g/ml were used as the final concentrations in Neilands' medium. Plates were incubated for 3 days at 37° C. with shaking.

To test for siderophores, 20 µL of a solution of 2 mM FeCl$_3$ in 10 mM HCl was added to each well in the receiver plates and the A$_{440}$ was recorded on a plate reader. The presence of siderophores is indicated by grey shading in Table 12, where the A$_{440}$ was significantly higher than the blanks containing 0 spores (rows 2 and 6). An increase in A$_{440}$ indicates a more intense orange-red colour that develops in the presence of ferrated siderophores. These results confirm that at higher concentrations of known inhibitors, the A$_{440}$ decreases to values not significantly different to control wells containing no fungus. Because 3-day incubation produces conidia, shorter incubation periods may be preferable.

TABLE 12

Results of siderophore secretion inhibitor assay with amphotericin B, hygromycin, and nystatin.

(A)

| A. fumigatus | amphotericin B (µg/ml) | | | | | |
|---|---|---|---|---|---|---|
|  | 0.00 | 0.13 | 0.25 | 0.50 | 1.00 | 2.00 |
| 0 | 0.037 | 0.038 | 0.039 | 0.040 | 0.040 | 0.041 |
| 1.00E+05 | 0.237 | 0.178 | 0.038 | 0.042 | 0.032 | 0.041 |
| 1.00E+05 | 0.227 | 0.156 | 0.039 | 0.040 | 0.039 | 0.034 |
| 1.00E+05 | 0.247 | 0.145 | 0.040 | 0.039 | 0.036 | 0.041 |
| 0.00E+00 | 0.038 | 0.037 | 0.039 | 0.041 | 0.034 | 0.042 |
| 1.00E+06 | 0.235 | 0.211 | 0.085 | 0.038 | 0.037 | 0.036 |
| 1.00E+06 | 0.203 | 0.200 | 0.168 | 0.042 | 0.034 | 0.034 |
| 1.00E+06 | 0.261 | 0.211 | 0.130 | 0.035 | 0.121 | 0.036 |

(B)

| A. fumigatus | hygromycin (µg/m) | | | | | |
|---|---|---|---|---|---|---|
|  | 0 | 25 | 50 | 100 | 150 | 200 |
| 0 | 0.038 | 0.039 | 0.039 | 0.039 | 0.046 | 0.038 |
| 100000 | 0.275 | 0.173 | 0.138 | 0.283 | 0.042 | 0.037 |
| 1.00E+05 | 0.298 | 0.206 | 0.115 | 0.047 | 0.045 | 0.041 |
| 1.00E+05 | 0.254 | 0.131 | 0.100 | 0.046 | 0.058 | 0.036 |
| 0.00E+00 | 0.032 | 0.035 | 0.039 | 0.039 | 0.040 | 0.036 |
| 1.00E+06 | 0.347 | 0.335 | 0.057 | 0.176 | 0.253 | 0.047 |
| 1.00E+06 | 0.313 | 0.355 | 0.289 | 0.363 | 0.474 | 0.049 |
| 1.00E+06 | 0.306 | 0.351 | 0.323 | 0.376 | 0.052 | 0.057 |

(C)

| A. fumigatus | nystatin (µg/ml) | | | | | |
|---|---|---|---|---|---|---|
|  | 0 | 0.5 | 1 | 5 | 10 | 50 |
| 0 | 0.034 | 0.042 | 0.040 | 0.043 | 0.044 | 0.05 |
| 100000 | 0.268 | 0.341 | 0.340 | 0.048 | 0.043 | 0.048 |
| 100000 | 0.246 | 0.414 | 0.31 | 0.042 | 0.045 | 0.052 |
| 100000 | 0.253 | 0.359 | 0.325 | 0.044 | 0.042 | 0.051 |
| 0.00E+00 | 0.037 | 0.038 | 0.041 | 0.048 | 0.042 | 0.050 |
| 1000000 | 0.252 | 0.416 | 0.412 | 0.042 | 0.042 | 0.048 |
| 1000000 | 0.241 | 0.382 | 0.492 | 0.043 | 0.043 | 0.048 |
| 1000000 | 0.319 | 0.232 | 0.329 | 0.042 | 0.050 | 0.051 |

Tables show A$_{440}$ of *A. fumigatus* cultures growing in 96-well plates with (A) amphotericin B, (B) hygromycin, and (C) nystatin. A higher A$_{440}$ reading indicates the presence of ferrated siderophores.

Siderophore production and growth was scored by using one antibiotic (amphotericin B) with two types of media (Neilands' with and without citrate), using the same spore concentrations as given above, but a shorter incubation time. Generally, this portion of the assay would be carried out when there was a potential inhibitor which scored positively in the first round of screening. Growth is scored with and without iron in the media. This test will distinguish a compound inhibits siderophore biosynthesis, siderophore secretion, or formation of a siderophore-iron complex (i.e. a compound that inhibits growth of *A. fumigatus* in a siderophore-dependent manner) from one which inhibits growth of *A. fumigatus* generally (i.e. in a siderophore-independent manner).

Three identical plates were set up: one filter plate and two sterile clear 96-well plates. The clear plates were used to score growth, and the filter plate was used to detect siderophores. Columns 1-6 contained Neilands' medium without citrate and amphotericin 0-2 at g/ml. Columns 7-12 contained Neilands' medium with citrate and amphotericin at 0-2 g/ml. The rows were set up with *A. fumigatus* as described above, but two sets of each were set up to be in the two plates. The spores from the previous experiment were stored at −20° C. in PBS, in siliconized tubes, at 2×10$^8$ conidia/ml, to facilitate these experiments. Plates were incubated for 48 hours at 37° C. without shaking.

The filter plate was centrifuged at 1000×g for 10 minutes and the liquids caught in a clear non-sterile plate, to which FeCl$_3$ was added. The plate was allowed to sit and develop orange colour, and was then read at 440 nm. The clear plates (one without Fe and one with Fe added to growth medium from the beginning) were read at 600 nm (A$_{600}$). In the result, iron enhanced conidiation. Some wells of the filter plate were lightly conidiated and would not drain. These were hand pipetted.

The production of siderophores by *A. fumigatus* (A$_{440}$) in this experiment in media without citrate added are shown in Table 13, and the growth of duplicate cultures (A$_{600}$) is shown in Table 14. Results for media with citrate added were similar (data not shown). These results demonstrate that the same siderophore production pattern occurred for a 48-hour incubation as for a 72-hour incubation, although the amounts produced are slightly less after 48 hours. Siderophore production was inhibited by lower doses of antibiotic than growth; however, addition of iron did not change the pattern of growth inhibition. Thus, as expected, the mechanism of growth inhibition by amphotericin B is unrelated to the inhibition of siderophore biosynthesis, secretion, or the formation of the iron-siderophore complex.

TABLE 13

Siderophore production as measured by $A_{440}$ by *A. fumigatus* in presence of amphotericin B in Neilands' medium without citrate.

| *A. fumigatus* | amphotericin B (μg/ml) in Neilands' medium without citrate | | | | | |
|---|---|---|---|---|---|---|
| | 0 | 0.13 | 0.25 | 0.50 | 1 | 2 |
| 0 | 0.052 | 0.043 | 0.045 | 0.041 | 0.045 | 0.045 |
| 100000 | 0.067 | 0.042 | 0.043 | 0.046 | 0.045 | 0.045 |
| 100000 | 0.182 | 0.047 | 0.044 | 0.042 | 0.042 | 0.045 |
| 100000 | 0.175 | 0.042 | 0.044 | 0.043 | 0.041 | 0.045 |
| 0.00E+00 | 0.04 | 0.052 | 0.048 | 0.046 | 0.044 | 0.049 |
| 1000000 | 0.248 | 0.236 | 0.047 | 0.043 | 0.05 | 0.044 |
| 1.00E+06 | 0.243 | 0.217 | 0.046 | 0.043 | 0.047 | 0.043 |
| 1.00E+06 | 0.27 | 0.098 | 0.048 | 0.042 | 0.047 | 0.045 |

TABLE 14

Growth of *A. fumigatus* as measured by $A_{600}$ in presence of amphotericin B in Neilands' medium without citrate without iron (A) or with iron (B).

(A)

| *A. fumigatus* | amphotericin B (μg/ml) in Neilands' medium without citrate or Fe | | | | | |
|---|---|---|---|---|---|---|
| | 0 | 0.13 | 0.25 | 0.50 | 1 | 2 |
| 0 | 0.034 | 0.034 | 0.034 | 0.035 | 0.035 | 0.035 |
| 100000 | 0.101 | 0.122 | 0.068 | 0.035 | 0.035 | 0.035 |
| 100000 | 0.112 | 0.158 | 0.083 | 0.035 | 0.036 | 0.036 |
| 1.00E+05 | 0.109 | 0.256 | 0.076 | 0.035 | 0.036 | 0.035 |
| 0.00E+00 | 0.035 | 0.035 | 0.036 | 0.035 | 0.035 | 0.035 |
| 1.00E+06 | 0.158 | 0.137 | 0.111 | 0.038 | 0.039 | 0.038 |
| 1.00E+06 | 0.157 | 0.113 | 0.126 | 0.039 | 0.039 | 0.039 |
| 1000000 | 0.190 | 0.168 | 0.157 | 0.037 | 0.038 | 0.038 |

(B)

| *A. fumigatus* | amphotericin B (μg/ml) in Neilands' medium without citrate with Fe | | | | | |
|---|---|---|---|---|---|---|
| | 0 | 0.13 | 0.25 | 0.5 | 1 | 2 |
| 0 | 0.034 | 0.034 | 0.035 | 0.035 | 0.035 | 0.035 |
| 100000 | 0.101 | 0.122 | 0.067 | 0.035 | 0.035 | 0.035 |
| 1.00E+05 | 0.111 | 0.157 | 0.091 | 0.034 | 0.035 | 0.035 |
| 100000 | 0.108 | 0.255 | 0.076 | 0.035 | 0.035 | 0.035 |
| 0 | 0.035 | 0.035 | 0.034 | 0.035 | 0.035 | 0.035 |
| 1000000 | 0.159 | 0.139 | 0.11 | 0.038 | 0.039 | 0.038 |
| 1.00E+06 | 0.157 | 0.113 | 0.126 | 0.039 | 0.039 | 0.039 |
| 1000000 | 0.19 | 0.169 | 0.157 | 0.039 | 0.039 | 0.038 |

Example 6.0

Diagnostic Test for Detecting a Biomarker Indicative of Likely *A. fumigatus* Infection As indicated above, the inventors have studied the mechanisms by which *A. fumigatus* can survive and reproduce in the body fluids of the host. The inventors have determined that early in the life cycle of the fungus, large amounts of one siderophore, TAF, are secreted into serum-containing medium (see FIG. 7: the amount of TAF detectable by the CAS assay after only 8 hours of culture was 2 nmol/ml) (56). Although *A. fumigatus* secretes at least 5 different siderophores, more than 90% is comprised of TAF (56). TAF is a stable molecule, and the host does not synthesize TAF or related cyclic peptides. As TAF is unique to the pathogen, the inventors believe that TAF is an early marker of fungal infection in the blood of people infected with *A. fumigatus*.

Figure 27:
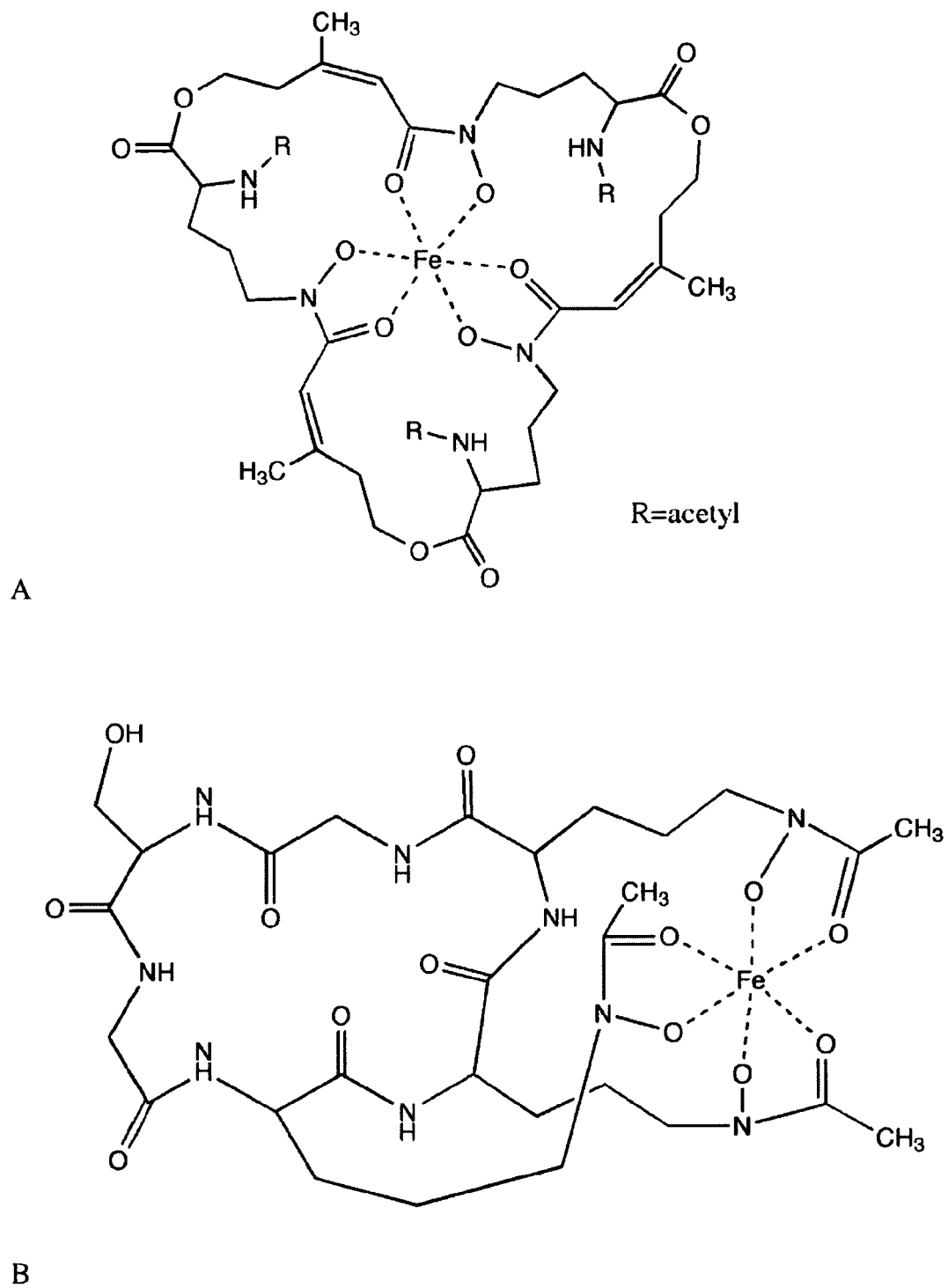
FIG. 27 shows the structures of N',N'',N'''-triacetylfusarinine C (TAF) (A) and ferricrocin (B) produced by *A. fumigatus*.

Therefore, the invention also relates to a diagnostic test for detecting a biomarker indicative of likely *A. fumigatus* infection. In one embodiment, the invention relates to an assay for detecting TAF in serum. TAF is a cyclic peptide of approximately 900 Da. The structure of TAF produced by *A. fumigatus* is shown in FIG. 27. As described above, the inventors have shown that TAF is produced in mg quantities from fungal culture, and that TAF is stable in human serum (56). Three different methods for detecting TAF in serum are disclosed.

In accordance with the first method, polyclonal antibodies to TAF in mice and rabbits may be produced to develop an ELISA test for TAF. In particular, monoclonal antibodies to TAF may be developed for an ELISA sandwich test. TAF alone is not immunogenic because of its small size. Therefore, TAF may be covalently linked to a carrier protein prior to injection. Because TAF has no reactive side chains available for chemical cross-linking (FIG. 27), the method may comprise using a bifunctional linker to bind TAF to a carrier protein: one end may be photoreactive and the other may allow linkage to Lys or Cys side chains on the carrier protein.

Figure 28:
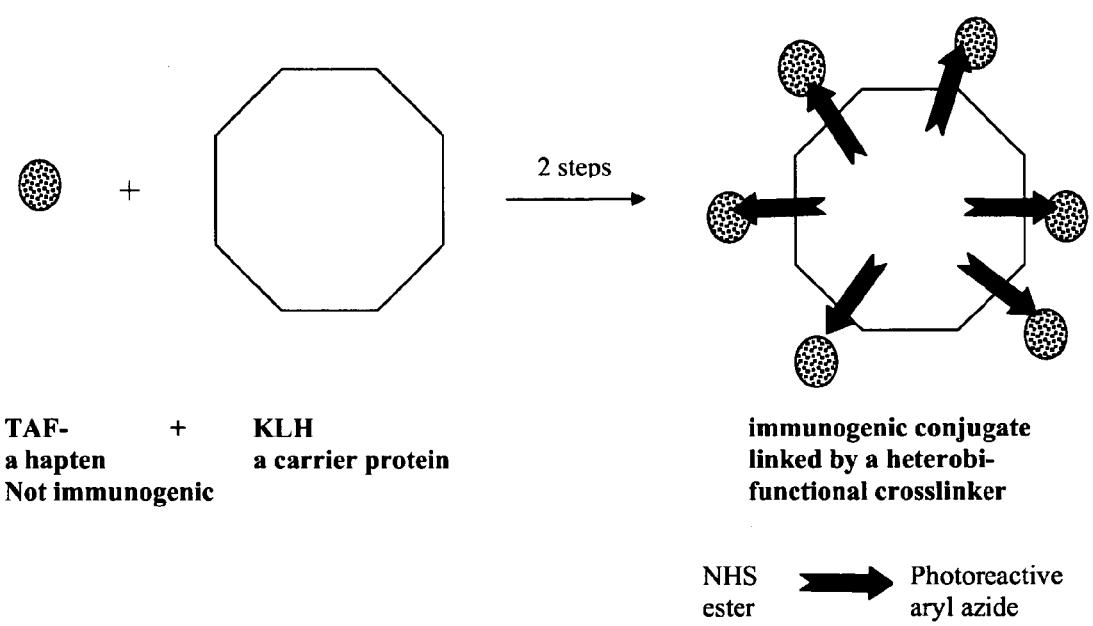
FIG. 28 is a schematic view depicting the reaction of a hapten (TAF) with a carrier protein (KLH) via a heterobifunctional reagent to create an immunogenic conjugate.

TAF may be covalently linked to the carrier protein, which may be, for example, keyhole limpet hemocyanin (KLH) (Mass $4.5 \times 10^5$ Da), prior to injection (FIG. 28). Most peptide conjugation reactions rely on free carboxylic acid, primary amine, sulflhydryl groups or phenolate or indole rings. Because TAF has none of these groups available for chemical cross-linking (see FIG. 27), a heterobifunctional linker containing an N-hydroxysuccinimidyl group linked to a photoreactive aryl azide (Pierce) may be utilized (FIG. 29). The NHS-ester may be reacted with primary amines of KLH in the dark, and the modified protein may be purified on a Sephadex G-25 column. Protein-containing fractions may be pooled, mixed with TAF, and the aryl azide group photolyzed with long wave UV light at room temperature for 10 minutes (15). In the same way, TAF may be conjugated to ovalbumin (mass 43 kDa) for use as a non-relevant carrier protein to test for specific anti-TAF antibodies using an ELISA assay. Because it is likely that a mixture of deferrated and ferrated TAF will be present in vivo, all of the above steps may also be carried out with deferrated TAF as well as a 1:1 mixture of the two forms. TAF may be deferrated according to Hissen et al. (57).

According to this example, New Zealand White rabbits (2.5 kg) may be immunized with the TAF-KLH complexes (2 rabbits per conjugate: ferrated TAF, deferrated TAF and 1:1 mixture) using alum solution from Pierce as the adjuvant, and boosted every 2 weeks for up to 8 weeks. Pre-immune sera may also be obtained. Blood may be obtained from the auricular vein and serial dilutions of serum may be tested using an ELISA assay. Antibody titres of serum may be determined in 96-well plates containing constant amounts of TAF-ovalbumin. Linking TAF to a non-relevant protein (ovalbumin) provides a mechanism to attach TAF to the ELISA plates while allowing the TAF epitopes to be accessible to the antibodies. Titres may be determined using a secondary anti-rabbit IgG conjugated with HRP. Colour development may be assessed in a microplate reader after incubation with a chromogenic substrate.

Samples of the TAF-KLH conjugate may also be used for the production of monoclonal antibodies. Mouse antisera may be screened in the immunization phase using the method described above, except that the secondary antibody is anti-mouse IgG. Ovalbumin and KLH are used as background controls and BSA is used to block the plates. Positive polyclonal sera may be aliquotted and stored frozen at −80° C. Antibodies may be purified using Protein G-agarose (KPL).

Prior to analysis by ELISA, the optimal method of blood processing may be determined (e.g., dilution in PBS, protein precipitation, solvent extraction) using mouse blood spiked with known amounts of TAF. TAF levels in the extracts will be determined by LC-MS or TLC-MALDI MS. To develop an ELISA capture assay for TAF, it is possible to:

1. Coat high-binding 96-well plate with purified anti-TAF antibody.
2. Block remaining binding sites on the plates with BSA or caseinate.
3. Add dilutions of processed sera with known amounts of TAF.
4. Wash out excess reagent to separate bound from free TAF.
5. Add a second anti-TAF antibody with detection molecule attached. Generally, the second antibody is labeled monoclonal (HRP-conjugated), and recognizes a different epitope than the adsorbed antibody.
6. After washing, the chromogenic HRP substrate may be added and the colour determined in a microplate reader.

To obtain optimal signal:noise ratio, it is possible to vary the types of plates used, the amount of antibody adsorbed, the pH/type of buffer used during binding, the ratio of the first and second antibody.

In accordance with a second method, the TAF may be absorbed on to an adjuvant, such as alum, and the resulting mixture may be injected. In particular, mice may be immunized using alum solution from Pierce as the adjuvant, and boosted every 2 weeks for up to 8 weeks. Blood may be obtained from the saphenous vein of the mice (100 μl) yielding 50 μl of serum. Serum may be tested for TAF-specific antisera in 96-well plates coated with a constant amount of TAF. Non-fat dry milk and ovalbumin will be used as the background control and BSA will be used to block the plates. Titres of TAF-specific antibodies will be detected using anti-mouse secondary antibodies linked to an enzyme marker.

A third method in accordance with the invention may involve the design and synthesis of DNA aptamers with strong affinity to TAF. DNA aptamer technology developed by Dr. Dipankar Sen is described in detail in PCT patent application No. PCT/CA03/00330 filed 11 Mar. 2003 and published under No. WO 03/076653 A2 on 18 Sep. 2003, which is hereby incorporated by reference. Using this Sen technology a chip may be fabricated for detecting and monitoring the presence and the quantities of TAF in patients. This methodology is capable of detecting electrical changes induced in the DNA fragments, based on conformational changes induced from binding to TAF.

As explained above, there is an established need for improved means for detecting *A. fumigatus* infection at an early stage. Because of the large amounts of TAF secreted in serum in vitro, and because anti-peptide antibodies have a higher affinity than anti-carbohydrate antibodies, the development of an ELISA assay to TAF may yield a specific and more sensitive assay than the PLATELIA™ *Aspergillus* ELISA test from Bio-Rad. Additionally, proteins usually have greater antigenic strength because they have a more complex structure than polysaccharides, i.e. proteins possess many more potential epitopes than do carbohydrates. Hence, the binding strength of the antibody to conjugated TAF is expected to be greater than for binding of antibody to galactomannan in an ELISA assay. The increased binding strength of the antibody to the TAF will increase the sensitivity of the reaction, i.e., the ability to detect lower amounts of antigen (TAF).

TAF also has the advantage that it is secreted early in infection (as conidia germinate) and does not require fungal cell damage to cause its release into the bloodstream. TAF is a relatively small molecule (900 Da) and is uncharged when bound to Fe (III) (FIG. 27A). Therefore, unlike galactomannan, ferrated TAF may be able to diffuse into the bloodstream/BAL even before tissue damage occurs. Additionally, TAF secretion is a marker for invasive aspergillosis caused by other *Aspergillus* spp. In addition to *A. fumigatus*, TAF is produced by at least 3 of the pathogenic species of *Aspergillus, A. nidulans, A niger* and *A. flavus*. Previous studies by Haas' group have shown that *A. nidulans* produces TAF as the major siderophore and we have determined that both *A. flavus* and *A. niger* also produce siderophores in medium containing serum (Dennis et al. unpublished results).

The assay according to this example is estimated to be approximately 6-fold less expensive than PCR, and, unlike conventional PCR, the assay is quantitative. The assay may, therefore, be used for monitoring fungal burden over the course of the illness.

The above-described ELISA assay or chip assay may be used as a diagnostic test in clinical laboratories to determine whether a patient has invasive aspergillosis. The assay may be quantitative, thereby allowing the extent of infection to also be determined.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

1. Latgñ, J. P. 1999. *Aspergillus fumigatus* and aspergillosis. Clin Microbiol Rev. 12:310-50.
2. Wald, A., W. Leisenring, J. A. van Burik, and R. A. Bowden. 1997. Epidemiology of *Aspergillus* infections in a large cohort of patients undergoing bone marrow transplantation. J Infect Dis. 175:1459-66.
3. Bodey, G., B. Bueltmann, W. Duguid, D. Gibbs, H. Hanak, M. Hotchi, G. Mall, P. Martino, F. Meunier, S. Milliken, and et al. 1992. Fungal infections in cancer patients: an international autopsy survey. Eur J Clin Microbiol Infect Dis. 11:99-109.
4. Minamoto, G. Y., T. F. Barlam, and N. J. Vander Els. 1992. Invasive aspergillosis in patients with AIDS. Clin Infect Dis. 14:66-74.
5. Segal, B. H., E. S. DeCarlo, K. J. Kwon-Chung, H. L. Malech, J. I. Gallin, and S. M. Holland. 1998. *Aspergillus nidulans* infection in chronic granulomatous disease. Medicine (Baltimore). 77:345-54.
6. Denning, D. W. 1998. Invasive aspergillosis. Clin Infect Dis. 26:781-803.
7. Steinbach W. J., Benjamin D. K. Jr., Kontoyiannis D. P., Perfect J. R., Lutsar I., Marr K. A., Lionakis M. S., Torres H. A., Jafri H. and Walsh T. J. (2004) Infections due to *Aspergillus terreus*: A multicentre retrospective analysis of 83 cases. Clin Infect Dis 39: 192-198.

8. International Bone Marrow Transplant Registry/Autologous Blood & Marrow Transplant Registry. IBMTR/ABMTR newsletter. http://www.ibmtr.org/newsleter/pdf/2002Feb.pdf.
9. Patterson, D. L., and N. Singh. 1999. Invasive aspergillosis in transplant recipients. Medicine 78:123-138.
10. Thomas K E, Owens C M, Veys P A, Novelli V and Costoli V (2003) The radiological spectrum of invasive aspergillosis in children: a 10-year review. Pediatr Radiol 33: 453-460.
11. Mennink-Kersten M A S H, Donnelly, J P, and Verweij P E (2004) Detection of circulating galactomannan for the diagnosis and management of invasive aspergillosis. Lancet Inf Dis 4: 349-357.
12. Bartholdy, B. A., M. Berreck, and K. Haselwandter. 2001. Hydroxamate siderophore synthesis by Phialocephalafortinii, a typical dark septate fungal root endophyte. Biometals 14:33>42.
13. Plattner, H. J., and Diekmann, H., (eds) (1994) Enzymology of siderophore biosynthesis in fungi. New York, N.Y.: Marcel Dekker.
14. Chenna, R., Sugawara, H., Koike, T., Lopez, R., Gibson, T. J., Higgins, D. G., and Thompson, J. D. (2003) Multiple sequence alignment with the Clustal series of programs. Nucleic Acids Res 31: 3497-3500.
15. Hermanson G T (1996) Bioconjugate Techniques, Academic Press, San Diego.
16. Bullen, J. J. 1 1981. The significance of iron in infection. Rev Infect Dis. 3:1127-38.
17. Ratledge, C., and L. G. Dover. 2000. Iron metabolism in pathogenic bacteria. Annu Rev Microbiol. 54:881-941.
18. Wessling-Resnick, M. 1999. Biochemistry of iron uptake. Crit Rev Biochem Mol. Biol. 34:285-314.
19. Eagle, H. 1959. Amino acid metabolism in mammalian cell cultures. Science. 130:432.
20. Kakuta, K., K. Orino, S. Yamamoto, and K. Watanabe. 1997. High levels of ferritin and its iron in fetal bovine serum. Comp Biochem Physiol A Physiol. 118:165-9.
21. Weinberg, E. D. 1977. Infection and iron metabolism. Am J Clin Nutr. 30:1485-90.
22. Tronchin, G., Bouchara, J-P., Larcher, G., Lissitzky, J-C., Chabasse, D. 1993. Interaction between *Aspergillus fumigatus* and basement membrane laminin: binding and substrate degradation. Biol Cell. 77: 201-8.
23. Bouchara, J. P., G. Larcher, F. Joubaud, P. Penn, G. Tronchin, and D. Chabasse. 1993. Extracellular fibrinogenolytic enzyme of *Aspergillus fumigatus*: substrate-dependent variations in the proteinase synthesis and characterization of the enzyme. FEMS Immunol Med Microbiol. 7:81-91.
24. Granger, D. L., J. R. Perfect, and D. T. Durack. 1986. Macrophage-mediated fungistasis: requirement for a macromolecular component in serum. J. Immunol. 137:693-701.
25. Wilson, M. E., R. W. Vorhies, K. A. Andersen, and B. E. Britigan. 1994. Acquisition of iron from transferrin and lactoferrin by the protozoan *Leishmania chagasi*. Infect. Immun. 62:3262-3269.
26. Gifford, A. H., J. R. Klippenstein, and M. M. Moore. 2002. Serum stimulates growth of and proteinase secretion by *Aspergillus fumigatus*. Infect. Immun. 70:19>26.
27. Laemmli, U. K. 1970. Cleavage of structural proteins during the assembly of the head of bacteriophage T4. Nature 227:680>685.
28. Wolz, C., K. Hohloch, A. Ocaktan, K. Poole, R. W. Evans, N. Rochel, A. M. Albrecht-Gary, M. A. Abdallah, and G. Doring. 1994. Iron release from transferrin by pyoverdin and elastase from *Pseudomonas aeruginosa*. Infect. Immun. 62:4021>4027.
29. Esparza, I., and J. H. Brock. 1980. The effect of trypsin digestion on the structure and iron-donating properties of transferrins from several species. Biochim. Biophys. Acta 622:297>307.
30. Okujo, N., T. Akiyama, S. Miyoshi, S. Shinoda, and S. Yamamoto. 1996. Involvement of vulnibactin and exocellular protease in utilization of transferrin- and lactoferrin-bound iron by *Vibrio vulnificus*. Microbiol. Immunol. 40:595>598.
31. Schwyn, B., and J. B. Neilands. 1987. Universal chemical assay for the detection and determination of siderophores. Anal. Biochem. 160:47>56.
32. Payne, S. M. 1994. Detection, isolation, and characterization of siderophores. Methods Enzymol. 235:329>344.
33. Jalal, M. A. F., and D. van der Helm. 1991. Isolation and spectroscopic identification of fungal siderophores, p. 235>269. In G. Winkelmann (ed.), *Handbook of microbial iron chelates*. CRC Press, Inc., Boca Raton, Fla.
34. Haselwandter, K., and G. Winkelmann. 2002. Ferricrocinoe an ectomycorrhizal siderophore of *Cenococcum geophilum*. Biometals 15:73>77.
35. Llinas, M., W. J. Horsley, and M. P. Klein. 1976. Nitrogen-15 nuclear magnetic resonance spectrum of alumichrome. Detection by a double resonance Fourier transform technique. J. Am. Chem. Soc. 98:7554>7558.
36. Llinas, M., M. P. Klein, and J. B. Neilands. 1972. Solution conformation of the ferrichromes. A comparative proton magnetic resonance study of glycine-and serine-containing ferrichromes. J. Mol. Biol. 68:265>284.
37. Nilius, A. M., and S. G. Farmer. 1990. Identification of extracellular siderophores of pathogenic strains of *Aspergillus fumigatus*. J. Med. Vet Mycol. 28:395>403.
38. Diekmann, H., and E. Krezdorn. 1975. [Metabolic products of microorganisms. 150. Ferricrocin, triacetylfusigen and other sideramines from fungi of the genus *Aspergillus*, group *Fumigatus* (in German; inventor's transl)]. Arch Microbiol 106:191-4.
39. Adjimani, J. P., and T. Emery. 1987. Iron uptake in *Mycelia sterilia* EP-76. J Bacteriol 18 169:3664-8.
40. Wong, G. B., M. J. Kappel, K. N. Raymond, B. Matzanke, and G. Winkelmann. 1983. Coordination chemistry of microbial iron transport compounds. 24. Characterization of coprogen and ferricrocin, two ferric hydroxamate siderophores. J Am Chem Soc 105:810-815.
41. Hissen, A. H., J. M. Chow, L. J. Pinto, and M. M. Moore. 2004. Survival of *Aspergillus fumigatus* in serum involves removal of iron from transferrin: the role of siderophores. Infect Immun 72:1402-8.
42. Wiebe, C., and G. Winkelmann. 1975. Kinetic studies on the specificity of chelate-iron uptake in *Aspergillus*. J. Bacteriol. 123:837>842.
43. Jalal, M. A., R. Mocharla, C. L. Barnes, M. B. Hossain, D. R. Powell, D. L. Eng-Wilmot, S. L. Grayson, B. A. Benson, and D. van der Helm. 1984. Extracellular siderophores from *Aspergillus ochraceus*. J. Bacteriol. 158:683>688.
44. Mei, B., A. D. Budde, and S. A. Leong. 1993. sid1, a gene initiating siderophore biosynthesis in *Ustilago maydis*: molecular characterization, regulation by iron, and role in phytopathogenicity. Proc Natl Acad Sci USA 90:903-7.
45. Anderson, M. J. 2004, posting date. A proposal for the naming of genes in *Aspergillus* species. [Online.]

46. Stehr, M., H. Diekmann, L. Smau, O. Seth, S. Ghisla, M. Singh, and P. Macheroux. 1998. A hydrophobic sequence motif common to N-hydroxylating enzymes. Trends Biochem Sci 23:56-7.
47. Sambrook, J., E. F. Fritsch, and T. Maniatis. 1989. Molecular cloning: a laboratory manual, 2nd ed. Cold Spring Harbor Laboratory Press, Cold Spring Harbor, N.Y.
48. May, G. S., J. Gambino, J. A. Weatherbee, and N. R. Morris. 1985. Identification and functional analysis of beta-tubulin genes by site specific integrative transformation in *Aspergillus nidulans*. J Cell Biol 101:712-9.
49. Brown, J. S., A. Aufauvre-Brown, and D. W. Holden. 1998. Insertional mutagenesis of *Aspergillus fumigatus*. Mol Gen Genet 259:327-35.
50. Weidner, G., C. d'Enfert, A. Koch, P. C. Mol, and A. A. Brakhage. 1998. Development of a homologous transformation system for the human pathogenic fungus *Aspergillus fumigatus* based on the pyrG gene encoding orotidine 5'-monophosphate decarboxylase. Curr Genet 33:378-85.
51. Morrissey, J. A., P. H. Williams, and A. M. Cashmore. 1996. *Candida albicans* has a cell-associated ferric-reductase activity which is regulated in response to levels of iron and copper. Microbiology 142:485-92.
52. Askwith, C. C., de Silva, D., and Kaplan, J. (1996) Molecular biology of iron acquisition in *Saccharomyces cerevisiae*. Mol Microbiol 20: 27-34.
53. Ng, T. T., Robson, G. D., and Denning, D. W. (1994) Hydrocortisone-enhanced growth of *Aspergillus* spp.: implications for pathogenesis. Microbiology 140 (Pt 9): 2475-2479.
54. Eisendle, M., H. Oberegger, I. Zadra, and H. Haas. 2003. The siderophore system is essential for viability of *Aspergillus nidulans*: functional analysis of two genes encoding l-ornithine $N^5$-monooxygenase (sidA) and a non-ribosomal peptide synthetase (sidC). Mol Microbiol 49:359-75.
55. J B Neilands in *Development of Iron Chelators for Clinical Use*. (A E Martell, W F Anderson and D G Badman, eds.), Elsevier/North Holland, N.Y., 1981.
56. Hissen A. H. T., J. M. T. Chow, J. Pinto, M. M. Moore 2004. Survival of *Aspergillus fumigatus* in serum involves removal of iron from transferrin: the role of siderophores. Infect. Immun 72: 1402-1408.
57. Hissen A H T and Moore M M (2005) Site-specific rate constants for iron acquisition from transferrin by the *Aspergillus fumigatus* siderophores N',N",N"'-triacetyl-fusarinine C and ferricrocin. J Biol Inorg Chem. 2005 Mar. 16; [Epub ahead of print]
58. Reichard, U., S. Buttner, H. Eiffert, F. Staib, and R. Ruchel. 1990. Purification and characterisation of an extracellular serine proteinase from *Aspergillus fumigatus* and its detection in tissue. J Med Microbiol. 33:243-51.

What is claimed is:

1. A method of diagnosing invasive *aspergillus* infection in a subject comprising detecting the presence of a virulence factor in serum of the subject, wherein the virulence factor comprises N'N"N'"-triacetylfusarinine C (TAF).

2. A method according to claim 1, wherein the detecting comprises reacting a sample of the serum with TAF-specific antibodies.

3. A method according to claim 1, wherein the detecting is in an enzyme-linked immunosorbent assay (ELISA) assay.

4. A method according to claim 1 wherein the detecting comprises exposing a sample of the serum to nucleotide aptamers specific to TAF and measuring changes in electrical conductance.

5. A method according to claim 4, wherein the nucleotide aptamers are DNA aptamers.

6. A method of screening for an *Aspergillus fumigatus* infection in a subject comprising detecting the presence of N'N"N'"-triacetylfusarinine C (TAF) in serum of the subject.

* * * * *

```
                          SEQUENCE LISTING

<160> NUMBER OF SEQ ID NOS: 21

<210> SEQ ID NO 1
<211> LENGTH: 1800
<212> TYPE: DNA
<213> ORGANISM: Aspergillus fumigatus

<400> SEQUENCE: 1
gatcttcact ctgcaagttc ctgacttgct tccacctgga aaaattacct cccctttgcc      60
ttccccgcct cagttttgac atcctcccgc ctcaagtata ggtacctaat cttcttttct     120
ttctttcttg tacgatctga tctatggaat ctgttgaacg gaagtcagaa tcgagctact     180
tgggtatgcg caacatgcag cccgagcagc gtctttcttt ggatcctccc cgcttgaggt     240
caacacccca ggatgagctt catgatcttc tgtgtgttgg gtttggaccc gcttccctgg     300
ccattgccat tgctttgcat gacgctctgg accctcgatt gaacaagtcc gcttccaata     360
tccatgcaca gcctaagatc tgcttcctgg agcgccagaa gcaatttgcg tggcactcgg     420
gtatgctggt ccccggttcc aagatgcaga tctccttcat caaggatctc gcaactctcc     480
gggacccccg cagcagtttt actttctca actacctcca ccagaagggc cgtctgattc     540
acttcactaa cctcagcacc ttcctgccgg ctcggctgga gttcgaggac tacatgcgtt     600
ggtgtgcgca acaattttcg gatgtagtgg cttacgggga agaggtggtc gaagtgattc     660
ccgggaagtc tgatcccagc agctcggtgg ttgacttctt cactgttcgg tcgcgcaacg     720
ttgagacggg cgagatcagt gccaggagga cccgcaaggt cgttattgca atcggaggca     780
ctgcaaagat gccatccgga ctgccccagg atccccggat tatacactcg tccaagtact     840
gcacaacgct gccggccctg ttgaaggaca agtcgaagcc ttacaacatt gccgttctgg     900
gcagtggtca gagtgctgcg gagattttcc atgaccttca aaagagatat cccaactcac     960
gaacaacgct gattatgcgg gattctgcaa tgcggcccag tgacgactcg cctttgtgag    1020
```

-continued

```
cagagaatca agtaatccat attctgcttt ccgttttact gacataagtc tagtgtgaat    1080
gagatcttca accccgagcg agtcgacaag ttctacagcc aatctgccgc agaacgccag    1140
cgctctctcc tcgccgacaa ggctaccaac tacagtgttg tccgcctgga gttgattgag    1200
gagatctata cgacatgta cctgcagagg gtgaagaacc ctgacgaaac tcagtggcag    1260
catcgcatcc ttccggaacg caagatcaca cgggtcgagc accatggtcc tcagagtcga    1320
atgcgcatcc acctcaagtc atccaagccc gagtcggaag cgcagcaaa cgacgtcaaa    1380
gaaacgctgg aagtcgacgc tctcatggtg gctacaggct acaatcgcaa cgcgcacgag    1440
cgactcctga gcaaggttca acacttgaga cctacgggac aggatcagtg gaagccccac    1500
cgagattacc gggttgagat ggacccgagc aaggtcagct cagaagccgg catctggctt    1560
caaggttgta atgagcggac gcatggcctt agtgacagtt tgctgtcggt actggctgtt    1620
cgtggtggcg agatggtcca atcgattttc ggagagcagc tggaaagagc ggcggtacag    1680
ggccaccagc tacgagccat gctgtaaggg gcccgaaaaa agtggaggaa aagccggatt    1740
gcatagttag ttactgtttc aaggcgttgc gctaagcgaa tgccaaggcc atttctctga    1800
```

```
<210> SEQ ID NO 2
<211> LENGTH: 501
<212> TYPE: PRT
<213> ORGANISM: Aspergillus fumigatus

<400> SEQUENCE: 2

Met Glu Ser Val Glu Arg Lys Ser Glu Ser Ser Tyr Leu Gly Met Arg
1               5                   10                  15

Asn Met Gln Pro Glu Gln Arg Leu Ser Leu Asp Pro Pro Arg Leu Arg
            20                  25                  30

Ser Thr Pro Gln Asp Glu Leu His Asp Leu Leu Cys Val Gly Phe Gly
        35                  40                  45

Pro Ala Ser Leu Ala Ile Ala Ile Ala Leu His Asp Ala Leu Asp Pro
    50                  55                  60

Arg Leu Asn Lys Ser Ala Ser Asn Ile His Ala Gln Pro Lys Ile Cys
65                  70                  75                  80

Phe Leu Glu Arg Gln Lys Gln Phe Ala Trp His Ser Gly Met Leu Val
                85                  90                  95

Pro Gly Ser Lys Met Gln Ile Ser Phe Ile Lys Asp Leu Ala Thr Leu
            100                 105                 110

Arg Asp Pro Arg Ser Ser Phe Thr Phe Leu Asn Tyr Leu His Gln Lys
        115                 120                 125

Gly Arg Leu Ile His Phe Thr Asn Leu Ser Thr Phe Leu Pro Ala Arg
    130                 135                 140

Leu Glu Phe Glu Asp Tyr Met Arg Trp Cys Ala Gln Gln Phe Ser Asp
145                 150                 155                 160

Val Val Ala Tyr Gly Glu Glu Val Glu Val Ile Pro Gly Lys Ser
                165                 170                 175

Asp Pro Ser Ser Ser Val Val Asp Phe Phe Thr Val Arg Ser Arg Asn
            180                 185                 190

Val Glu Thr Gly Glu Ile Ser Ala Arg Thr Arg Lys Val Val Ile
        195                 200                 205

Ala Ile Gly Gly Thr Ala Lys Met Pro Ser Gly Leu Pro Gln Asp Pro
    210                 215                 220

Arg Ile Ile His Ser Ser Lys Tyr Cys Thr Thr Leu Pro Ala Leu Leu
225                 230                 235                 240
```

```
Lys Asp Lys Ser Lys Pro Tyr Asn Ile Ala Val Leu Gly Ser Gly Gln
            245                 250                 255

Ser Ala Ala Glu Ile Phe His Asp Leu Gln Lys Arg Tyr Pro Asn Ser
        260                 265                 270

Arg Thr Thr Leu Ile Met Arg Asp Ser Ala Met Arg Pro Ser Asp Asp
    275                 280                 285

Ser Pro Phe Val Asn Glu Ile Phe Asn Pro Glu Arg Val Asp Lys Phe
290                 295                 300

Tyr Ser Gln Ser Ala Ala Glu Arg Gln Arg Ser Leu Leu Ala Asp Lys
305                 310                 315                 320

Ala Thr Asn Tyr Ser Val Val Arg Leu Glu Leu Ile Glu Glu Ile Tyr
                325                 330                 335

Asn Asp Met Tyr Leu Gln Arg Val Lys Asn Pro Asp Glu Thr Gln Trp
            340                 345                 350

Gln His Arg Ile Leu Pro Glu Arg Lys Ile Thr Arg Val Glu His His
        355                 360                 365

Gly Pro Gln Ser Arg Met Arg Ile His Leu Lys Ser Ser Lys Pro Glu
    370                 375                 380

Ser Glu Gly Ala Ala Asn Asp Val Lys Glu Thr Leu Glu Val Asp Ala
385                 390                 395                 400

Leu Met Val Ala Thr Gly Tyr Asn Arg Asn Ala His Glu Arg Leu Leu
                405                 410                 415

Ser Lys Val Gln His Leu Arg Pro Thr Gly Gln Asp Gln Trp Lys Pro
            420                 425                 430

His Arg Asp Tyr Arg Val Glu Met Asp Pro Ser Lys Val Ser Ser Glu
        435                 440                 445

Ala Gly Ile Trp Leu Gln Gly Cys Asn Glu Arg Thr His Gly Leu Ser
    450                 455                 460

Asp Ser Leu Leu Ser Val Leu Ala Val Arg Gly Gly Glu Met Val Gln
465                 470                 475                 480

Ser Ile Phe Gly Glu Gln Leu Glu Arg Ala Ala Val Gln Gly His Gln
                485                 490                 495

Leu Arg Ala Met Leu
            500

<210> SEQ ID NO 3
<211> LENGTH: 32
<212> TYPE: DNA
<213> ORGANISM: Artificial Sequence
<220> FEATURE:
<223> OTHER INFORMATION: Chemically synthesized synthetic construct

<400> SEQUENCE: 3
aagcttaagc ttttgaacgg aagtcagaat cg                                    32

<210> SEQ ID NO 4
<211> LENGTH: 32
<212> TYPE: DNA
<213> ORGANISM: Artificial Sequence
<220> FEATURE:
<223> OTHER INFORMATION: Chemically synthesized synthetic construct

<400> SEQUENCE: 4
tctagatcta gaacaggttc cctcatgtct gc                                    32
```

<210> SEQ ID NO 5
<211> LENGTH: 30
<212> TYPE: DNA
<213> ORGANISM: Artificial Sequence
<220> FEATURE:
<223> OTHER INFORMATION: Chemically synthesized synthetic construct

<400> SEQUENCE: 5
aacgttaacg ttgtaaaacg acggccagtg                                    30

<210> SEQ ID NO 6
<211> LENGTH: 19
<212> TYPE: DNA
<213> ORGANISM: Artificial Sequence
<220> FEATURE:
<223> OTHER INFORMATION: Chemically synthesized synthetic construct

<400> SEQUENCE: 6
ggaaacagct atgaccatg                                                19

<210> SEQ ID NO 7
<211> LENGTH: 20
<212> TYPE: DNA
<213> ORGANISM: Artificial Sequence
<220> FEATURE:
<223> OTHER INFORMATION: Chemically synthesized synthetic construct

<400> SEQUENCE: 7
ttgaacggaa gtcagaatcg                                               20

<210> SEQ ID NO 8
<211> LENGTH: 20
<212> TYPE: DNA
<213> ORGANISM: Artificial Sequence
<220> FEATURE:
<223> OTHER INFORMATION: Chemically synthesized synthetic construct

<400> SEQUENCE: 8
acaggttccc tcatgtctgc                                               20

<210> SEQ ID NO 9
<211> LENGTH: 20
<212> TYPE: DNA
<213> ORGANISM: Artificial Sequence
<220> FEATURE:
<223> OTHER INFORMATION: Chemically synthesized synthetic construct

<400> SEQUENCE: 9
gacatatcca cgccctccta                                               20

<210> SEQ ID NO 10
<211> LENGTH: 20
<212> TYPE: DNA
<213> ORGANISM: Artificial Sequence
<220> FEATURE:
<223> OTHER INFORMATION: Chemically synthesized synthetic construct

<400> SEQUENCE: 10
actgtcgggc gtacacaaat                                               20

<210> SEQ ID NO 11
<211> LENGTH: 20
<212> TYPE: DNA
<213> ORGANISM: Artificial Sequence
<220> FEATURE:
<223> OTHER INFORMATION: Chemically synthesized synthetic construct

```
<400> SEQUENCE: 11
acgccctcaa ctgtatggac                                                      20

<210> SEQ ID NO 12
<211> LENGTH: 20
<212> TYPE: DNA
<213> ORGANISM: Artificial Sequence
<220> FEATURE:
<223> OTHER INFORMATION: Chemically synthesized synthetic construct

<400> SEQUENCE: 12
tttcgtgcaa aacagtggag                                                      20

<210> SEQ ID NO 13
<211> LENGTH: 32
<212> TYPE: DNA
<213> ORGANISM: Artificial Sequence
<220> FEATURE:
<223> OTHER INFORMATION: Chemically synthesized synthetic construct

<400> SEQUENCE: 13
gaattcgaat tctgtcaaga gcaccacacc tc                                        32

<210> SEQ ID NO 14
<211> LENGTH: 32
<212> TYPE: DNA
<213> ORGANISM: Artificial Sequence
<220> FEATURE:
<223> OTHER INFORMATION: Chemically synthesized synthetic construct

<400> SEQUENCE: 14
gaattcgaat tcccatcaga taacgcgtga aa                                        32

<210> SEQ ID NO 15
<211> LENGTH: 27
<212> TYPE: DNA
<213> ORGANISM: Artificial Sequence
<220> FEATURE:
<223> OTHER INFORMATION: Chemically synthesized synthetic construct

<400> SEQUENCE: 15
ctccatatgg aatctgttga acggaag                                              27

<210> SEQ ID NO 16
<211> LENGTH: 30
<212> TYPE: DNA
<213> ORGANISM: Artificial Sequence
<220> FEATURE:
<223> OTHER INFORMATION: Chemically synthesized synthetic construct

<400> SEQUENCE: 16
ccgaattctt attacagcat ggctcgtagc                                           30

<210> SEQ ID NO 17
<211> LENGTH: 501
<212> TYPE: PRT
<213> ORGANISM: Aspergillus fumigatus

<400> SEQUENCE: 17

Met Glu Ser Val Glu Arg Lys Ser Glu Ser Ser Tyr Leu Gly Met Arg
1               5                   10                  15

Asn Met Gln Pro Glu Gln Arg Leu Ser Leu Asp Pro Pro Arg Leu Arg
            20                  25                  30
```

```
Ser Thr Pro Gln Asp Glu Leu His Asp Leu Cys Val Gly Phe Gly
        35                  40                  45

Pro Ala Ser Leu Ala Ile Ala Ile Ala Leu His Asp Ala Leu Asp Pro
    50                  55                  60

Arg Leu Asn Lys Ser Ala Ser Asn Ile His Ala Gln Pro Lys Ile Cys
65                  70                  75                  80

Phe Leu Glu Arg Gln Lys Gln Phe Ala Trp His Ser Gly Met Leu Val
                85                  90                  95

Pro Gly Ser Lys Met Gln Ile Ser Phe Ile Lys Asp Leu Ala Thr Leu
            100                 105                 110

Arg Asp Pro Arg Ser Ser Phe Thr Phe Leu Asn Tyr Leu His Gln Lys
            115                 120                 125

Gly Arg Leu Ile His Phe Thr Asn Leu Ser Thr Phe Leu Pro Ala Arg
        130                 135                 140

Leu Glu Phe Glu Asp Tyr Met Arg Trp Cys Ala Gln Gln Phe Ser Asp
145                 150                 155                 160

Val Val Ala Tyr Gly Glu Val Val Glu Val Ile Pro Gly Lys Ser
                165                 170                 175

Asp Pro Ser Ser Ser Val Val Asp Phe Phe Thr Val Arg Ser Arg Asn
            180                 185                 190

Val Glu Thr Gly Glu Ile Ser Ala Arg Arg Thr Arg Lys Val Val Ile
        195                 200                 205

Ala Ile Gly Gly Thr Ala Lys Met Pro Ser Gly Leu Pro Gln Asp Pro
        210                 215                 220

Arg Ile Ile His Ser Ser Lys Tyr Cys Thr Thr Leu Pro Ala Leu Leu
225                 230                 235                 240

Lys Asp Lys Ser Lys Pro Tyr Asn Ile Ala Val Leu Gly Ser Gly Gln
                245                 250                 255

Ser Ala Ala Glu Ile Phe His Asp Leu Gln Lys Arg Tyr Pro Asn Ser
            260                 265                 270

Arg Thr Thr Leu Ile Met Arg Asp Ser Ala Met Arg Pro Ser Asp Asp
        275                 280                 285

Ser Pro Phe Val Asn Glu Ile Phe Asn Pro Glu Arg Val Asp Lys Phe
        290                 295                 300

Tyr Ser Gln Ser Ala Ala Glu Arg Gln Arg Ser Leu Leu Ala Asp Lys
305                 310                 315                 320

Ala Thr Asn Tyr Ser Val Val Arg Leu Glu Leu Ile Glu Glu Ile Tyr
                325                 330                 335

Asn Asp Met Tyr Leu Gln Arg Val Lys Asn Pro Asp Glu Thr Gln Trp
            340                 345                 350

Gln His Arg Ile Leu Pro Glu Arg Lys Ile Thr Arg Val Glu His His
        355                 360                 365

Gly Pro Gln Ser Arg Met Arg Ile His Leu Lys Ser Ser Lys Pro Glu
        370                 375                 380

Ser Glu Gly Ala Ala Asn Asp Val Lys Glu Thr Leu Glu Val Asp Ala
385                 390                 395                 400

Leu Met Val Ala Thr Gly Tyr Asn Arg Asn Ala His Glu Arg Leu Leu
                405                 410                 415

Ser Lys Val Gln His Leu Arg Pro Thr Gly Gln Asp Gln Trp Lys Pro
            420                 425                 430

His Arg Asp Tyr Arg Val Glu Met Asp Pro Ser Lys Val Ser Ser Glu
        435                 440                 445
```

```
Ala Gly Ile Trp Leu Gln Gly Cys Asn Glu Arg Thr His Gly Leu Ser
    450                 455                 460

Asp Ser Leu Leu Ser Val Leu Ala Val Arg Gly Gly Glu Met Val Gln
465                 470                 475                 480

Ser Ile Phe Gly Glu Gln Leu Glu Arg Ala Ala Val Gln Gly His Gln
                485                 490                 495

Leu Arg Ala Met Leu
            500

<210> SEQ ID NO 18
<211> LENGTH: 498
<212> TYPE: PRT
<213> ORGANISM: Aspergillus nidulans

<400> SEQUENCE: 18

Met Glu Pro Leu Gln Arg Lys Ser Glu Ile Asp Phe Gln Ser Tyr Arg
1               5                   10                  15

Lys Met Pro Leu Ala Gln Gln Arg Thr Gln Arg Leu Lys Pro Thr Ser
                20                  25                  30

Pro Glu Glu Leu His Asp Leu Ile Cys Val Gly Phe Gly Pro Ala Ser
            35                  40                  45

Leu Ala Ile Ala Ile Ala Leu His Asp Ala Leu Asp Pro Cys Leu Asn
        50                  55                  60

Lys Cys Ala Pro Thr Ser Gly Trp Gln Pro Lys Val Ala Phe Leu Glu
65                  70                  75                  80

Arg Gln Lys Gln Phe Ala Trp His Ser Gly Met Leu Val Pro Gly Ser
                85                  90                  95

Arg Met Gln Ile Ser Phe Ile Lys Asp Leu Ala Thr Leu Arg Asp Pro
            100                 105                 110

Arg Ser Ser Phe Thr Phe Leu Asn Tyr Leu His Gln Lys Asp Arg Leu
        115                 120                 125

Ile His Phe Thr Asn Leu Ser Thr Phe Leu Pro Ala Arg Met Glu Phe
130                 135                 140

Glu Asp Tyr Met Arg Trp Cys Ala Asn Gln Phe Ser Asp Val Val Thr
145                 150                 155                 160

Tyr Gly Glu Glu Val Ile Glu Val Leu Pro Gly Lys Ser Ser Pro Asp
                165                 170                 175

Ser Pro Val Val Asp Tyr Phe Thr Val Leu Ser Arg Asn Val Glu Thr
            180                 185                 190

Gly Glu Ile Ser Ser Arg Ser Ala Arg Lys Val Val Leu Ala Leu Gly
        195                 200                 205

Gly Thr Ala Lys Leu Pro Ala Glu Leu Pro Gln Asp Pro Arg Ile Met
210                 215                 220

His Ser Ser Lys Tyr Cys Thr Ala Leu Pro Asn Leu Leu Lys Asp Asn
225                 230                 235                 240

Asn Glu Pro Tyr Asn Ile Ala Val Leu Gly Ser Gly Gln Ser Ala Ala
                245                 250                 255

Glu Ile Phe His Asp Leu Gln Lys Arg Tyr Pro Asn Ser Arg Thr Ser
            260                 265                 270

Leu Ile Met Arg Asp Thr Ala Met Arg Pro Ser Asp Asp Ser Pro Phe
        275                 280                 285

Val Asn Glu Val Phe Asn Pro Glu Arg Thr Asp Lys Phe Tyr Asn Leu
290                 295                 300

Ser Ala Ala Glu Arg Glu Arg Ser Leu Lys Ala Asp Lys Ala Thr Asn
305                 310                 315                 320
```

```
Tyr Ser Val Val Arg Leu Glu Leu Ile Glu Glu Ile Tyr His Asp Met
                325                 330                 335

Tyr Leu Gln Arg Val Lys Asn Pro Asp Glu Thr Gln Trp Gln His Arg
            340                 345                 350

Ile Leu Pro Ser Arg Lys Ile Thr Arg Val Glu His Tyr Gly Pro Asn
        355                 360                 365

Lys Arg Met Arg Val His Val Arg Ala Val Lys Asp Gly Lys Asp Ser
370                 375                 380

Leu Ile Gly Asp Gly Lys Glu Val Leu Glu Val Asp Ala Leu Met Val
385                 390                 395                 400

Ala Thr Gly Tyr Asn Arg Asn Ala His Glu Gln Leu Leu Ser Lys Val
                405                 410                 415

Gln Tyr Leu Arg Pro Ala Thr Gln Asp Arg Trp Thr Pro Ser Arg Asp
            420                 425                 430

Tyr Arg Val Asp Leu Asp Arg Ser Lys Val Ser Ala Gly Ala Gly Ile
        435                 440                 445

Trp Leu Gln Gly Ser Asn Glu Gln Thr His Gly Leu Ser Asp Ser Leu
450                 455                 460

Leu Ser Val Leu Ala Thr Arg Gly Gly Glu Met Val Glu Ser Ile Phe
465                 470                 475                 480

Gly Glu Gln Leu Glu Ser Ala Ala Val Pro Asp Thr Arg Phe Arg Ala
                485                 490                 495

Met Leu

<210> SEQ ID NO 19
<211> LENGTH: 502
<212> TYPE: PRT
<213> ORGANISM: Aspergillus oryzae

<400> SEQUENCE: 19

Met Glu Pro Val Glu Arg Lys Leu Glu Ile Gly Ser Arg Ser Tyr Ser
1               5                   10                  15

Lys Met Pro Leu Thr Gln Gln Arg Ser Ser Gly Glu Pro Pro Arg Leu
            20                  25                  30

Lys Ala Thr Pro Lys Asp Glu Leu His Asp Leu Leu Cys Val Gly Phe
        35                  40                  45

Gly Pro Ala Ser Leu Ala Ile Ala Ile Ala Leu His Asp Ala Leu Asp
    50                  55                  60

Pro Cys Leu Asn Lys Thr Pro Asn Ser Asn Trp Gln Pro Lys Val Cys
65                  70                  75                  80

Phe Leu Glu Arg Gln Lys Gln Phe Ala Trp His Ser Gly Met Leu Val
                85                  90                  95

Pro Gly Ser Lys Met Gln Ile Ser Phe Ile Lys Asp Leu Ala Thr Met
            100                 105                 110

Arg Asp Pro Arg Ser Ser Phe Thr Phe Leu Asn Tyr Leu His Gln Lys
        115                 120                 125

Asp Arg Leu Ile His Phe Thr Asn Leu Ser Thr Phe Leu Pro Ala Arg
    130                 135                 140

Met Glu Phe Glu Asp Tyr Met Arg Trp Cys Ala Gln Arg Phe Ala His
145                 150                 155                 160

Val Val Ser Tyr Gly Glu Glu Val Ile Glu Val Ile Pro Gly Lys Thr
                165                 170                 175

Asn Pro Ser Ser Thr Leu Val Asp Phe Phe Thr Val Lys Ser Arg Asn
            180                 185                 190
```

```
Val Glu Thr Gly Glu Ile Ser Ala Arg Met Ala Arg Lys Val Val
    195                 200                 205
Ala Leu Gly Gly Thr Ala Lys Leu Pro Lys Glu Leu Pro Gln Asp Pro
210                 215                 220
Arg Ile Met His Ser Ser Lys Tyr Cys Thr Thr Leu Pro Ala Met Leu
225                 230                 235                 240
Lys Asp Ser Arg Glu Ala Tyr Asn Ile Ala Val Leu Gly Ser Gly Gln
                245                 250                 255
Ser Ala Ala Glu Ile Phe His Asp Leu Gln Lys Arg Tyr Pro Asn Ser
                260                 265                 270
Lys Thr Thr Leu Ile Met Arg Asp Thr Ala Met Arg Pro Ser Asp Asp
                275                 280                 285
Ser Pro Phe Val Asn Glu Val Phe Asn Pro Glu Arg Val Asp Lys Phe
                290                 295                 300
Phe Ser Leu Ser Ser Ala Glu Arg Gln Arg Ser Leu Thr Ala Asp Lys
305                 310                 315                 320
Ala Thr Asn Tyr Ser Val Val Arg Leu Glu Leu Ile Glu Gln Ile Phe
                325                 330                 335
Asn Asp Met Tyr Leu Gln Arg Val Gln Asn Pro Asp Glu Thr Gln Trp
                340                 345                 350
Gln His Arg Ile Leu Pro Gly Arg Lys Ile Thr Arg Val Glu His Tyr
                355                 360                 365
Gly Pro His Arg Arg Met Arg Leu His Val Arg Ala Val Lys Asp Glu
                370                 375                 380
Lys Asp Ser Leu Val Gly Asn Gly Lys Glu Thr Leu Glu Val Asp Ala
385                 390                 395                 400
Leu Met Val Ala Thr Gly Tyr Asn Arg Asn Ala His Glu Gln Leu Leu
                405                 410                 415
Lys Asn Val Gln His Leu Arg Pro Ala Gly Gln Glu Asn Trp Thr Pro
                420                 425                 430
Asn Arg Glu Tyr Arg Val Glu Leu Asp Pro Ser Lys Val Asn Ala Gln
                435                 440                 445
Ala Gly Ile Trp Leu Gln Gly Cys Asn Glu Gln Thr His Gly Leu Ser
                450                 455                 460
Asp Ser Leu Leu Ser Ile Leu Ala Ser Arg Ser Gly Glu Met Val Asn
465                 470                 475                 480
Ser Ile Phe Gly Gly Glu Phe Ala Gly Thr Thr Val Pro Asp Thr Thr
                485                 490                 495
His Ile Arg Ala Met Leu
                500

<210> SEQ ID NO 20
<211> LENGTH: 59
<212> TYPE: DNA
<213> ORGANISM: Aspergillus fumigatus

<400> SEQUENCE: 20
tgtgagcaga gaatcaagta atccatattc tgctttccgt tttactgaca taagtctag       59

<210> SEQ ID NO 21
<211> LENGTH: 13
<212> TYPE: PRT
<213> ORGANISM: Aspergillus fumigatus
```

```
<400> SEQUENCE: 21

Ala Leu Met Val Ala Thr Gly Tyr Asn Arg Asn Ala His
1               5                   10
```